United States Patent
Ma et al.

(10) Patent No.: US 11,466,287 B2
(45) Date of Patent: Oct. 11, 2022

(54) COMPOSITIONS AND METHODS TO INCREASE RESISTANCE TO PHYTOPHTHORA IN SOYBEAN

(71) Applicants: CORTEVA AGRISCIENCE LLC, Indianapolis, IN (US); PURDUE RESEARCH FOUNDATION, West Lafayette, IN (US)

(72) Inventors: Jianxin Ma, West Lafayette, IN (US); Rajat Aggarwal, Indianapolis, IN (US); Liyang Chen, West Lafayette, IN (US); Weidong Wang, West Lafayette, IN (US); Oswald Crasta, Bangord, CT (US); Jonathan Myrvold, Indianapolis, IN (US)

(73) Assignees: CORTEVA AGRISCIENCE LLC, Indianapolis, IN (US); PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 17/575,218

(22) Filed: Jan. 13, 2022

(65) Prior Publication Data
US 2022/0186247 A1 Jun. 16, 2022

Related U.S. Application Data

(63) Continuation of application No. PCT/US2021/063556, filed on Dec. 15, 2021.

(60) Provisional application No. 63/154,913, filed on Mar. 1, 2021, provisional application No. 63/126,283, filed on Dec. 16, 2020.

(51) Int. Cl.
C12N 15/82 (2006.01)

(52) U.S. Cl.
CPC .................. *C12N 15/8279* (2013.01)

(58) Field of Classification Search
None
See application file for complete search history.

(56) References Cited

U.S. PATENT DOCUMENTS

| 7,507,874 B2 | 3/2009 | Han |
| 9,493,843 B2 | 11/2016 | Chaky |
| 10,174,387 B2 | 1/2019 | Bai |
| 10,995,377 B2 | 5/2021 | Ma |
| 11,041,167 B2 | 6/2021 | Behm |
| 2013/0198912 A1 | 8/2013 | Hudson et al. |

OTHER PUBLICATIONS

UniProt Accession No. I1K139_SOYBN, Glycine max (Soybean) (*Glycine hispida*) AAA domain-1-5, 31-33 containing protein, Jun. 13, 2012 [online]. [Retrieved on Mar. 3, 2022]. Retrieved from the internet: <URL: https://www.uniprot.org/uniprot/I1K139> Entire document.
PCT International Search Report and Written Opinion completed by the ISA/US dated May 4, 2022 and issued in connection with PCT/US2021/063556.
Jieqing Ping et al., Theor Appl Genet (2016) 129:445-451.
Weidong Wang et al, Nature Communications 12, Article No. 6263 (2021): 1-8.

*Primary Examiner* — Medina A Ibrahim
(74) *Attorney, Agent, or Firm* — Barnes & Thornburg LLP

(57) ABSTRACT

Provided are compositions comprising polynucleotides encoding Rps genes, and soybean plants or soybean seeds comprising the compositions and exhibiting resistance to *Phytophthora*. Additionally, various methods for employing the polynucleotides to increase resistance to *Phytophthora* are also provided herein.

8 Claims, 14 Drawing Sheets

Figure 1:
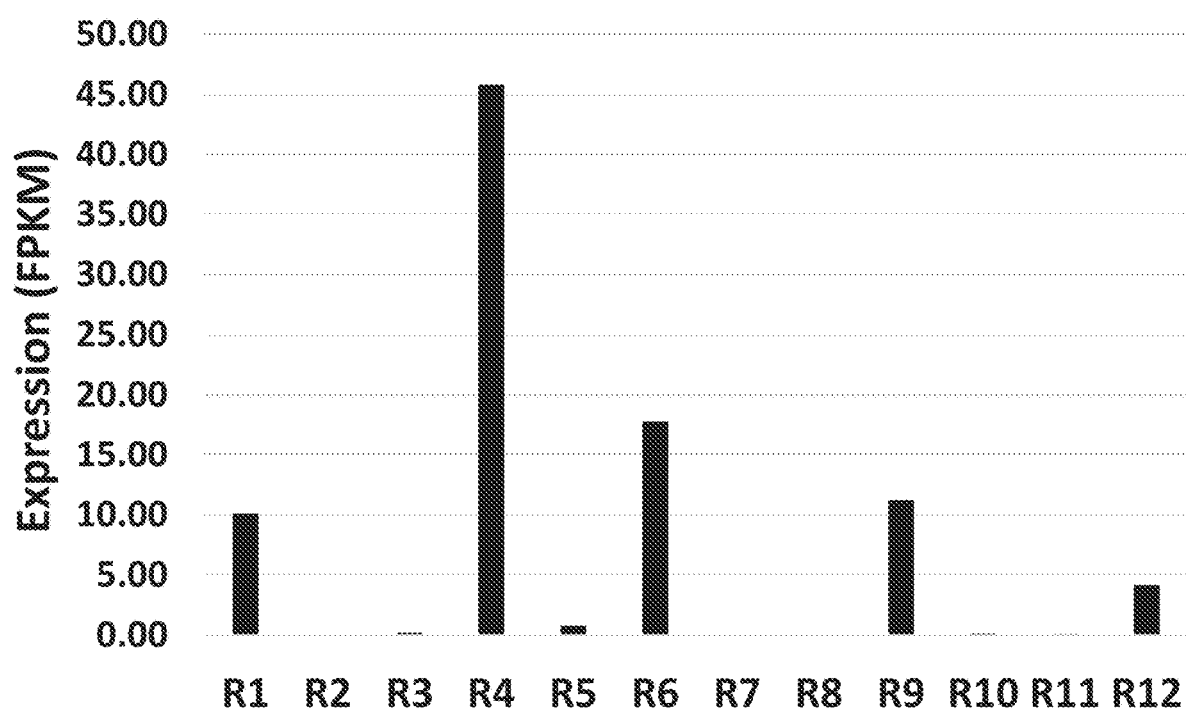

Specification includes a Sequence Listing.

SEQUENCE LISTING

```
<160> NUMBER OF SEQ ID NOS: 123

<210> SEQ ID NO 1
<211> LENGTH: 14034
<212> TYPE: DNA
<213> ORGANISM: Glycine max

<400> SEQUENCE: 1
atggacgctg tgtcatccgc actactagag ccagtaacta attctgtgtt ggatctgctt      60
aaaaagcaag tggattacat ccgttacagg cgaaactttg atgaactaga cgagtgtgtt     120
aagcagctta aacataaaaa ggagatagta gatcatcaat gtgaggaagc tgtcaaaaat     180
ggacacgaaa ttgaaggtaa ggttagagaa tggttaggga aagtgggtaa atttgagaca     240
gaagtggaga agtattggaa cgatgatggc cacaaaaaga cacggttttc caactattta     300
tttccttact ttaggcatag actaggcaga ctagcaaaga agatggcagt tgagggtaaa     360
aagataaccg atgattgccc aaagtctgat gaaattgcct ataggggtata cgtaacatct     420 aattatgcca ttttgtctaa taatgacctt atggattttg ttctagaaa atccataatg       480 gaacaaataa tggcaacact tgttgaagat cccactgtga aaatgattgg agtgtatgga     540
cgaagtgggg tgggtaagag cactttaatc aaagcaattg ctaaaattgc tcgagacaag     600
aagttgttta atgtggtggc tttttcagaa ataacagaca accccaatct aaaacaagtc     660
caggaagata ttgcttaccc tttgggattg aaattggaag gagaaggtga gaatgtaaga     720
gctgatcatc tacgaaggag gttaaagaaa gagaaagaga acacccttat aatcttggat     780
gacctttggg acagattaga cttgaatagg ttgggaattc cacttgatgg tgatgttgat     840
```

```
gataaacagg gtcccaaagg gccgacaaaa gaaaaatctc ttgctgatta taagggttgc      900
aaaattttgc taacttcaag gaaacgaaat gtattaacgg ataaaatgga agttaaatta      960
actttctgtg tagaggaatt agatgaaaaa gatgctctga agttgtttcg aaggaggct      1020
gcaatacaag gtgaaatgtc caagtctaaa aagaaattg ttaagaagta ttgtgctggg      1080
ttacctatgg caatagttac agttggaagg gcattaagag acaagagcga ctcagagtgg      1140
gaaaaactta aaaccaaga actggtggga gttcagaatc cgatggagat ttctgtaaaa      1200
atgagttatg accatctaga aaatgaggag ctcaagtcca ttttctttct ttgtgctcaa      1260
atgggtcatc aaccctaat tatgacttg tgaagtatt gctttggttt gggaatactt      1320
gaagggtct actcgcttgg ggaagctcgg gacagaatat ctacatcaat caaaaagctg      1380
aaagactcag gtttggtgtt ggatggaagt tctagtattc atttcaatat gcacgatctg      1440
gttcgagatg ctgctttatc tatagcacag aacgagcaaa atgtatttac tttgagaaat      1500
gggaaactta atgattggcc tgaactcaag aggtgcactt ctatttctat atgcaatagt      1560
gatatcattg atgagcttcc taatgttatg aactgtcctc aacttaaatt tttccaaatt      1620
gacaatgatg atccatcttt aaaaatacct gagagttttt ttaagagaat gaaaaaactc      1680
agagtgttaa tattgactgg ctttcatcta tcaagcttac catcatcaat taagtgccta      1740
tcagacctca gattgctttg tttggagcga tgcactttag atcacaactt atccatcata      1800
gggaagctga aaaaattaag aattctcagc ttttctggat ctcgaattga aaatttgcca      1860
gctgagttga aggacttgga taaactacaa ttactagaca tcagcaattg ttcaatagtc      1920
accatgattc cacctaatct tatatcaagg ttgacttcgt tggaagagct gtatgtaaga      1980
aagtgtttca tggaagtgtc ggaggaagga gagagaaacc aaagtcaaaa ttcatttatt      2040
tctgaactaa agcatttgca tcaattgcaa gtggtggact taagcattcc atgtgctgaa      2100
ttttttgcaa aggaattgtt ctttgacaac ttaagtgatt acaagattga gattgggaac      2160
ttcaaaactc tttcagctgg agatttcaga atgcctaata gtatgaaaaa tttcaaatct      2220
ttggcattgg agctgaagga tgacactgac aatattcact ctcagacagg aataaagttg      2280
ttgtttgaaa cagttgaaaa tttgttgttg ggagagctga atggtgttca agatgttgtt      2340
aatgagttga atttgaatgg atttccacat ctgaaacact tttccatcgt aaacaaccct      2400
agcatcaaat atatcatcaa ctcaaaggat ttgttttatc ctcaggatgt ttttcccaag      2460
ttggaatctc tatgcctcta caaactaaaa gagatagaga tgatatactt tagttcaggt      2520
acagagatga tatgctttag tccatttaca gattgctcat tcaccaaatt aaaaaccatc      2580
aaggtcgaga agtgtgatca attgaagaat cttttctcct tttgcatggt taaattgctt      2640
gcgagtcttg aaacaattgg tgtttccaat tgtggttctt tagaggagat cattaaaata      2700
ccagacaatt ctgataagat tgagtttctt aagttgatgt ctttgtcact tgaatcatta      2760
tcatcattca ctagttttta taccacagta gaggggtctt ctacaaacag agatcagata      2820
caaattactg ttatgactcc tcctcttttt ggtgaactgg tatgatagtg catattttc      2880
ctttaaaaat tttaattagt ctgtgactac ttatttttca gttgcaaata tgttaattgt      2940
gtatgtgctt gcaggttgaa ataccaaact tagagaactt gaatttaatc tcaatgaaca      3000
agatccagaa gatatggagc gaccagcccc cgtcaaactt ctgctttcag aacttaataa      3060
aattagttgt gaaagattgt caaaatttga gatatttgtg ttcattgtcc gtggccagca      3120
gtttgaggaa actgaaaggc ctctttgtaa gcaactgtaa aatgatggag aagatttta      3180
gcacagaagg aaatagtgca gacaaggtgt gtataggtgt aaataagtaa atttttatag      3240
```

```
ttgactgaat gttatgcatt tctgtttagt ttcattacca aataatggct tgttttcatc    3300
gaagtgcagg tttgcgtctt tcctaagttg gaggaaattc acctcgacca aatggatgag    3360
ttaacagaca tatggcaagc tgaagtgagt gctgattcct tttctagtct cacttctgtg    3420
aacattcgta gttgtcataa actagacaaa attttccga gtcacatgga aggatggttt     3480
gcgagtttga acagcttgaa ggtttctttt tgtgagtcag tggaagtgat ttttgaaatc    3540
aaagattctc agcaagtaga tgcatctggt gggatagaca caaatttgca ggttgtttat    3600
gtaagtgaac tcccaaagtt ggagcaggtg tggagcaggg atccaggagg aattcttaac    3660
ttcaaaaaac tgcagagtat agagatggat gattgtgaaa gactgaggaa tgtatttcca    3720
gcttctgtgg gcaaagatgt tccaaagctt gaatacatgt cggtcataga gtgtgatgga    3780
attgtggaaa ttgttgcctg tgaagatgga tccgaaacaa acactgaaca attagtgttt    3840
cctgaactaa ccgacatgga attatgttac ctatcaagca tccagcattt ctacagggg    3900 agacatccta tagagtgtcc aaaattgaag aagttgtcag tagggaaatg taacgagaag    3960
ctaaaaacat tcggaaccgg agaaggagc aatgaagaag atgaagcagt tatgtcagct    4020
gaaaaggtaa gtcatatagt gagacataaa tggagagtga tattgtaaga tgtgtggcat    4080
acttaaaaaa gatatagccc tgctaaatat aatatggatt attaatttaa cgtctctcgt    4140
cccctaatcc ctctaaatcc aaattcctca ttgtgcctta aaattttatt tagaatttag    4200
aattgaaggg aatgtttgat taattattat aatttaagag cattttttag ttttgatggg    4260
acccgagagt aaccaatgtg caggcaaggc gtaaaataat ggaaaggggc gctccatcag    4320
ggataagctt ccttcttcat agtttactat ttactttat tttattttc tgtagatatt       4380 ccccaacttg gagtatttgg atattcactt tgacgaagca cagaagtggt tattgagcaa    4440
cactgtgaag catcgaatgc accgtttaaa aaagcttagg ttaagcgaag ttaatgatgg    4500
tgaacgtctc tgtcaaattc tgtacagaat gccaaatcta gaaaagttat acttgccgat    4560
ggctaaacat ttgcttaaag agtcgtcgga gtcccgtttg ggaaccctat tacagctgaa    4620
ggaattggat ttgtggaggt cggagataaa ggatatagga tttgaacgag aaccagttct    4680
acagagacta gagcttttga gcttatttaa gtgccataaa ttgaggaatt tgggtcctcc    4740
ctcggtatca ttggcttact tgacaaattt gaaagtagag tattgttatg gattaaggaa    4800
tttaatggca tcctcaacgg caaaaagctt ggttcaactt aagtccatga agataagaaa    4860
atgttgtaaa ttagaggaaa tagtaagcga tgagggaaat gaagaagaag agcaaatagt    4920
gtttggcaaa ttgattacta tagaacttga ggggctaaaa aagctgaaaa gttttgtgcag   4980 ttccaagaac tatgaattca aattcccgtc attggaagga ttgattgtga aaaatgccc     5040 aatgatgcat acattcacgg agggtgacgc aagagcacca agttagaaa acacagttac     5100 tgctaaagaa gaaggaaaag aggaagccaa atggcagtgg aaggagact tgaattccac     5160 catacaaaaa ggtttcaaca aggtacttat tcatttattt atgatttaaa tatatttta     5220 tttatcttgt tagtattttt ttattcttcc ttttttattt ttgttcttca agttattat     5280 ttttgttaat tttagtcttt ttaggttatt tcattcattt ttaatacgtt aattttttt     5340 aaaatttag tctctttaat attttaaaat attcattat aatcctccgc acgaaattaa      5400
aattaaaaaa tataaactta taaaataaaa aatgagtaaa acatattacg gagatcaaaa    5460
ttaaaaaagc ataaactttc aacgactaaa attaaaaaaa aaaacttac cagagacaaa     5520 aattaaaaaa tattaactta catttatcaa atacatattt aaacttatat ttattacaaa    5580
```

```
ttctcctagt tttattaact tttcttcttt ccttacaaaa acaaactttt cttctttcat   5640
gagataaaaa aaattacttg ccatgaatgg aaattataaa tccttgtttt tcccataaaa   5700
agccttaacc agcaagtatg ttaaatttct taagatataa atatgttagc tcaaaaaacc   5760
agcatttata taaatttatt aatcattttt gttttaaaaa aattcattca taaaatttaa   5820
aataatacga atgtgactgc ttcatgtagc cagcgtagtc ataagaaaaa cattccctca   5880
tcttacaact ttttttttta attataataa ataaacttca attcatattt gattatcatc   5940
cattaatttt ttgttaacat ttttagtcct tttagaaatt tttgctcatt attaatccta   6000
ttgtttatgt tatatttaag aaaaaaaaac gactaaaaat ggatcgatga acacattttt   6060
agagggatta aaactttaaa gaaagattga aatttgtaaa aaaattgagg gggaaaaatt   6120
agaatataaa aaaatgagga gttaaaaact taattacatt tgactttaca tatataaaat   6180
aacatataaa cgtgataata aattaacaaa cttatccata taatttgtga ctatttatat   6240
atctataaaa taaagtcac atgagacgtt attataactt acaaggttga ttttgtagtt   6300
ggaaaaaaga atttgaaggg aaaaggatga aagaggtttt aagttacgat actttcacta   6360
atattttaat aaaaaactaa aactaacaag taatatataat tgatgaaaaa aatgtctttt   6420
atacatacgg aaaaataagg atgaaatgta ttttttttc ttttttttgtt aaaatataaa   6480 atatcgtgaa aataaaatga cattattaca cctaagagta aatgataaaa tatttcttaa   6540
tcgaataatc cataatttca tcattgataa aaataaatta tcatgttatt tacttatata   6600
ttttttgttt aatcttttgt gcagctatcc atatttagta ttttagcaca tgaatggcag   6660
aaagtaaata tttatttata caacaagatt gtaatttata ataaataaat attttaagta   6720
tataaattat attataatta aattttctaa tataatttt ttaacatata aattacattt   6780
taaatttatg aaaaataatt tatgttagga tgtattatta ttttaaataa ttgatgtttt   6840
cttttaaaaa tatttaaatt aagttagaaa caaggatgcc gtcaagtttt cttacagcct   6900
acatttatcg tgatgaagga aggaaggtgt tttaatggtc ccctgatgat gaaacttgga   6960 atgtaattt ataataaaca acggacataa ttgctccctc catattaata tctgtttgcc   7020
acacaactca gtcccatcat tatttggcgt tgacttcttc atcttatacc aagatagcaa   7080
gagtccatgg attcattttt tattattaat tattaattat ataaaatttt atttatattt   7140
attatccatt tgactattga gttttaagat attaggtttt tttcattaaa atataataaa   7200
tatattttta attaatatga taatctcaaa gtaaaaaaat tattatattt attattaaga   7260
atttttcatt gaaagtttaa aatattgtta acaactaaaa atttcacttt caattaattt   7320
aattaattta ataatgtcat ccacatgtga attatttata tatataattt aataaataag   7380
attaattatt tttcttcaat aaagacggtt atggatacat taatctgtct ccattattat   7440
tatcttattt cattataatc ttatgattaa aaataaaata gattaaaatt ataaaagaat   7500
tgattagtat tattattata atttctatca tatagcaagt gtttaatttt aatccagatc   7560
tatcaagtta acaatttaat aataaataaa taataatatt tttatcaaaa ttaataatat   7620
gatggattag atcttaaaca tacatattta attctagcaa tacacacata tatatatata   7680
tatatatata tatatata tatatatata tatatatata tatataattt tacatttta   7740 cttatggttt atctaaaaat aataaaataa atctatgatc ttatagttta tattataaat   7800
agctttcttt attaattaat aatattttt ataatataga gctatttttt catttgttaa   7860
acccatgttt gtttgaattt ttattcaaat ttttctatga tttttttcta caaattgtta   7920
taattttgat agagaaaaat atgattatct tctttaagtt cattaaaaaa tccatagatt   7980
```

```
tttttccctg tatcctcaca caaatatttt gtatataaac aaacaaacta aatgtttcag    8040 gttcatttttt tcacacaaaa aaatggaaat gaaatttttta attttttcaga caaaagtaaa    8100 aaaaaaaatt atactatata aaaaatattt tggttcctcc aatattttttt ttctcaaagt    8160 tccgccactg atttcatgcg tctctatgtc taatatcaag ttcctctctt tttctttgtc    8220 ttttttattaa ctaaattcag tattaagaca gtaactgatt tatgactaat ctatctattt    8280
gttataatgt aatcgccagc tatgaaactg acatattagc cttttgtatg caatatccta    8340
ttttgcatgc acagcttttg gagtctgcaa gtactgaatc atctcttagt ctcatagata    8400
gcccactaca agtgatatgg cttgactcac ggcggatccc aaagtcgtgc ttcagtaact    8460
tgacggaatt gactgtgcac ggatgccaat ttttaacaga tgttgtcata cccttctatt    8520
tacttccttt cttaactaat ttgcaacaat tacaagtctc ggactgtcgt tctgtgaaaa    8580
gcatatttga cgtgaaaaca gctatgggat tgggagcagc agccttccct agacctctcc    8640
ctttttccct caagaaattg actttagagt ggctgccaaa actggagaat gtctggaatg    8700
aagatcctca tggaattcta accatgcaac ttctacaaca tgtaaaggtt aaaaattgta    8760
aatgccttac aagtgtgttt ccggcatcat tagccaaaga tcttgaaaaa ctagttgtca    8820
aagactgtga gggattgata gaaattgttg cagaggataa tgcagatcca agagaagcaa    8880
atctggagct tacgttccct tgtccctgtg tgagctcatt gaaactacaa ggtttgccca    8940
agttcaagta ttttttactac tgctcactgc agtgtgacat gttccagaca cctaccaagg    9000
atgaaatggt actattgtgt tactactttg tccttactgc ataatctcat gcctgcaaat    9060
taaatataat tgcactactt cattttttatt gttcaacatg agtgatatga acattctctt    9120
caaattaaaa tgtgagaatt tcacgtacat tgctatatat atatgccgtg ttctatcttc    9180
tatacctatt aactcccatt tttcatgttt tacataaata agtaaaagaa tacacttaag    9240
ggtacatgtt gcattcatga cacaacaatg acatttttagg tttgagcttt attcttatta    9300
atacagacaa ttacatagaa tcttacacat gccatttttac tttatcaaat acaatgtatg    9360 gatggtttttc aaatctttat aaacaatctc cctaccatat aaaggatcga attttttcatc    9420 atttttcttct ccgttggaac cactactacc tcccttaagg tctcctttat cacctttttcc    9480 atctaaaatt ttaaactaca aataaataaa tttgtttagg cacaaaccgt atcaaaatcc    9540
cttccacctt attaatagct agctagccag gttcatctct tttataaccct cactaacctg    9600 ctttttgcttg gttatcggtt tctcttggta gcctacatcc aacttacagt gcctgtcact    9660
cggtgaaaaa ggactggaga tgatcaagcg tgcagaattt cagagaaact tcttacacaa    9720
gttacaagtt cttactctgt gctttcatat tgggtcgaat gtatttccat atgaaattct    9780
acaactggcg cccaatatag agaagcttgt ggtgtgtgat ggttccttca aggagatttt    9840
ctgctttgat agtcttaatg tggatgaggc tggactccta ttacagctca agtcttatg    9900 cttggagtcc cttccagagc ttgttttccat tgggttagag aactcttgga ttcagccctt    9960
actgggaaat ctagaaacct tggaagtaat aggttgttct agtttaaaag acttggtacc    10020
atctacagtg tcttttttcca atctgacata tttggaagta gaaagatgcc attgcctgct    10080
atatttgttc acatcctcca cagcaagaag tttgggtcaa ctcaaaagaa tggagataaa    10140
atggtgtggt tcaattgaag aggtagtagt ctctaaggag ggggatgaat cacatgagga    10200
ggagattata tttccgcagc tcaattgttt gaaacttgaa tatttatcaa agctgagaag    10260
cttctataaa ggaagtttat taagtttccc atcattggag gaattgtcag taatccgttg    10320
```

```
cgagtggatg gaaacattat gtccaggtac ccttaaagca gacaagttgg ttcaagttca    10380
acttaaggag agttattctt ggaggcactc agatcctatc aaattggaaa atgacctgaa    10440
ctctaccatg cgggaggcat tttggaaaaa ggtatgtttt caattatttt gattaaatat    10500
gattgatatt ggtgtatgtt gttcttataa tgcaaaatat acaccgttag gttgattaga    10560
ttcatcttca aattaacttg ggcctcatcc aatttatctt ggattttcag cgtcgtccaa    10620 ttttcggaa  aaccaaaaaa ctcacagaaa caacatttat gtgccaatcc aatttggcta    10680
atattaattt tttacgttaa actcataata tttaataat  ttaatttatt ttctatgtac    10740
tttatcaatg ctacttaact tttatatata ttaataatat aaaatgaatc caaactcttt    10800
caagtcattg taaaaatgat ttgaaaatta tttaattttt attttattta tattaatcct    10860
attaaataaa agaaactatc aatcttttgt aatccaatct tatatacata ttcaaaatat    10920
ttatctttta gcaattttaa ctatataaaa aaattatctt ctaggattaa gatactatat    10980
aattatattt aaaatctaga ttaggtagtt aaaatgttag ttgttcattt ttttttaatt    11040
ttctttaact ttttgttatt tcttcattta tacataaaaa taaattaaat aaatattaaa    11100
aaaattagag tgacttgaag aagtttagat tcactgtata ttattattat tattaattac    11160
taatacaaat aaaagttaag tagtataagt aaggtatata aaaaataatt atttaaatat    11220
tagtgagttt agcttactaa aaaattaaga gattcttttt ttagtataag gtaagaggtt    11280
aatataagtc aaataatttt gtttgtcaac ttaattgtat gacgtgactg caagctcaat    11340
ctaatggtat atattgtgtt ggagagaaaa gtatgttcaa gagcatctgg atcttatatt    11400
ttaacggaga ttaaatgtgt tgtatttatt agtattcatt gcatatatga atttttttata    11460 agaaatggtc attaaatttg tgcgattttc ttataaataa ctcaccagtt gagactaata    11520
aatatgctaa attttttctta attttttctaa gtaagataaa aaaatactcg atcgactatc    11580
tagctttgat catgcgtatg ttttgtcaaa tgatgaattt tgaattttga aaaataacct    11640
actctttctt atacaaatat ctagaaactt ttttatgagt gcaacaaaga catataaaaa    11700
atattctgga aaatactttc attgtgtgtt gataaattta gaatgaatgt accagaatca    11760
actagttgaa aactattatc tcaggcgcat tcatccagaa atcaactcaa ggaggagctg    11820
attttttttc ctttacaaat tatttaaata attttgaagg cagattttga ttagagagca    11880
tccacgatta acggaaatct ggactataat cagaaatttg ttactttttt aatttattgt    11940
tttaaaaata attacacttt aaaaattgag agcacattag ttatttggtg cgattgggga    12000
tgcatttctt cctacagaat aatactactc ttttttttta ttcttttacg tttgcagtta    12060
tggaagtctg cagatacgga attcagtatt gacctcaaag atagcccagt acaagagata    12120
tggcttaggc ttcactcact gcatatcccc ccacacttct gcttccctaa gttacacacc    12180
ttgattgtgg acggctgcca tttttatca  gatgcggtct tacccttctc tttacttcct    12240
ttattaccta atttgaaaac attggaagtt cgaaactgtg attttgtgaa atcatatttt    12300
gatgtgacaa ctatgggacc actcccttt  gccctcaaga cattggcact gtgtgatctg    12360
ccaaatctgg agaatgtttg gaattcaaat gttgagctta cgttcccca  agtcaagtca    12420 ttggcactct gtgatctgcc aaagttaaag tatgacatct tgaagccatt tacacatcta    12480
gaaccacata ctctaaaatca agtctgtatt caaaaggtat cattactact tctatatata    12540
tgaactaaat tgccatcatt agtgttcttt actacttcta tatatatgaa ctaaattgcc    12600
atcattagtg ttctttacta cttctatata tatgaacaaa ttgccatcct gttaaaatta    12660
aaaagttgtg aacctttccc ttatacagtt atatatgcta tgttgagtct tctatccatc    12720
```

-continued

```
ttctacgcat attggcttcc attttttctat tttttattta tctacataag tcagataata    12780
cggctacagc tactattcaa tattgatcat gatgaattta taatgaaaca tgttgcattc    12840
atgatgtgaa acagcatttg aggtgcgatc cttattctca ttatttttctt ctacaacctt    12900
actaataatc tcatctatca cttttcccat cttaaaatat taagtcgac atacggtgtg    12960
aatatccttt ctccaccttta ttcttttat ggtatccttt tccaccttat aaatagctag    13020
cctagttcgt cttttttct tttttggttt ttaagtaaac tgatttcttt taaattgact    13080
tgtttgcacc tatttaattg aattggttaa tttgtcatta attattggac ttattttagc    13140
gtgaaagttc attatttcaa ttatataaaa agagctggat ctataacttc cctaacctgc    13200
tttttcttca ttgttggttt ctcttggtag cttacaccca acatagagca cctgacactc    13260
ggtgaacatg aactcaacat gattttgagt ggagaattcc agggaaacca cttaaacgag    13320
ttaaaagtgc ttgctctgtt ctttcatatt gaatccgatg tatttctaca acgggtgccc    13380
aatatagaga agcttgaggt gcgtgatgg tccttcaaag agattttctg ctttgatagc    13440
cttaatgtgg atgaggatgg attggtttca cagctgaaag tgatatgccc ggactcccctt    13500
ccagagcttg tttccattgg gtcagagaac tctgggattg tgccctttct cagaaatcta    13560
gaaacattgc aagtaatcag ctgtttcagt tcaataaatc tggtaccatg cacagtgtct    13620
ttttccaatc tgacatattt gaaagtagaa agttgcaaga gtctgctata tttgttcaca    13680
tcctcaacag caagaagttt gggtcaactc aaaacaatgg agataagttg gtgtaattca    13740
attgaagaga tagtgtcttc aacagaggaa ggggatgaat cagatgagaa tgagataata    13800
tttcagcagc tcaattgttt gaaacttgaa ttttatttta agctgagaag gttctacaaa    13860
gggagtttaa gtttcccgtc cttggaggaa ttcacagtat ggcgttgcga gaggatggaa    13920
agtttgtgtg caggtacagt caaaacagac aagctgttac aagtgaatac taattggggc    13980
ggagatgtta tcccattgga aactgatctg aactctgcca tgcaaaaccg atag         14034
```

<210> SEQ ID NO 2
<211> LENGTH: 2463
<212> TYPE: PRT
<213> ORGANISM: Glycine max

<400> SEQUENCE: 2

```
Met Asp Ala Val Ser Ser Ala Leu Leu Glu Pro Val Thr Asn Ser Val
1               5                  10                  15

Leu Asp Leu Leu Lys Lys Gln Val Asp Tyr Ile Arg Tyr Arg Arg Asn
            20                  25                  30

Phe Asp Glu Leu Asp Glu Cys Val Lys Gln Leu Lys His Lys Lys Glu
        35                  40                  45

Ile Val Asp His Gln Cys Glu Glu Ala Val Lys Asn Gly His Glu Ile
    50                  55                  60

Glu Gly Lys Val Arg Glu Trp Leu Gly Lys Val Gly Lys Phe Glu Thr
65                  70                  75                  80

Glu Val Glu Lys Tyr Trp Asn Asp Asp Gly His Lys Lys Thr Arg Phe
                85                  90                  95

Ser Asn Tyr Leu Phe Pro Tyr Phe Arg His Arg Leu Gly Arg Leu Ala
            100                 105                 110

Lys Lys Met Ala Val Glu Gly Lys Lys Ile Thr Asp Asp Cys Pro Lys
        115                 120                 125

Ser Asp Glu Ile Ala Tyr Arg Val Tyr Val Thr Ser Asn Tyr Ala Ile
    130                 135                 140
```

```
Leu Ser Asn Asn Asp Leu Met Asp Phe Gly Ser Arg Lys Ser Ile Met
145                 150                 155                 160

Glu Gln Ile Met Ala Thr Leu Val Glu Asp Pro Thr Val Lys Met Ile
            165                 170                 175

Gly Val Tyr Gly Arg Ser Gly Val Gly Lys Ser Thr Leu Ile Lys Ala
        180                 185                 190

Ile Ala Lys Ile Ala Arg Asp Lys Lys Leu Phe Asn Val Val Ala Phe
        195                 200                 205

Ser Glu Ile Thr Asp Asn Pro Asn Leu Lys Gln Val Gln Glu Asp Ile
        210                 215                 220

Ala Tyr Pro Leu Gly Leu Lys Leu Glu Gly Gly Glu Asn Val Arg
225                 230                 235                 240

Ala Asp His Leu Arg Arg Arg Leu Lys Lys Glu Lys Glu Asn Thr Leu
            245                 250                 255

Ile Ile Leu Asp Asp Leu Trp Asp Arg Leu Asp Leu Asn Arg Leu Gly
            260                 265                 270

Ile Pro Leu Asp Gly Asp Val Asp Asp Lys Gln Gly Pro Lys Gly Pro
            275                 280                 285

Thr Lys Glu Lys Ser Leu Ala Asp Tyr Lys Gly Cys Lys Ile Leu Leu
290                 295                 300

Thr Ser Arg Lys Arg Asn Val Leu Thr Asp Lys Met Glu Val Lys Leu
305                 310                 315                 320

Thr Phe Cys Val Glu Glu Leu Asp Glu Lys Asp Ala Leu Lys Leu Phe
            325                 330                 335

Arg Lys Glu Ala Ala Ile Gln Gly Glu Met Ser Lys Ser Lys Lys Glu
            340                 345                 350

Ile Val Lys Lys Tyr Cys Ala Gly Leu Pro Met Ala Ile Val Thr Val
            355                 360                 365

Gly Arg Ala Leu Arg Asp Lys Ser Asp Ser Glu Trp Glu Lys Leu Lys
            370                 375                 380

Asn Gln Glu Leu Val Gly Val Gln Asn Pro Met Glu Ile Ser Val Lys
385                 390                 395                 400

Met Ser Tyr Asp His Leu Glu Asn Glu Leu Lys Ser Ile Phe Phe
                405                 410                 415

Leu Cys Ala Gln Met Gly His Gln Pro Leu Ile Met Asp Leu Val Lys
            420                 425                 430

Tyr Cys Phe Gly Leu Gly Ile Leu Glu Gly Val Tyr Ser Leu Gly Glu
        435                 440                 445

Ala Arg Asp Arg Ile Ser Thr Ser Ile Lys Lys Leu Lys Asp Ser Gly
        450                 455                 460

Leu Val Leu Asp Gly Ser Ser Ser Ile His Phe Asn Met His Asp Leu
465                 470                 475                 480

Val Arg Asp Ala Ala Leu Ser Ile Ala Gln Asn Glu Gln Asn Val Phe
            485                 490                 495

Thr Leu Arg Asn Gly Lys Leu Asn Asp Trp Pro Glu Leu Lys Arg Cys
        500                 505                 510

Thr Ser Ile Ser Ile Cys Asn Ser Asp Ile Ile Asp Glu Leu Pro Asn
        515                 520                 525

Val Met Asn Cys Pro Gln Leu Lys Phe Phe Gln Ile Asp Asn Asp Asp
        530                 535                 540

Pro Ser Leu Lys Ile Pro Glu Ser Phe Phe Lys Arg Met Lys Lys Leu
545                 550                 555                 560
```

```
Arg Val Leu Ile Leu Thr Gly Phe His Leu Ser Ser Leu Pro Ser Ser
                565                 570                 575
Ile Lys Cys Leu Ser Asp Leu Arg Leu Leu Cys Leu Glu Arg Cys Thr
            580                 585                 590
Leu Asp His Asn Leu Ser Ile Ile Gly Lys Leu Lys Lys Leu Arg Ile
            595                 600                 605
Leu Ser Phe Ser Gly Ser Arg Ile Glu Asn Leu Pro Ala Glu Leu Lys
            610                 615                 620
Asp Leu Asp Lys Leu Gln Leu Leu Asp Ile Ser Asn Cys Ser Ile Val
625                 630                 635                 640
Thr Met Ile Pro Pro Asn Leu Ile Ser Arg Leu Thr Ser Leu Glu Glu
                645                 650                 655
Leu Tyr Val Arg Lys Cys Phe Met Glu Val Ser Glu Glu Gly Glu Arg
                660                 665                 670
Asn Gln Ser Gln Asn Ser Phe Ile Ser Glu Leu Lys His Leu His Gln
            675                 680                 685
Leu Gln Val Val Asp Leu Ser Ile Pro Cys Ala Glu Phe Phe Ala Lys
            690                 695                 700
Glu Leu Phe Phe Asp Asn Leu Ser Asp Tyr Lys Ile Glu Ile Gly Asn
705                 710                 715                 720
Phe Lys Thr Leu Ser Ala Gly Asp Phe Arg Met Pro Asn Lys Tyr Glu
                725                 730                 735
Asn Phe Lys Ser Leu Ala Leu Glu Leu Lys Asp Asp Thr Asp Asn Ile
            740                 745                 750
His Ser Gln Thr Gly Ile Lys Leu Leu Phe Glu Thr Val Glu Asn Leu
            755                 760                 765
Leu Leu Gly Glu Leu Asn Gly Val Gln Asp Val Val Asn Glu Leu Asn
            770                 775                 780
Leu Asn Gly Phe Pro His Leu Lys His Phe Ser Ile Val Asn Asn Pro
785                 790                 795                 800
Ser Ile Lys Tyr Ile Ile Asn Ser Lys Asp Leu Phe Tyr Pro Gln Asp
                805                 810                 815
Val Phe Pro Lys Leu Glu Ser Leu Cys Leu Tyr Lys Leu Lys Glu Ile
                820                 825                 830
Glu Met Ile Tyr Phe Ser Ser Gly Thr Glu Met Ile Cys Phe Ser Pro
            835                 840                 845
Phe Thr Asp Cys Ser Phe Thr Lys Leu Lys Thr Ile Lys Val Glu Lys
            850                 855                 860
Cys Asp Gln Leu Lys Asn Leu Phe Ser Phe Cys Met Val Lys Leu Leu
865                 870                 875                 880
Ala Ser Leu Glu Thr Ile Gly Val Ser Asn Cys Gly Ser Leu Glu Glu
                885                 890                 895
Ile Ile Lys Ile Pro Asp Asn Ser Asp Lys Ile Glu Phe Leu Lys Leu
                900                 905                 910
Met Ser Leu Ser Leu Glu Ser Leu Ser Ser Phe Thr Ser Phe Tyr Thr
            915                 920                 925
Thr Val Glu Gly Ser Ser Thr Asn Arg Asp Gln Ile Gln Ile Thr Val
            930                 935                 940
Met Thr Pro Pro Leu Phe Gly Glu Leu Val Glu Ile Pro Asn Leu Glu
945                 950                 955                 960
Asn Leu Asn Leu Ile Ser Met Asn Lys Ile Gln Lys Ile Trp Ser Asp
                965                 970                 975
Gln Pro Pro Ser Asn Phe Cys Phe Gln Asn Leu Ile Lys Leu Val Val
```

-continued

```
            980             985             990
Lys Asp Cys Gln Asn Leu Arg Tyr  Leu Cys Ser Leu Ser  Val Ala Ser
            995            1000            1005

Ser Leu  Arg Lys Leu Lys Gly  Leu Phe Val Ser Asn  Cys Lys Met
        1010            1015            1020

Met Glu  Lys Ile Phe Ser Thr  Glu Gly Asn Ser Ala  Asp Lys Val
        1025            1030            1035

Cys Val  Phe Pro Lys Leu Glu  Glu Ile His Leu Asp  Gln Met Asp
        1040            1045            1050

Glu Leu  Thr Asp Ile Trp Gln  Ala Glu Val Ser Ala  Asp Ser Phe
        1055            1060            1065

Ser Ser  Leu Thr Ser Val Asn  Ile Arg Ser Cys His  Lys Leu Asp
        1070            1075            1080

Lys Ile  Phe Pro Ser His Met  Glu Gly Trp Phe Ala  Ser Leu Asn
        1085            1090            1095

Ser Leu  Lys Val Ser Phe Cys  Glu Ser Val Glu Val  Ile Phe Glu
        1100            1105            1110

Ile Lys  Asp Ser Gln Gln Val  Asp Ala Ser Gly Gly  Ile Asp Thr
        1115            1120            1125

Asn Leu  Gln Val Val Tyr Val  Ser Glu Leu Pro Lys  Leu Glu Gln
        1130            1135            1140

Val Trp  Ser Arg Asp Pro Gly  Gly Ile Leu Asn Phe  Lys Lys Leu
        1145            1150            1155

Gln Ser  Ile Glu Met Asp Asp  Cys Glu Arg Leu Arg  Asn Val Phe
        1160            1165            1170

Pro Ala  Ser Val Gly Lys Asp  Val Pro Lys Leu Glu  Tyr Met Ser
        1175            1180            1185

Val Ile  Glu Cys Asp Gly Ile  Val Glu Ile Val Ala  Cys Glu Asp
        1190            1195            1200

Gly Ser  Glu Thr Asn Thr Glu  Gln Leu Val Phe Pro  Glu Leu Thr
        1205            1210            1215

Asp Met  Glu Leu Cys Tyr Leu  Ser Ser Ile Gln His  Phe Tyr Arg
        1220            1225            1230

Gly Arg  His Pro Ile Glu Cys  Pro Lys Leu Lys Lys  Leu Ser Val
        1235            1240            1245

Gly Lys  Cys Asn Glu Lys Leu  Lys Thr Phe Gly Thr  Gly Glu Arg
        1250            1255            1260

Ser Asn  Glu Glu Asp Glu Ala  Val Met Ser Ala Glu  Lys Ile Phe
        1265            1270            1275

Pro Asn  Leu Glu Tyr Leu Asp  Ile His Phe Asp Glu  Ala Gln Lys
        1280            1285            1290

Trp Leu  Leu Ser Asn Thr Val  Lys His Arg Met His  Arg Leu Lys
        1295            1300            1305

Lys Leu  Arg Leu Ser Glu Val  Asn Asp Gly Glu Arg  Leu Cys Gln
        1310            1315            1320

Ile Leu  Tyr Arg Met Pro Asn  Leu Glu Lys Leu Tyr  Leu Pro Met
        1325            1330            1335

Ala Lys  His Leu Leu Lys Glu  Ser Ser Glu Ser Arg  Leu Gly Thr
        1340            1345            1350

Leu Leu  Gln Leu Lys Glu Leu  Asp Leu Trp Arg Ser  Glu Ile Lys
        1355            1360            1365

Asp Ile  Gly Phe Glu Arg Glu  Pro Val Leu Gln Arg  Leu Glu Leu
        1370            1375            1380
```

-continued

Leu Ser Leu Phe Lys Cys His Lys Leu Arg Asn Leu Gly Pro Pro
    1385            1390                1395

Ser Val Ser Leu Ala Tyr Leu Thr Asn Leu Lys Val Glu Tyr Cys
    1400            1405                1410

Tyr Gly Leu Arg Asn Leu Met Ala Ser Ser Thr Ala Lys Ser Leu
    1415            1420                1425

Val Gln Leu Lys Ser Met Lys Ile Arg Lys Cys Cys Lys Leu Glu
    1430            1435                1440

Glu Ile Val Ser Asp Glu Gly Asn Glu Glu Glu Gln Ile Val
    1445            1450                1455

Phe Gly Lys Leu Ile Thr Ile Glu Leu Glu Gly Leu Lys Lys Leu
    1460            1465                1470

Lys Ser Phe Cys Ser Ser Lys Asn Tyr Glu Phe Lys Phe Pro Ser
    1475            1480                1485

Leu Glu Gly Leu Ile Val Arg Lys Cys Pro Met Met His Thr Phe
    1490            1495                1500

Thr Glu Gly Asp Ala Arg Ala Pro Lys Leu Glu Asn Thr Val Thr
    1505            1510                1515

Ala Lys Glu Glu Gly Lys Glu Glu Ala Lys Trp Gln Trp Glu Gly
    1520            1525                1530

Asp Leu Asn Ser Thr Ile Gln Lys Gly Phe Asn Lys Leu Leu Glu
    1535            1540                1545

Ser Ala Ser Thr Glu Ser Ser Leu Ser Leu Ile Asp Ser Pro Leu
    1550            1555                1560

Gln Val Ile Trp Leu Asp Ser Arg Arg Ile Pro Lys Ser Cys Phe
    1565            1570                1575

Ser Asn Leu Thr Glu Leu Thr Val His Gly Cys Gln Phe Leu Thr
    1580            1585                1590

Asp Val Val Ile Pro Phe Tyr Leu Leu Pro Phe Leu Thr Asn Leu
    1595            1600                1605

Gln Gln Leu Gln Val Ser Asp Cys Arg Ser Val Lys Ser Ile Phe
    1610            1615                1620

Asp Val Lys Thr Ala Met Gly Leu Gly Ala Ala Ala Phe Pro Arg
    1625            1630                1635

Pro Leu Pro Phe Ser Leu Lys Lys Leu Thr Leu Glu Trp Leu Pro
    1640            1645                1650

Lys Leu Glu Asn Val Trp Asn Glu Asp Pro His Gly Ile Leu Thr
    1655            1660                1665

Met Gln Leu Leu Gln His Val Lys Val Lys Asn Cys Lys Cys Leu
    1670            1675                1680

Thr Ser Val Phe Pro Ala Ser Leu Ala Lys Asp Leu Glu Lys Leu
    1685            1690                1695

Val Val Lys Asp Cys Glu Gly Leu Ile Glu Ile Val Ala Glu Asp
    1700            1705                1710

Asn Ala Asp Pro Arg Glu Ala Asn Leu Glu Leu Thr Phe Pro Cys
    1715            1720                1725

Pro Cys Val Ser Ser Leu Lys Leu Gln Gly Leu Pro Lys Phe Lys
    1730            1735                1740

Tyr Phe Tyr Tyr Cys Ser Leu Gln Cys Asp Met Phe Gln Thr Pro
    1745            1750                1755

Thr Lys Asp Glu Met Pro Thr Ser Asn Leu Gln Cys Leu Ser Leu
    1760            1765                1770

-continued

```
Gly Glu Lys Gly Leu Glu Met Ile Lys Arg Ala Glu Phe Gln Arg
    1775                1780                1785

Asn Phe Leu His Lys Leu Gln Val Leu Thr Leu Cys Phe His Ile
    1790                1795                1800

Gly Ser Asn Val Phe Pro Tyr Glu Ile Leu Gln Leu Ala Pro Asn
    1805                1810                1815

Ile Glu Lys Leu Val Val Cys Asp Gly Ser Phe Lys Glu Ile Phe
    1820                1825                1830

Cys Phe Asp Ser Leu Asn Val Asp Glu Ala Gly Leu Leu Leu Gln
    1835                1840                1845

Leu Lys Val Leu Cys Leu Glu Ser Leu Pro Glu Leu Val Ser Ile
    1850                1855                1860

Gly Leu Glu Asn Ser Trp Ile Gln Pro Leu Leu Gly Asn Leu Glu
    1865                1870                1875

Thr Leu Glu Val Ile Gly Cys Ser Ser Leu Lys Asp Leu Val Pro
    1880                1885                1890

Ser Thr Val Ser Phe Ser Asn Leu Thr Tyr Leu Glu Val Glu Arg
    1895                1900                1905

Cys His Cys Leu Leu Tyr Leu Phe Thr Ser Ser Thr Ala Arg Ser
    1910                1915                1920

Leu Gly Gln Leu Lys Arg Met Glu Ile Lys Trp Cys Gly Ser Ile
    1925                1930                1935

Glu Glu Val Val Val Ser Lys Glu Gly Asp Glu Ser His Glu Glu
    1940                1945                1950

Glu Ile Ile Phe Pro Gln Leu Asn Cys Leu Lys Leu Glu Tyr Leu
    1955                1960                1965

Ser Lys Leu Arg Ser Phe Tyr Lys Gly Ser Leu Leu Ser Phe Pro
    1970                1975                1980

Ser Leu Glu Glu Leu Ser Val Ile Arg Cys Glu Trp Met Glu Thr
    1985                1990                1995

Leu Cys Pro Gly Thr Leu Lys Ala Asp Lys Leu Val Gln Val Gln
    2000                2005                2010

Leu Lys Glu Ser Tyr Ser Trp Arg His Ser Asp Pro Ile Lys Leu
    2015                2020                2025

Glu Asn Asp Leu Asn Ser Thr Met Arg Glu Ala Phe Trp Lys Lys
    2030                2035                2040

Leu Trp Lys Ser Ala Asp Thr Glu Phe Ser Ile Asp Leu Lys Asp
    2045                2050                2055

Ser Pro Val Gln Glu Ile Trp Leu Arg Leu His Ser Leu His Ile
    2060                2065                2070

Pro Pro His Phe Cys Phe Pro Lys Leu His Thr Leu Ile Val Asp
    2075                2080                2085

Gly Cys His Phe Leu Ser Asp Ala Val Leu Pro Phe Ser Leu Leu
    2090                2095                2100

Pro Leu Leu Pro Asn Leu Lys Thr Leu Glu Val Arg Asn Cys Asp
    2105                2110                2115

Phe Val Lys Ile Ile Phe Asp Val Thr Thr Met Gly Pro Leu Pro
    2120                2125                2130

Phe Ala Leu Lys Thr Leu Ala Leu Cys Asp Leu Pro Asn Leu Glu
    2135                2140                2145

Asn Val Trp Asn Ser Asn Val Glu Leu Thr Phe Pro Gln Val Lys
    2150                2155                2160

Ser Leu Ala Leu Cys Asp Leu Pro Lys Leu Lys Tyr Asp Ile Leu
```

Lys Pro Phe Thr His Leu Glu Pro His Thr Leu Asn Gln Val Cys
2180                2185                2190

Ile Gln Lys Leu Thr Pro Asn Ile Glu His Leu Thr Leu Gly Glu
2195                2200                2205

His Glu Leu Asn Met Ile Leu Ser Gly Glu Phe Gln Gly Asn His
2210                2215                2220

Leu Asn Glu Leu Lys Val Leu Ala Leu Phe Phe His Ile Glu Ser
2225                2230                2235

Asp Val Phe Leu Gln Arg Val Pro Asn Ile Glu Lys Leu Glu Val
2240                2245                2250

Arg Asp Gly Ser Phe Lys Glu Ile Phe Cys Phe Asp Ser Leu Asn
2255                2260                2265

Val Asp Glu Asp Gly Leu Val Ser Gln Leu Lys Val Ile Cys Pro
2270                2275                2280

Asp Ser Leu Pro Glu Leu Val Ser Ile Gly Ser Glu Asn Ser Gly
2285                2290                2295

Ile Val Pro Phe Leu Arg Asn Leu Glu Thr Leu Gln Val Ile Ser
2300                2305                2310

Cys Phe Ser Ser Ile Asn Leu Val Pro Cys Thr Val Ser Phe Ser
2315                2320                2325

Asn Leu Thr Tyr Leu Lys Val Glu Ser Cys Lys Ser Leu Leu Tyr
2330                2335                2340

Leu Phe Thr Ser Ser Thr Ala Arg Ser Leu Gly Gln Leu Lys Thr
2345                2350                2355

Met Glu Ile Ser Trp Cys Asn Ser Ile Glu Glu Ile Val Ser Ser
2360                2365                2370

Thr Glu Glu Gly Asp Glu Ser Asp Glu Asn Glu Ile Ile Phe Gln
2375                2380                2385

Gln Leu Asn Cys Leu Lys Leu Glu Phe Leu Phe Lys Leu Arg Arg
2390                2395                2400

Phe Tyr Lys Gly Ser Leu Ser Phe Pro Ser Leu Glu Glu Phe Thr
2405                2410                2415

Val Trp Arg Cys Glu Arg Met Glu Ser Leu Cys Ala Gly Thr Val
2420                2425                2430

Lys Thr Asp Lys Leu Leu Gln Val Asn Thr Asn Trp Gly Gly Asp
2435                2440                2445

Val Ile Pro Leu Glu Thr Asp Leu Asn Ser Ala Met Gln Asn Arg
2450                2455                2460

<210> SEQ ID NO 3
<211> LENGTH: 2700
<212> TYPE: DNA
<213> ORGANISM: Glycine max

<400> SEQUENCE: 3
atggctgcaa aaacacgttc ccttgcatcc atctatgatg tgttcctcag cttcagaggt    60
ttagacacac gccatggttt cactgacaat ctctacaaag ctcttgatga caggggaatc   120
tacactttca ttgatgatca ggagtttccc agaggagacg aaataacacc tgcactttcc   180
aaggcaattc aagagtccag gattgctatt actgtgcttt ctcaaaacta tgcttcttcc   240
tcgttttgtt tagatgaact tgtaaccatc cttcactgca agagtgaagg ctgttggtt    300 ataccggtct tttataaggt agatccttct gatgtcagac accagaaagg tagttatgga   360

```
gaagcaatgg ctaagcatca gaagaggttc aaagctaaga aggagaagct gcagaaatgg    420
aggatggctt tgaaacaagt agctgacttg tctggctatc atttggaaga tgggtataaa    480
accatactaa tatattttac tttatggttt ttattggatt aggttttact tgtctattga    540
tttaactagt aaaattcaaa taggaaagaa atgttcttgt taaccttgac aattattgta    600
cctatcgaga catggatgca aggattttag gctgacttca tcagaacttt ttttgtttgt    660
ttgaaacaga gatgcatatg aatacgaatt tattgggagt attgttgagg aggtctgtag    720
gaagattagt cgtgcttctt tacatgctgc ggattatcca gttgatctag agtcacaagt    780
gacaaaggta atgaagcttt tgtatcttgg atcccatgat gttgtccaca tcatagggat    840
ccatggaatg ggcgggttag gaaaaacaac acttgctcgg gcagtttata atttgattgc    900
tctccatttt gatgaatcat gttttcttca aacgtgaga gaagaatcaa ataaacatgg     960
gttaaaacac cttcaaagca cccttctttc aaaattactt ggtgaaaagg acatcacctt   1020
aacaagttgg caagaaggag cttcaatgat acaacatagg ctccgaagaa agaagattct   1080
cttgatttta gatgatgttg acaaggacga gcaattaaag gctattgttg gaagacctga   1140
ttggtttggt cccggtagca gagtcatcat taccactcgg gacaaacatc tgctaaaatg   1200
tcacgaggtt gaaataactt tgaggtgaa tgatttgaat tacaaagctg taacaaaatg    1260
ggaatctgct gttttatatt tttataaaag aattcccagt gatgaaatcc aagagatact   1320
aaaagtaagc tttgatgctt tggaggaaga acaaaagaat gttttcttg atattgctta    1380 tttcttgaaa gggtataaat ggaaagaggt tgatgatata ctccgtgctc tttatggtaa   1440
ctgcaagaag catcatattg gggagttggt tgaaaaatct ctcataaagc ttaactgcta   1500
tgatggtggt actgttgaaa tgcacgacct gcttcaggac atgggtagag aaattgggcg   1560
gcagagatca ccagaagagc cctggaagtg caagagatta tggtcaccaa agatataat    1620 tcaagtttta aaacacaaca cggtgagtga gctcatgaat agttgaattt ttttgtcta    1680 tctcatattt acatcatggt taactttttc ttgataattt gtgaatttct ctaagcgagt   1740
caattgatat ttcacacaaa ttgtattgtg gttgattcgt gccttttgc attagcaggg    1800 aactagtaaa attgaaatca tatgtctgga ttgctccata tctgagaaag aagaaacagt   1860
ggaatggaat gaaaacgcct tcatgaagat ggaaaacctt aaaatactta ttattagaaa   1920
tgcaaatttt ccaaagctc ccagttattt tccagaaggt ttgagagtac tggaatggca    1980
cagatatcct tcaaattgtt taccatctaa ctttaatccg aacaaccttg ttatatgcaa   2040
cttacctgac agttccatga cgtcatttga gttccatggc tcatcgaagg catgtttaaa   2100
gagtatattt tcctcattgc atggctcatc gaaggcaagt ttaaagagta tattttcctc   2160
attccatgaa ttaaatttat tcatttgttt cttatttctt ttctttttc ttttttttg     2220 cctttgcaga agctggggca tctaacagtt ttgaattttg actggtgcaa attttaacc    2280 cagatacctg atgtatctga tcttccaaat ttgagggaac tttcatttcg atggtgtgag   2340
agtttagttg cagttgatga gtcaattggt tttctgaaga aacttaaaat attgaatgct   2400
gctggttgca ggaagcttac gagttttccg cctctcaact tgacctctct tgaaacactt   2460
gaactttctc actgttccag tcttgagtat tttccagaaa tattaggaga gatgaaaaac   2520
ataaaggcac ttcatttgga aggccttccc ataaagaat tgccatttc atttcaaaat     2580 cttattggac tccgtgagat aaccctgagg aggtgtagaa ttgttcggtt acgatgtagc   2640
ttagccatga tgcccaatct gtttcgattc caaattagaa attgcaacag ctggcaataa   2700
```

-continued

```
<210> SEQ ID NO 4
<211> LENGTH: 750
<212> TYPE: PRT
<213> ORGANISM: Glycine max

<400> SEQUENCE: 4
```

Met Ala Ala Lys Thr Arg Ser Leu Ala Ser Ile Tyr Asp Val Phe Leu
1               5                   10                  15

Ser Phe Arg Gly Leu Asp Thr Arg His Gly Phe Thr Asp Asn Leu Tyr
            20                  25                  30

Lys Ala Leu Asp Asp Arg Gly Ile Tyr Thr Phe Ile Asp Asp Gln Glu
        35                  40                  45

Phe Pro Arg Gly Asp Glu Ile Thr Pro Ala Leu Ser Lys Ala Ile Gln
    50                  55                  60

Glu Ser Arg Ile Ala Ile Thr Val Leu Ser Gln Asn Tyr Ala Ser Ser
65                  70                  75                  80

Ser Phe Cys Leu Asp Glu Leu Val Thr Ile Leu His Cys Lys Ser Glu
            85                  90                  95

Gly Leu Leu Val Ile Pro Val Phe Tyr Lys Val Asp Pro Ser Asp Val
            100                 105                 110

Arg His Gln Lys Gly Ser Tyr Gly Glu Ala Met Ala Lys His Gln Lys
        115                 120                 125

Arg Phe Lys Ala Lys Lys Glu Lys Leu Gln Lys Trp Arg Met Ala Leu
    130                 135                 140

Lys Gln Val Ala Asp Leu Ser Gly Tyr His Leu Glu Asp Gly Asp Ala
145                 150                 155                 160

Tyr Glu Tyr Glu Phe Ile Gly Ser Ile Val Glu Val Cys Arg Lys
                165                 170                 175

Ile Ser Arg Ala Ser Leu His Ala Ala Asp Tyr Pro Val Asp Leu Glu
        180                 185                 190

Ser Gln Val Thr Lys Val Met Lys Leu Leu Tyr Leu Gly Ser His Asp
    195                 200                 205

Val Val His Ile Ile Gly Ile His Gly Met Gly Gly Leu Gly Lys Thr
        210                 215                 220

Thr Leu Ala Arg Ala Val Tyr Asn Leu Ile Ala Leu His Phe Asp Glu
225                 230                 235                 240

Ser Cys Phe Leu Gln Asn Val Arg Glu Glu Ser Asn Lys His Gly Leu
            245                 250                 255

Lys His Leu Gln Ser Thr Leu Leu Ser Lys Leu Leu Gly Glu Lys Asp
        260                 265                 270

Ile Thr Leu Thr Ser Trp Gln Glu Gly Ala Ser Met Ile Gln His Arg
    275                 280                 285

Leu Arg Arg Lys Lys Ile Leu Leu Ile Leu Asp Asp Val Asp Lys Asp
    290                 295                 300

Glu Gln Leu Lys Ala Ile Val Gly Arg Pro Asp Trp Phe Gly Pro Gly
305                 310                 315                 320

Ser Arg Val Ile Ile Thr Thr Arg Asp Lys His Leu Leu Lys Cys His
            325                 330                 335

Glu Val Glu Ile Thr Phe Glu Val Asn Asp Leu Asn Tyr Lys Ala Val
        340                 345                 350

Thr Lys Trp Glu Ser Ala Val Leu Tyr Phe Tyr Lys Arg Ile Pro Ser
    355                 360                 365

Asp Glu Ile Gln Glu Ile Leu Lys Val Ser Phe Asp Ala Leu Glu Glu
    370                 375                 380

Glu Gln Lys Asn Val Phe Leu Asp Ile Ala Tyr Phe Leu Lys Gly Tyr
385                 390                 395                 400

Lys Trp Lys Glu Val Asp Asp Ile Leu Arg Ala Leu Tyr Gly Asn Cys
            405                 410                 415

Lys Lys His His Ile Gly Glu Leu Val Glu Lys Ser Leu Ile Lys Leu
        420                 425                 430

Asn Cys Tyr Asp Gly Gly Thr Val Glu Met His Asp Leu Leu Gln Asp
    435                 440                 445

Met Gly Arg Glu Ile Gly Arg Gln Arg Ser Pro Glu Pro Trp Lys
450                 455                 460

Cys Lys Arg Leu Trp Ser Pro Lys Asp Ile Ile Gln Val Leu Lys His
465                 470                 475                 480

Asn Thr Gly Thr Ser Lys Ile Glu Ile Ile Cys Leu Asp Cys Ser Ile
            485                 490                 495

Ser Glu Lys Glu Glu Thr Val Glu Trp Asn Glu Asn Ala Phe Met Lys
            500                 505                 510

Met Glu Asn Leu Lys Ile Leu Ile Ile Arg Asn Gly Lys Phe Ser Lys
            515                 520                 525

Ala Pro Ser Tyr Phe Pro Glu Gly Leu Arg Val Leu Glu Trp His Arg
530                 535                 540

Tyr Pro Ser Asn Cys Leu Pro Ser Asn Phe Asn Pro Asn Asn Leu Val
545                 550                 555                 560

Ile Cys Asn Leu Pro Asp Ser Ser Met Thr Ser Phe Glu Phe His Gly
            565                 570                 575

Ser Ser Lys Ala Cys Leu Lys Ser Ile Phe Ser Leu His Gly Ser
            580                 585                 590

Ser Lys Lys Leu Gly His Leu Thr Val Leu Asn Phe Asp Trp Cys Lys
            595                 600                 605

Phe Leu Thr Gln Ile Pro Asp Val Ser Asp Leu Pro Asn Leu Arg Glu
610                 615                 620

Leu Ser Phe Arg Trp Cys Glu Ser Leu Val Ala Val Asp Glu Ser Ile
625                 630                 635                 640

Gly Phe Leu Lys Lys Leu Lys Ile Leu Asn Ala Ala Gly Cys Arg Lys
            645                 650                 655

Leu Thr Ser Phe Pro Pro Leu Asn Leu Thr Ser Leu Glu Thr Leu Glu
            660                 665                 670

Leu Ser His Cys Ser Ser Leu Glu Tyr Phe Pro Glu Ile Leu Gly Glu
            675                 680                 685

Met Glu Asn Ile Lys Ala Leu His Leu Glu Gly Leu Pro Ile Lys Glu
            690                 695                 700

Leu Pro Phe Ser Phe Gln Asn Leu Ile Gly Leu Arg Glu Ile Thr Leu
705                 710                 715                 720

Arg Arg Cys Arg Ile Val Arg Leu Arg Cys Ser Leu Ala Met Met Pro
            725                 730                 735

Asn Leu Phe Arg Phe Gln Ile Arg Asn Cys Asn Ser Trp Gln
            740                 745                 750

<210> SEQ ID NO 5
<211> LENGTH: 2661
<212> TYPE: DNA
<213> ORGANISM: Glycine max

<400> SEQUENCE: 5
tgtcattgtt accatatgtc gtgttactct gcgtaataat aaacattttg tatgctatct    60

```
tttcatatt   tgttcaagtt   tgattctaca   ctcccaccat   atcaaccata   atcatactaa    120
acttttttct  tctaataatg   gctgcaaaaa   cacgttccct   tgcatccatc   tatgatgtgt    180
tcctcagctt  cagaggttta   gacacacgcc   atggtttcac   tgacaatctc   tacaaagctc    240
ttgatgacag  gggaatctac   actttcattg   atgatcagga   gtttcccaga   ggagacgaaa    300
taacacctgc  actttccaag   gcaattcaag   agtccaggat   tgctattact   gtgctttctc    360
aaaactatgc  ttcttcctcg   ttttgtttag   atgaacttgt   aaccatcctt   cactgcaaga    420
gtgaagggct  gttggttata   ccggtctttt   ataaggtaga   tccttctgat   gtcagacacc    480
agaaaggtag  ttatggagaa   gcaatggcta   agcatcagaa   gaggttcaaa   gctaagaagg    540
agaagctgca  gaaatggagg   atggctttga   aacaagtagc   tgacttgtct   ggctatcatt    600
tggaagatgg  agatgcatat   gaatacgaat   ttattgggag   tattgttgag   gaggtctgta    660
ggaagattag  tcgtgcttct   ttacatgctg   cggattatcc   agttgatcta   gagtcacaag    720
tgacaaaggt  aatgaagctt   ttgtatcttg   atcccatgga   tgttgtccac   atcataggga    780
tccatggaat  gggcgggtta   ggaaaaacaa   cacttgctcg   ggcagtttat   aatttgattg    840
ctctccattt  tgatgaatca   tgttttcttc   aaaacgtgag   agaagaatca   aataaacatg    900
ggttaaaaca  ccttcaaagc   acccttcttt   caaaattact   tggtgaaaag   gacatcacct    960
taacaagttg  gcaagaagga   gcttcaatga   tacaacatag   gctccgaaga   aagaagattc   1020
tcttgatttt  agatgatgtt   gacaaggacg   agcaattaaa   ggctattgtt   ggaagacctg   1080
attggtttgg  tcccggtagc   agagtcatca   ttaccactcg   ggacaaacat   ctgctaaaat   1140
gtcacgaggt  tgaaataact   tttgaggtga   atgatttgaa   ttacaaagct   gtaacaaaat   1200
gggaatctgc  tgttttatat   ttttataaaa   gaattcccag   tgatgaaatc   caagagatac   1260
taaaagtaag  ctttgatgct   ttggaggaag   aacaaaagaa   tgtttttctt   gatattgctt   1320
atttcttgaa  agggtataaa   tggaaagagg   ttgatgatat   actccgtgct   ctttatggta   1380
actgcaagaa  gcatcatatt   ggggagttgg   ttgaaaaatc   tctcataaag   cttaactgct   1440
atgatggtgg  tactgttgaa   atgcacgacc   tgcttcagga   catgggtaga   gaaattgggc   1500
ggcagagatc  accagaagag   ccctggaagt   gcaagagatt   atggtcacca   aaagatataa   1560
ttcaagtttt  aaaacacaac   acgggaacta   gtaaaattga   aatcatatgt   ctggattgct   1620
ccatatctga  gaaagaagaa   acagtggaat   ggaatgaaaa   cgccttcatg   aagatggaaa   1680
accttaaaat  acttattatt   agaaatggca   aattttccaa   agctcccagt   tattttccag   1740
aaggtttgag  agtactggaa   tggcacagat   atccttcaaa   ttgtttacca   tctaacttta   1800
atccgaacaa  ccttgttata   tgcaacttac   ctgacagttc   catgacgtca   tttgagttcc   1860
atggctcatc  gaaggcatgt   ttaaagagta   tattttcctc   attgcatggc   tcatcgaaga   1920
agctggggca  tctaacagtt   tgaattttg   actggtgcaa   attttaacc    cagatacctg   1980 atgtatctga  tcttccaaat   ttgagggaac   tttcatttcg   atggtgtgag   agtttagttg   2040
cagttgatga  gtcaattggt   tttctgaaga   aacttaaaat   attgaatgct   gctggttgca   2100
ggaagcttac  gagttttccg   cctctcaact   tgacctctct   tgaaacactt   gaactttctc   2160
actgttccag  tcttgagtat   tttccagaaa   tattaggaga   gatggaaaac   ataaaggcac   2220
ttcatttgga  aggccttccc   ataaaagaat   tgccattttc   atttcaaaat   cttattggac   2280
tccgtgagat  aaccctgagg   aggtgtagaa   ttgttcggtt   acgatgtagc   ttagccatga   2340
tgcccaatct  gtttcgattc   caaattagaa   attgcaacag   ctggcaataa   gtagaatcgg   2400
aagcaggtga  agaaaaagtc   cctccttcct   acaaaccata   gctttgggga   cacgcaagtt   2460
```

-continued

| | |
|---|---|
| ttccgtagct tttttcttat tttttttcatg tttttttattt tattattttg gtttcagttg | 2520 |
| tcaaaaattc acttaaccca actgatgttc accctatctt catcacgtac ttttgattca | 2580 |
| tttatattca tctttcacga ctttatgcat tttctatata taaccttttca agtttttatct | 2640 |
| ttctatatat ttttatagtt a | 2661 |

<210> SEQ ID NO 6
<211> LENGTH: 2279
<212> TYPE: DNA
<213> ORGANISM: Glycine max

<400> SEQUENCE: 6

| | |
|---|---|
| atgctggtgc cccacttaac attttctata ctatctttt catatttgtt caagtttgat | 60 |
| tctacactcc caccatatca attaaccatt atcatactaa acttgtttct tctaataatg | 120 |
| gctgcaacga cacgttccct tgcatccatc tatgatgtgt cctcaactt cagaggggaa | 180 |
| gacacgcgct atggttttac tggcaatctc tacaaggctc tttgtgacaa gggatttcat | 240 |
| accttctttg acgaagacaa gcttcacagc ggagaggaaa taacacctgc acttttgaag | 300 |
| gcaattcaag attccaggat tgctattatt gtgcttttctg aaaactatgc ttttttcctca | 360 |
| ttttgtttag atgaacttgt agccatccta cactgcaaga gggaagggct gttggttata | 420 |
| ccggtctttt acaaagtaga tccttctgat gttagacacc agaaaggtag ttatggagaa | 480 |
| gcaatgacta agcatcacga aaggttcaaa gataagatgg agaagctgca gaaatggagg | 540 |
| atggcattgc atcaagtagc tgacttgtct ggcaaacatt tcaaagatgg gtatacaatc | 600 |
| atactaatat attttacttt atggttttta ttggattatg gtttacttgt ctattgattt | 660 |
| aacttgtaaa atataaagag aaaataaatg cttgttaatc ttgacaatta atgtaccctat | 720 |
| caagacatgg atgcaaggct tttaggctga cttcatcaga actttttttg tttgttttgaa | 780 |
| acagagatgc atatgaatac aagtttattg ggagtattgt tgaggagctc tctaggaaga | 840 |
| ttaatcgtgc ttctttacat gttgcggatt atcctgttgg tttagagtca caagtgacag | 900 |
| aggtaatgaa gcttttggat gttggatccg atgatgttgt ccacatcata gggatccatg | 960 |
| gaatgggcgg gttaggaaaa acaacacttg ctctggcagt atataatttc attgctctcc | 1020 |
| atttttgatga atcctgttttt cttcaaaacg tgagagaaga atcaaataaa catgggttaa | 1080 |
| aacaccttca aagcatcctt cttttcaaaat tacttggtga aaggacatc atcttaacaa | 1140 |
| gttggcaaga aggagcttca atgatacaac ataggctccg acgaaagaag gttctcttga | 1200 |
| ttttagacga tgttgacaag tgtgagcaat taatggctat tgttggaaga cctgattggt | 1260 |
| ttggtcccgg tagcagagtc atcattacca ctcgggacga acatctgcta aaatgtcacg | 1320 |
| aggttgaaag aacttatgag gtgaaggttt tgaatcacaa tgctgctctt caactgctta | 1380 |
| ctaggaatgc ttttaaaaga gaaaaaattg atccaagtta tgaggacgtc ttgaatcgtg | 1440 |
| tagtagctta tgcttctggc cttccattgg ctttggaagt cataggctcg acttgtttg | 1500 |
| gaaaaactgt agcagaatgg gaatctgctg tggaacatta taaaagaatt cccagggata | 1560 |
| aaatccaaga gatactaaaa gtaagctttg atgctttggg ggaagaacaa aagaatgtgt | 1620 |
| ttcttgacat cgcttgttgc ttcaaagggt ataaatggac agaggttgat gatctactcc | 1680 |
| atgttctttta tggtaactgc aagaagcatc atattggggt gttggttgaa aaatctctca | 1740 |
| taaagtacta tgatgatact gttgaaatgc acgacctgat tcaggacatg ggtagagaaa | 1800 |
| ttgagcggca gagatcacca gatgagccag ggaagcgcaa gagattatgg tcaccacaag | 1860 |

| | | |
|---|---|---|
| atataattca agttttaaaa cacaacacgg tgagtgagct catgaatagt tgaatttttt | 1920 | |
| tttgtctatc tcatatattt acatcatggt taacttttc tttataattc gtaatatttt | 1980 | |
| ctaagcgagt caattgatat ttcacacaag ttgaattgtg gttgattcgt gccttttgc | 2040 | |
| attagcaggg aacttgtaaa attgaaatca tatgtttgga tccctccata tctgacaaag | 2100 | |
| aagaaacagt ggaatggaat gaaaacgcct tcatgaagat ggaaaacctt aaaatactta | 2160 | |
| ttattagaaa tggcaatttt tcgataggtc ccataatttt tccagaaggt ttgagagtac | 2220 | |
| tggaatggca aagatatcct tcaaattgtt taccgtctaa ctttgatccg atcaactga | 2279 | |

<210> SEQ ID NO 7
<211> LENGTH: 641
<212> TYPE: PRT
<213> ORGANISM: Glycine max

<400> SEQUENCE: 7

```
Met Leu Val Pro His Leu Thr Phe Ser Ile Leu Ser Phe Ser Tyr Leu
1               5                   10                  15

Phe Lys Phe Asp Ser Thr Leu Pro Pro Tyr Gln Leu Thr Ile Ile Ile
            20                  25                  30

Leu Asn Leu Phe Leu Leu Ile Met Ala Ala Thr Thr Arg Ser Leu Ala
        35                  40                  45

Ser Ile Tyr Asp Val Phe Leu Asn Phe Arg Gly Glu Asp Thr Arg Tyr
    50                  55                  60

Gly Phe Thr Gly Asn Leu Tyr Lys Ala Leu Cys Asp Lys Gly Phe His
65                  70                  75                  80

Thr Phe Phe Asp Glu Asp Lys Leu His Ser Gly Glu Glu Ile Thr Pro
                85                  90                  95

Ala Leu Leu Lys Ala Ile Gln Asp Ser Arg Ile Ala Ile Ile Val Leu
            100                 105                 110

Ser Glu Asn Tyr Ala Phe Ser Ser Phe Cys Leu Asp Glu Leu Val Ala
        115                 120                 125

Ile Leu His Cys Lys Arg Glu Gly Leu Leu Val Ile Pro Val Phe Tyr
    130                 135                 140

Lys Val Asp Pro Ser Asp Val Arg His Gln Lys Gly Ser Tyr Gly Glu
145                 150                 155                 160

Ala Met Thr Lys His His Glu Arg Phe Lys Asp Lys Met Glu Lys Leu
                165                 170                 175

Gln Lys Trp Arg Met Ala Leu His Gln Val Ala Asp Leu Ser Gly Lys
            180                 185                 190

His Phe Lys Asp Gly Asp Ala Tyr Glu Tyr Lys Phe Ile Gly Ser Ile
        195                 200                 205

Val Glu Glu Leu Ser Arg Lys Ile Asn Arg Ala Ser Leu His Val Ala
    210                 215                 220

Asp Tyr Pro Val Gly Leu Glu Ser Gln Val Thr Glu Val Met Lys Leu
225                 230                 235                 240

Leu Asp Val Gly Ser Asp Asp Val Val His Ile Gly Ile His Gly
                245                 250                 255

Met Gly Gly Leu Gly Lys Thr Thr Leu Ala Leu Ala Val Tyr Asn Phe
            260                 265                 270

Ile Ala Leu His Phe Asp Glu Ser Cys Phe Leu Gln Asn Val Arg Glu
        275                 280                 285

Glu Ser Asn Lys His Gly Leu Lys His Leu Gln Ser Ile Leu Leu Ser
    290                 295                 300
```

-continued

Lys Leu Leu Gly Glu Lys Asp Ile Ile Leu Thr Ser Trp Gln Glu Gly
305                 310                 315                 320

Ala Ser Met Ile Gln His Arg Leu Arg Arg Lys Lys Val Leu Leu Ile
            325                 330                 335

Leu Asp Asp Val Asp Lys Cys Glu Gln Leu Met Ala Ile Val Gly Arg
                340                 345                 350

Pro Asp Trp Phe Gly Pro Gly Ser Arg Val Ile Ile Thr Thr Arg Asp
            355                 360                 365

Glu His Leu Leu Lys Cys His Glu Val Glu Arg Thr Tyr Glu Val Lys
        370                 375                 380

Val Leu Asn His Asn Ala Ala Leu Gln Leu Leu Thr Arg Asn Ala Phe
385                 390                 395                 400

Lys Arg Glu Lys Ile Asp Pro Ser Tyr Glu Asp Val Leu Asn Arg Val
                405                 410                 415

Val Ala Tyr Ala Ser Gly Leu Pro Leu Ala Leu Glu Val Ile Gly Ser
            420                 425                 430

Asp Leu Phe Gly Lys Thr Val Ala Glu Trp Glu Ser Ala Val Glu His
        435                 440                 445

Tyr Lys Arg Ile Pro Arg Asp Lys Ile Gln Glu Ile Leu Lys Val Ser
450                 455                 460

Phe Asp Ala Leu Gly Glu Glu Gln Lys Asn Val Phe Leu Asp Ile Ala
465                 470                 475                 480

Cys Cys Phe Lys Gly Tyr Lys Trp Thr Glu Val Asp Asp Leu Leu His
                485                 490                 495

Val Leu Tyr Gly Asn Cys Lys Lys His His Ile Gly Val Leu Val Glu
            500                 505                 510

Lys Ser Leu Ile Lys Tyr Tyr Asp Asp Thr Val Glu Met His Asp Leu
        515                 520                 525

Ile Gln Asp Met Gly Arg Glu Ile Glu Arg Gln Arg Ser Pro Asp Glu
530                 535                 540

Pro Gly Lys Arg Lys Arg Leu Trp Ser Pro Gln Asp Ile Ile Gln Val
545                 550                 555                 560

Leu Lys His Asn Thr Gly Thr Cys Lys Ile Glu Ile Ile Cys Leu Asp
                565                 570                 575

Pro Ser Ile Ser Asp Lys Glu Glu Thr Val Glu Trp Asn Glu Asn Ala
            580                 585                 590

Phe Met Lys Met Glu Asn Leu Lys Ile Leu Ile Ile Arg Asn Gly Asn
        595                 600                 605

Phe Ser Ile Gly Pro Asn Asn Phe Pro Glu Gly Leu Arg Val Leu Glu
610                 615                 620

Trp Gln Arg Tyr Pro Ser Asn Cys Leu Pro Ser Asn Phe Asp Pro Ile
625                 630                 635                 640

Asn

<210> SEQ ID NO 8
<211> LENGTH: 4410
<212> TYPE: DNA
<213> ORGANISM: Glycine max

<400> SEQUENCE: 8
ttttaattta tctgtgttaa cttctttctt tacatagaat ttattagtgt taactaagaa    60
ctgcatatat gctcaaagac atacacatgt cctcatatat taaaatcctt ccttgttatt   120
aggggtggaa ataggtcagg ccaaatcgct ttgaaaggtg cttaacctat gatgaatctt   180

```
tgaggccaga acttgaccta tagcctatca acgactttta ttttggctcg gtctgacggt    240
cttttataag cctggtctga cctgatagtc tttttaaatc ttcacaataa atatttaata    300
tttcgtggag tagaaacgta ataggaaagt taaagaaaaa ggaaagtcaa tcaaaataat    360
aatgaacaat ataaaatgac acatgactca cacctaaatt gtaattaaag tcaactttga    420
taagatgtgt acgcgttact agttattgtc gttattatcg tttagcctca tatgtcattg    480
tcactctgcc taataataaa catttgtgtg accgcgtcaa ataatgctgg tgccccactt    540
aacattttct atactatctt tttcatattt gttcaagttt gattctacac tcccaccata    600
tcaattaacc attatcatac taaacttgtt tcttctaata atggctgcaa cgacacgttc    660
ccttgcatcc atctatgatg tgttcctcaa cttcagaggg gaagacacgc gctatggttt    720
tactggcaat ctctacaagg ctctttgtga caagggattt catccttct ttgacgaaga    780 caagcttcac agcggagagg aaataacacc tgcacttttg aaggcaattc aagattccag    840
gattgctatt attgtgcttt ctgaaaacta tgcttttcc tcattttgtt tagatgaact    900
tgtagccatc ctacactgca agagggaagg gctgttggtt ataccggtct tttacaaagt    960
agatccttct gatgttagac accagaaagg tagttatgga gaagcaatga ctaagcatca   1020
cgaaaggttc aaagataaga tggagaagct gcagaaatgg aggatggcat tgcatcaagt   1080
agctgacttg tctggcaaac atttcaaaga tggagatgca tatgaataca gtttattgg   1140 gagtattgtt gaggagctct ctaggaagat taatcgtgct tctttacatg ttgcggatta   1200
tcctgttggt ttagagtcac aagtgacaga ggtaatgaag cttttggatg ttggatccga   1260
tgatgttgtc cacatcatag ggatccatgg aatgggcggg ttaggaaaaa caacacttgc   1320
tctggcagta tataatttca ttgctctcca ttttgatgaa tcctgttttc ttcaaaacgt   1380
gagagaagaa tcaaataaac atgggttaaa acaccttcaa agcatccttc tttcaaaatt   1440
acttggtgag aaggacatca tcttaacaag ttggcaagaa ggagcttcaa tgatacaaca   1500
taggctccga cgaaagaagg ttctcttgat tttagacgat gttgacaagt gtgagcaatt   1560
aatggctatt gttggaagac ctgattggtt tggtcccggt agcagagtca tcattaccac   1620
tcgggacgaa catctgctaa aatgtcacga ggttgaaaga acttatgagg tgaaggtttt   1680
gaatcacaat gctgctcttc aactgcttac taggaatgct tttaaaagag aaaaaattga   1740
tccaagttat gaggacgtct tgaatcgtgt agtagcttat gcttctggcc ttccattggc   1800
tttggaagtc ataggctcgg acttgttttgg aaaaactgta gcagaatggg aatctgctgt   1860
ggaacattat aaaagaattc ccagggataa aatccaagag atactaaaag taagctttga   1920
tgctttgggg gaagaacaaa agaatgtgtt tcttgacatc gcttgttgct tcaaagggta   1980
taaatggaca gaggttgatg atctactcca tgttctttat ggtaactgca agaagcatca   2040 tattgggtg ttggttgaaa atctctcat aaagtactat gatgatactg ttgaaatgca   2100
cgacctgatt caggacatgg gtagagaaat tgagcggcag agatcaccag atgagccagg   2160
gaagcgcaag agattatggt caccacaaga tataattcaa gttttaaaac acaacacggg   2220
aacttgtaaa attgaaatca tatgtttgga tccctccata tctgacaaag aagaaacagt   2280
ggaatggaat gaaaacgcct tcatgaagat ggaaaaccct taaaatactta ttattagaaa   2340 tggcaatttt tcgataggtc ccaataattt tccagaaggt ttgagagtac tggaatggca   2400
aagatatcct tcaaattgtt taccgtctaa cttttgatccg atcaactgat aggaacacag   2460
agaagacaac aacaaaggct tacacagggg tcgaaatagc agaacaggag gtgcagaagc   2520
aagccaaacc caaatggaga attacgaaac catcttacct cagtgagtat gtctgaggaa   2580
```

| | | |
|---|---|---|
| gaatggtaaa tgaatagcgg aaagcaccaa attaggaaaa gggaacatcc ttgctgagtg | 2640 |
| tgtcttcatt aggggacag cactaacaga attacaattg ccaaaccatt ctagaagctt | 2700 |
| tttctgttac tagggaaact tatatatata tatgtaaata acacagcaag gaattaatgg | 2760 |
| gaaatacttc aattaccttc tttctctgtg ccttcttctt cttcttctgt gtcttcttct | 2820 |
| tctcattttc aggggagtgc taacatcaac cttgttatat gcaagttacc tgatagttcc | 2880 |
| attacgtcat ttgagttcca tggctcatcc aagaagttgg ggcatctaac agttctgaat | 2940 |
| tttgacaagt gcaaatttt aacacagata cctgatgtat ctgatcttcc aaatttgagg | 3000 |
| gaactttcat ttcgatggtg tgagagttta gttgcagttg atgactcaat tggttttctg | 3060 |
| aataaactta aagaattgag tgctgatggt tgcaggaagc ttacgagttt ccgcctctc | 3120 |
| aacttgacct ctcttgaaac acttgaaatt tctgagtgtt ccagtcttag tattttccag | 3180 |
| aaatattagg agagatggaa acatacaga aacttcgttt gactgacctt cccataaaaa | 3240 |
| aattgccatt tcaattcaa atcttactg gactccaatg gttaaccctg gggagctgtg | 3300 |
| gaattgttca gttaccatgt agcttatcca tgatgcccaa actgttggaa ttcaatatta | 3360 |
| gagattgcaa caggtggcaa tgggtagaat cggaagaagg tgaagaaaaa gtgggcccaa | 3420 |
| cacagtcttc aacggaacat tgctttggtg ccacgaagtg caatttatgt gatgatttt | 3480 |
| ttttaacagg ttccaagagg tttgctcttg taacattttt agatctatcg gagaataatt | 3540 |
| tcaccatcct tcccgaattc ttcaaagaat tggaattttt acaaactctt ttcgtgagtg | 3600 |
| attgcgagca tcttcaggaa attagagggc ttccaccaaa cttagagtat tttgatgcaa | 3660 |
| gaaactgtgc atccttgact tcctcgacta aaagcatgct tttaaatcag gaactgcatg | 3720 |
| aggctagacc aacccagttt gtgtttccag gaacaagaat accagagtgg ttcgatcagc | 3780 |
| aaaagagtgg acattcaatt tcttctggt ttcgtaataa actcccagcc aaacttcttt | 3840 |
| gtcttcttat tgcactgtct actgagaatt ttatcctatc tccagacgtg ttcatcaatg | 3900 |
| gaaaatttga agaattggag ccctataaga cggacgaaat agaaagtatg tcgaaattgg | 3960 |
| atcatactta tatctttat ctccaaaagt tacctttcaa aaatggtaat ctgtttgaag | 4020 |
| aagtggctag ggaaaaggaa tggaaccatg tggaggttag atatgaaagt gtgttagagt | 4080 |
| tagagagctc actcatcaaa ggaagtggaa tccatatatt cagagaagaa ggcagtatgg | 4140 |
| aggaagatat tcgatttgat gatccatatc tcagcagctc tgcatcagaa agcccctcct | 4200 |
| tcctacaaac catagctttg gggacacgca agttttccat tgcttttttc ttattttt | 4260 |
| catgtttttt tatttatta ttttggtttc agtcttcaaa aaacgactta atccaactgg | 4320 |
| tgttcgccct atcttcataa tgtacttttg actcatttat attcatcttt catgactta | 4380 |
| tgcattttct atatataacc tttcaagttt | 4410 |

<210> SEQ ID NO 9
<211> LENGTH: 558
<212> TYPE: DNA
<213> ORGANISM: Glycine max

<400> SEQUENCE: 9

| | | |
|---|---|---|
| atgaagcttt tggatgttgg atccgatgat gttgtccata taatagggat ccatgggatg | 60 |
| cgtgggttag gaaaaacaac ccttgctcta gctgtttata attcgattgc tggtcatttt | 120 |
| gatgaagcct gttttcttga aaacgtgaga gaagaatcaa gtaaacatgg gttaaaacac | 180 |
| cttcaaagca tcattatttc aaaattactt ggtgagaagg acatcaactt agcaagttgg | 240 |

| | |
|---|---|
| caagaaggag cttcaatgat acaaagtagg ctccgacgaa agaaggttct cttgatttta | 300 |
| gacgatgtca acaagcgcga gcaattaaag gctattgttg gaagatctga ttggtttggt | 360 |
| cccggtagca gagtcatcat taccactcgg gacaaatatc tgctaaaaga tcacgaggtt | 420 |
| gaaagaactt atgggggtgaa ttataaattg tttggaaaaa ctgtagcaaa atgggaatct | 480 |
| gctgtcggtg attatacaaa gctcttgata tataagacag gggaatctac actttcaatg | 540 |
| atagaaggat ggctttga | 558 |

<210> SEQ ID NO 10
<211> LENGTH: 185
<212> TYPE: PRT
<213> ORGANISM: Glycine max

<400> SEQUENCE: 10

Met Lys Leu Leu Asp Val Gly Ser Asp Asp Val Val His Ile Ile Gly
1               5                   10                  15

Ile His Gly Met Arg Gly Leu Gly Lys Thr Thr Leu Ala Leu Ala Val
            20                  25                  30

Tyr Asn Ser Ile Ala Gly His Phe Asp Glu Ala Cys Phe Leu Glu Asn
        35                  40                  45

Val Arg Glu Glu Ser Ser Lys His Gly Leu Lys His Leu Gln Ser Ile
    50                  55                  60

Ile Ile Ser Lys Leu Leu Gly Glu Lys Asp Ile Asn Leu Ala Ser Trp
65                  70                  75                  80

Gln Glu Gly Ala Ser Met Ile Gln Ser Arg Leu Arg Arg Lys Lys Val
                85                  90                  95

Leu Leu Ile Leu Asp Asp Val Asn Lys Arg Glu Gln Leu Lys Ala Ile
            100                 105                 110

Val Gly Arg Ser Asp Trp Phe Gly Pro Gly Ser Arg Val Ile Ile Thr
        115                 120                 125

Thr Arg Asp Lys Tyr Leu Leu Lys Asp His Glu Val Glu Arg Thr Tyr
    130                 135                 140

Gly Val Asn Tyr Lys Leu Phe Gly Lys Thr Val Ala Lys Trp Glu Ser
145                 150                 155                 160

Ala Val Gly Asp Tyr Thr Lys Leu Leu Ile Tyr Lys Thr Gly Glu Ser
                165                 170                 175

Thr Leu Ser Met Ile Glu Gly Trp Leu
            180                 185

<210> SEQ ID NO 11
<211> LENGTH: 1993
<212> TYPE: DNA
<213> ORGANISM: Glycine max

<400> SEQUENCE: 11

| | |
|---|---|
| tcaagtttga ttctccctcc taccatatca accataacca tactaaactt tgttcttcta | 60 |
| ataatggctg caacgacacg ttcccttgca tccatctatg atgtgttcct cagcttcaga | 120 |
| gggacagaca cacgctatgg ttttactggc aatctctaca aggctctttg tgacaaggga | 180 |
| tttcatacct tctttgacga agacaagctt cacagcggag aggaaataac acctgcactt | 240 |
| ttgaaggcaa ttcaagattc cagggttgct attattgtgc tttctgaaaa ctatgctttt | 300 |
| tcctcatttt gtttagatga acttgtaacc atctttcact gcaagaggga agggctgttg | 360 |
| gttataccgg tcttttacaa agtcgatcct tcttatgtca gacaccagaa aggtagttat | 420 |
| ggagaagcaa tgactaagca tcaggaaagg ttcaaagata agatggagaa gctgcaggaa | 480 |

```
tggaggatgg ctttgaaaca agtagctgac ttgtctggct ctcatttcaa agatggagac    540
gcatatgaat acaagtttat tgtgaatatt gttgaggagg tctctaggaa gattggtcgt    600
ggttctttac atgttgcgga ttatccggtt ggtcaagcgt cacaagtgac agaggtaatg    660
aagcttttgg atgttggatc cgatgatgtt gtccatataa tagggatcca tgggatgcgt    720
gggttaggaa aaacaaccct tgctctagct gtttataatt cgattgctgg tcattttgat    780
gaagcctgtt ttcttgaaaa cgtgagagaa gaatcaagta acatgggtt aaaacacctt    840 caaagcatca ttatttcaaa attacttggt gagaaggaca tcaacttagc aagttggcaa    900
gaaggagctt caatgataca agtaggctc cgacgaaaga aggttctctt gattttagac    960
gatgtcaaca agcgcgagca attaaaggct attgttggaa gatctgattg gtttggtccc   1020
ggtagcagag tcatcattac cactcgggac aaatatctgc taaaagatca cgaggttgaa   1080
agaacttatg gggtgaatta taaattgttt ggaaaaactg tagcaaaatg gaatctgct   1140 gtcggtgatt atacaaagct cttgatatat aagacagggg aatctacact ttcaatgata   1200
gaaggatggc tttgaaacaa gtagctgact tgtctggctc tcatttcaaa gatgggtata   1260
caatcatact aatatatttt acttatggt tttattgga ttaggtttta cttgtctatt     1320
gatttaacta gtcaaattta aatagaaaag aaatgctctt gttaaccttg acaattaatg   1380
tacctatcaa gacatggatg caaggatttt aggctgactt catcattacc actcgggaca   1440
aatatctgct aaaagatcac gaggttgaaa gaacttatgg ggtgaattat aaattgtttg   1500
gaaaaactgt agcaaaatgg aatctgctg tcggtgatta tacaaagctc ttgatatata   1560
tgacagggga atctacactt tcattgatga tgaggagctt ccgagaggag acaaaataac   1620
acctgcactt ttcagttttt taaatcctca acgtcttcgt aatttctgta tcttttgct   1680 tttaattctt tcagtttttg tatttgcagt tcataatttg aaaagaaaac atcacttcct   1740
aataattaag catgaataac tatgaataac tgctaaataa ttttttaaa gacattttca   1800 ctttatttt cattatgaaa aacacattta tttaacagtt attaatgcat aggcctttct    1860
ccgcaaattg ttaggatccc ccagttgtag gtttgaatct taagctgctc ttttttgaaa   1920
cctgtaagag tttaagatca gaaaagatta ccatatgtat accattagaa taaatttcat   1980
cttaattcat att                                                     1993
```

<210> SEQ ID NO 12
<211> LENGTH: 20
<212> TYPE: DNA
<213> ORGANISM: Glycine max

<400> SEQUENCE: 12

```
tgtgaacatt cgtagttgtc                                                20
```

<210> SEQ ID NO 13
<211> LENGTH: 20
<212> TYPE: DNA
<213> ORGANISM: Glycine max

<400> SEQUENCE: 13

```
ttccactgac tcacaaaaag                                                20
```

<210> SEQ ID NO 14
<211> LENGTH: 20
<212> TYPE: DNA
<213> ORGANISM: Glycine max

```
<400> SEQUENCE: 14
tggctcatcg aaggcatgtt                                              20

<210> SEQ ID NO 15
<211> LENGTH: 20
<212> TYPE: DNA
<213> ORGANISM: Glycine max

<400> SEQUENCE: 15
gaggtcaagt tgagaggcgg                                              20

<210> SEQ ID NO 16
<211> LENGTH: 22
<212> TYPE: DNA
<213> ORGANISM: Glycine max

<400> SEQUENCE: 16
tcccagggat aaaatccaag ag                                           22

<210> SEQ ID NO 17
<211> LENGTH: 20
<212> TYPE: DNA
<213> ORGANISM: Glycine max

<400> SEQUENCE: 17
ggtgatctct gccgctcaat                                              20

<210> SEQ ID NO 18
<211> LENGTH: 24
<212> TYPE: DNA
<213> ORGANISM: Glycine max

<400> SEQUENCE: 18
cactttcaat gatagaagga tggc                                         24

<210> SEQ ID NO 19
<211> LENGTH: 20
<212> TYPE: DNA
<213> ORGANISM: Glycine max

<400> SEQUENCE: 19
tcctctcgga agctcctcat                                              20

<210> SEQ ID NO 20
<211> LENGTH: 22
<212> TYPE: DNA
<213> ORGANISM: Glycine max

<400> SEQUENCE: 20
gcgtggcacc cttgataaat aa                                           22

<210> SEQ ID NO 21
<211> LENGTH: 24
<212> TYPE: DNA
<213> ORGANISM: Glycine max

<400> SEQUENCE: 21
gcgcacgaaa gttttttctgt aaca                                        24

<210> SEQ ID NO 22
<211> LENGTH: 20
<212> TYPE: DNA
<213> ORGANISM: Glycine max
```

<400> SEQUENCE: 22
ttatgaccaa ttttcccccc                                            20

<210> SEQ ID NO 23
<211> LENGTH: 20
<212> TYPE: DNA
<213> ORGANISM: Glycine max

<400> SEQUENCE: 23
gaaattttga ctgccacggt                                            20

<210> SEQ ID NO 24
<211> LENGTH: 20
<212> TYPE: DNA
<213> ORGANISM: Glycine max

<400> SEQUENCE: 24
tgccatatgc aaattaccca                                            20

<210> SEQ ID NO 25
<211> LENGTH: 21
<212> TYPE: DNA
<213> ORGANISM: Glycine max

<400> SEQUENCE: 25
aaacattcag tcccgtcaaa a                                          21

<210> SEQ ID NO 26
<211> LENGTH: 20
<212> TYPE: DNA
<213> ORGANISM: Glycine max

<400> SEQUENCE: 26
ccactggtaa atttgggtca                                            20

<210> SEQ ID NO 27
<211> LENGTH: 25
<212> TYPE: DNA
<213> ORGANISM: Glycine max

<400> SEQUENCE: 27
caaccatgtt gttaatatga atgga                                      25

<210> SEQ ID NO 28
<211> LENGTH: 20
<212> TYPE: DNA
<213> ORGANISM: Glycine max

<400> SEQUENCE: 28
ccctcttcat ttcccttggt                                            20

<210> SEQ ID NO 29
<211> LENGTH: 22
<212> TYPE: DNA
<213> ORGANISM: Glycine max

<400> SEQUENCE: 29
cctcccaata tctttgggat aa                                         22

<210> SEQ ID NO 30
<211> LENGTH: 21
<212> TYPE: DNA

```
<213> ORGANISM: Glycine max

<400> SEQUENCE: 30
gcacataaca tcacccactg a                                              21

<210> SEQ ID NO 31
<211> LENGTH: 20
<212> TYPE: DNA
<213> ORGANISM: Glycine max

<400> SEQUENCE: 31
aaacagagag gcccgaagtt                                                20

<210> SEQ ID NO 32
<211> LENGTH: 26
<212> TYPE: DNA
<213> ORGANISM: Glycine max

<400> SEQUENCE: 32
gcgtcttagt cgtgctgaca ctactc                                         26

<210> SEQ ID NO 33
<211> LENGTH: 30
<212> TYPE: DNA
<213> ORGANISM: Glycine max

<400> SEQUENCE: 33
gcgagtttgt ttagctcaat ctttcactca                                     30

<210> SEQ ID NO 34
<211> LENGTH: 20
<212> TYPE: DNA
<213> ORGANISM: Glycine max

<400> SEQUENCE: 34
tgtgttcttg aatgaggcga                                                20

<210> SEQ ID NO 35
<211> LENGTH: 21
<212> TYPE: DNA
<213> ORGANISM: Glycine max

<400> SEQUENCE: 35
tcagctgatg tttgaacgaa a                                              21

<210> SEQ ID NO 36
<211> LENGTH: 203
<212> TYPE: DNA
<213> ORGANISM: Glycine max

<400> SEQUENCE: 36
ttaaaataaa attcaagatg ctttatattt gcggaaagtt tgatagtctt tgaactccgg    60
attttctggc gttgatttgt gaacacgata tacccttttgc caatgaattt ccagcaactt  120
caaattaacg taaactttaa atgtttgaga atgtctgtgg tagtcttaat tgtgatggag  180
ataattttta tggagacacg tgc                                           203

<210> SEQ ID NO 37
<211> LENGTH: 203
<212> TYPE: DNA
<213> ORGANISM: Glycine max

<400> SEQUENCE: 37
```

```
ttaaaataaa attcaagatg ctttatattt gcggaaagtt tgatagtctt tgaactccgg    60
attttctggc gttgatttgt gaacacgata taccctttgc cgatgaattt ccagcaactt   120
caaattaacg taaactttaa atgtttgaga atgtctgtgg tagtcttaat tgtgatggag   180
ataattttta tggagacacg tgc                                          203

<210> SEQ ID NO 38
<211> LENGTH: 203
<212> TYPE: DNA
<213> ORGANISM: Glycine max

<400> SEQUENCE: 38
aggtagccta tgttatggat aaatttatgt tatcccgcgt aatactcagt gttatgggca    60
gttcttttgg gagaagaaaa aattgagata tgtttaatct ctacttctgg aattcaaatt   120
tcagccttat atcaaaacct gttaaagttt cacaaccaga tgtttcaaag gcattgaata   180
tgatttcgta tatcagtggc tat                                          203

<210> SEQ ID NO 39
<211> LENGTH: 203
<212> TYPE: DNA
<213> ORGANISM: Glycine max

<400> SEQUENCE: 39
aggtagccta tgttatggat aaatttatgt tatcccgcgt aatactcagt gttatgggca    60
gttcttttgg gagaagaaaa aattgagata tgtttaatct caacttctgg aattcaaatt   120
tcagccttat atcaaaacct gttaaagttt cacaaccaga tgtttcaaag gcattgaata   180
tgatttcgta tatcagtggc tat                                          203

<210> SEQ ID NO 40
<211> LENGTH: 203
<212> TYPE: DNA
<213> ORGANISM: Glycine max

<400> SEQUENCE: 40
ttattccccg acagatttaa atgtcctaca cgagcaaagg tcttgaaacc tgttaaaaaa    60
aaatcatcac atagattgca atccttggcc gaaaaccgat gtgcctttga agatggtatt   120
gagcccactt ttttttcacc ttcttccgat tctacccatt gccacctgtt gcaatattcc   180
atatggaatt caaacagttc ggg                                          203

<210> SEQ ID NO 41
<211> LENGTH: 203
<212> TYPE: DNA
<213> ORGANISM: Glycine max

<400> SEQUENCE: 41
ttattccccg acagatttaa atgtcctaca cgagcaaagg tcttgaaacc tgttaaaaaa    60
aaatcatcac atagattgca atccttggcc gaaaaccgat gcgcctttga agatggtatt   120
gagcccactt ttttttcacc ttcttccgat tctacccatt gccacctgtt gcaatattcc   180
atatggaatt caaacagttc ggg                                          203

<210> SEQ ID NO 42
<211> LENGTH: 203
<212> TYPE: DNA
<213> ORGANISM: Glycine max
```

<400> SEQUENCE: 42

```
ctctgttttg ccgaggagag tgtcactgca agcataactg gtacgacgga gccatcagaa      60
ccaccatata gcattttgtc ttttctcttt ccttcctccc cgctctttct cctttccttc     120
tctttcttac cttctccgtt gatgatggat ttcagatctt caattgcttc ttgcaccacc     180
atcaaccacg actttcgcat cta                                             203
```

<210> SEQ ID NO 43
<211> LENGTH: 203
<212> TYPE: DNA
<213> ORGANISM: Glycine max

<400> SEQUENCE: 43

```
ctctgttttg ccgaggagag tgtcactgca agcataactg gtacgacgga gccatcagaa      60
ccaccatata gcattttgtc ttttctcttt ccttcctccc cactctttct cctttccttc     120
tctttcttac cttctccgtt gatgatggat ttcagatctt caattgcttc ttgcaccacc     180
atcaaccacg actttcgcat cta                                             203
```

<210> SEQ ID NO 44
<211> LENGTH: 203
<212> TYPE: DNA
<213> ORGANISM: Glycine max

<400> SEQUENCE: 44

```
tggaagtgaa gaaataaaga tattttttag atgcaagaag gaggaaactg aaaacgaagc      60
aagtagtact actgtggtgt ggtgttattt tgtttggttg tttgataata attgtaagca     120
tcagtaatgg gcagtgggtg gcagcacatg gccgccgtgc tccaccaatc accaatccaa     180
cttcgctttc ttaaatcata tcg                                             203
```

<210> SEQ ID NO 45
<211> LENGTH: 204
<212> TYPE: DNA
<213> ORGANISM: Glycine max

<400> SEQUENCE: 45

```
tggaagtgaa gaaataaaga tattttttag atgcaagaag gaggaaactg aaaacgaagc      60
aagtagtact actgtggtgt ggtgttattt tgtttggttg tcctgataat aattgtaagc     120
atcagtaatg ggcagtgggt ggcagcacat ggccgccgtg ctccaccaat caccaatcca     180
acttcgcttt cttaaatcat atcg                                            204
```

<210> SEQ ID NO 46
<211> LENGTH: 203
<212> TYPE: DNA
<213> ORGANISM: Glycine max

<400> SEQUENCE: 46

```
atataattaa attattttac aagaaattta tatccctatt tttttataaa ataatccaa      60
aatcatcaat ttcttcccct cccaatgtac tgttgacatc cctaatatat tttcaagtat     120
ttttcagtaa ctactgaatt ttttgtttca cataacaaat taaaccacac tgaaactctg     180
gcatgattat atggaattat tta                                             203
```

<210> SEQ ID NO 47
<211> LENGTH: 203
<212> TYPE: DNA
<213> ORGANISM: Glycine max

<400> SEQUENCE: 47

```
atataattaa attattttac aagaaattta tatccctatt tttttataaa aataatccaa      60
aatcatcaat ttcttccctt cccaatgtac tgttgacatc cttaatatat tttcaagtat     120
ttttcagtaa ctactgaatt ttttgtttca cataacaaat taaaccacac tgaaactctg     180
gcatgattat atggaattat tta                                             203
```

<210> SEQ ID NO 48
<211> LENGTH: 203
<212> TYPE: DNA
<213> ORGANISM: Glycine max

<400> SEQUENCE: 48

```
atccattgga aacaaataag ctttgtgttc atgttcgttt tcctgaatat ttttctagat      60
ctccgcagtg aaacattccg attgttgttg agtagaacac cccgagtacg aaaatcgttc    120
tcgaagttag tttttcgtgt tgagacgaaa tcagaaacga agccaagggc atattgggca    180
taatgttttt taatttttaa tta                                             203
```

<210> SEQ ID NO 49
<211> LENGTH: 203
<212> TYPE: DNA
<213> ORGANISM: Glycine max

<400> SEQUENCE: 49

```
atccattgga aacaaataag ctttgtgttc atgttcgttt tcctgaatat ttttctagat      60
ctccgcagtg aaacattccg attgttgttg agtagaacac cgcgagtacg aaaatcgttc    120
tcgaagttag tttttcgtgt tgagacgaaa tcagaaacga agccaagggc atattgggca    180
taatgttttt taatttttaa tta                                             203
```

<210> SEQ ID NO 50
<211> LENGTH: 203
<212> TYPE: DNA
<213> ORGANISM: Glycine max

<400> SEQUENCE: 50

```
tgcactttt ttttttttt gaaagaaagg gtctccctaa ttattttga ttgtaaactt         60
agccattcat tgagctgaaa taaagtatct tcaatcattg gtgaaaaagg caagaatat     120
aaattatgaa tagaaagcct cgttaaccc gcttcacggg attccatttt atgtcaggta      180
tgacaaatta aactgcgttc agt                                             203
```

<210> SEQ ID NO 51
<211> LENGTH: 203
<212> TYPE: DNA
<213> ORGANISM: Glycine max

<400> SEQUENCE: 51

```
tgcactttt ttttttttt gaaagaaagg gtctccctaa ttattttga ttgtaaactt         60
agccattcat tgagctgaaa taaagtatct tcaatcattg gagaaaaagg caagaatat     120
aaattatgaa tagaaagcct cgttaaccc gcttcacggg attccatttt atgtcaggta      180
tgacaaatta aactgcgttc agt                                             203
```

<210> SEQ ID NO 52
<211> LENGTH: 203
<212> TYPE: DNA

<213> ORGANISM: Glycine max

<400> SEQUENCE: 52

```
aattgaataa agaaaaacaa aaaaattgca ataagttga aggatatata attgaaagcg    60
gcaggacgcc gtttggtgga gacccaccaa tatgatgtag ccctcaggtc attagtggca   120
acaactccat tgttatttgt taccacaacc tagctatatc ttaatagcct caatgtcccc   180
atccttaggc ttcaagagta cta                                          203
```

<210> SEQ ID NO 53
<211> LENGTH: 203
<212> TYPE: DNA
<213> ORGANISM: Glycine max

<400> SEQUENCE: 53

```
aattgaataa agaaaaacaa aaaaattgca ataagttga aggatatata attgaaagcg    60
gcaggacgcc gtttggtgga gacccaccaa tatgatgtag ctctcaggtc attagtggca   120
acaactccat tgttatttgt taccacaacc tagctatatc ttaatagcct caatgtcccc   180
atccttaggc ttcaagagta cta                                          203
```

<210> SEQ ID NO 54
<211> LENGTH: 203
<212> TYPE: DNA
<213> ORGANISM: Glycine max

<400> SEQUENCE: 54

```
tttatggttt gagtactttc cagtaatttt tgggattatc tgttgaaata tacttatctt    60
tttttctcat cttttattct gacaaaatta tcagaattag caataacaac ttctggattg   120
gttctcgttg atgacaaatg taactaaccc actagtattt ttttgttct aactcagagc    180
cacaaaagtt ctccaaagat ggt                                          203
```

<210> SEQ ID NO 55
<211> LENGTH: 203
<212> TYPE: DNA
<213> ORGANISM: Glycine max

<400> SEQUENCE: 55

```
tttatggttt gagtactttc cagtaatttt tgggattatc tgttgaaata tacttatctt    60
tttttctcat cttttattct gacaaaatta tcagaattag cgataacaac ttctggattg   120
gttctcgttg atgacaaatg taactaaccc actagtattt ttttgttct aactcagagc    180
cacaaaagtt ctccaaagat ggt                                          203
```

<210> SEQ ID NO 56
<211> LENGTH: 203
<212> TYPE: DNA
<213> ORGANISM: Glycine max

<400> SEQUENCE: 56

```
cactgtaagt aatacagcat aacttgaaaa atgttcaaag agtactagga aaatggctac    60
tgaaggtact ttgagtttga gggtcatgcc gcctcccact ccaaatcttt ccctcgaaac   120
tgtgtccctc catttctttc tcttccttcc ctgttaaagt tcccccactt acaacctgct   180
gcatagacag acaattacaa tta                                          203
```

<210> SEQ ID NO 57
<211> LENGTH: 203

<212> TYPE: DNA
<213> ORGANISM: Glycine max

<400> SEQUENCE: 57

```
cactgtaagt aatacagcat aacttgaaaa atgttcaaag agtactagga aaatggctac    60
tgaaggtact ttgagtttga gggtcatgcc gcctcccact ctaaatcttt ccctcgaaac   120
tgtgtccctc catttctttc tcttccttcc ctgttaaagt tcccccactt acaacctgct   180
gcatagacag acaattacaa tta                                           203
```

<210> SEQ ID NO 58
<211> LENGTH: 203
<212> TYPE: DNA
<213> ORGANISM: Glycine max

<400> SEQUENCE: 58

```
caaaattttt actaaaaatc acaatatagt ttgtagtact ttttttcata atttttttc    60
cacttttgat tccttttaat atgcactaaa aaatctaaaa tgactttta ttcaataaaa   120
tgatgaattg tgtttaacac caataatcat gtttgacact actttcaaag acatcaaaca   180
agtctcctgg tgttttcgga tgc                                           203
```

<210> SEQ ID NO 59
<211> LENGTH: 203
<212> TYPE: DNA
<213> ORGANISM: Glycine max

<400> SEQUENCE: 59

```
caaaattttt actaaaaatc acaatatagt ttgtagtact ttttttcata atttttttc    60
cacttttgat tccttttaat atgcactaaa aaatctaaaa taactttta ttcaataaaa   120
tgatgaattg tgtttaacac caataatcat gtttgacact actttcaaag acatcaaaca   180
agtctcctgg tgttttcgga tgc                                           203
```

<210> SEQ ID NO 60
<211> LENGTH: 203
<212> TYPE: DNA
<213> ORGANISM: Glycine max

<400> SEQUENCE: 60

```
atcaacaaca taagaagtat aacaagagaa ccaggagcgt tttttttctt tgcatgctct    60
gtttgtttgg cagagaaaaa cagggaagag tgagagaaag taggaaactt tcaacatca   120
gtacatctca tttgaaaaac aaaacatgcc cattaaagat cagatacatt gttaaacaat   180
gcagcaagca gcaattacat ggc                                           203
```

<210> SEQ ID NO 61
<211> LENGTH: 203
<212> TYPE: DNA
<213> ORGANISM: Glycine max

<400> SEQUENCE: 61

```
atcaacaaca taagaagtat aacaagagaa ccaggagcgt tttttttctt tgcatgctct    60
gtttgtttgg cagagaaaaa cagggaagag tgagagaaag ttggaaactt tcaacatca   120
gtacatctca tttgaaaaac aaaacatgcc cattaaagat cagatacatt gttaaacaat   180
gcagcaagca gcaattacat ggc                                           203
```

<210> SEQ ID NO 62

```
<211> LENGTH: 203
<212> TYPE: DNA
<213> ORGANISM: Glycine max

<400> SEQUENCE: 62
gaaaaggata cgtgaaagaa agcactaacc aagattatca tagaaattac aagaagaggt        60
ccagaccaaa gaacagacat aaatagtcca ctcggatcaa agtagttatg actagagaag       120
cttttccagt ttttccccaa aaatctgttc agactctcag caagatatac accaaccact       180
gcatcaaaac aatttgtagg taa                                               203

<210> SEQ ID NO 63
<211> LENGTH: 203
<212> TYPE: DNA
<213> ORGANISM: Glycine max

<400> SEQUENCE: 63
gaaaaggata cgtgaaagaa agcactaacc aagattatca tagaaattac aagaagaggt        60
ccagaccaaa gaacagacat aaatagtcca ctcggatcaa actagttatg actagagaag       120
cttttccagt ttttccccaa aaatctgttc agactctcag caagatatac accaaccact       180
gcatcaaaac aatttgtagg taa                                               203

<210> SEQ ID NO 64
<211> LENGTH: 203
<212> TYPE: DNA
<213> ORGANISM: Glycine max

<400> SEQUENCE: 64
ttttatattt ttttatattc tattttaatt taatattttt attttttta tcctctaaat         60 taaacacacc ataagggttg aagagaggaa cggaaggaat cttgggttta aaccctccta       120
ttaatattca tattctagta ataactaaca atgattgtat ttattgaata aatgaaacaa       180
ttaataatca agagaagtca ttt                                               203

<210> SEQ ID NO 65
<211> LENGTH: 203
<212> TYPE: DNA
<213> ORGANISM: Glycine max

<400> SEQUENCE: 65
ttttatattt ttttatattc tattttaatt taatattttt attttttta tcctctaaat         60 taaacacacc ataagggttg aagagaggaa cggaaggaat cgtgggttta aaccctccta       120
ttaatattca tattctagta ataactaaca atgattgtat ttattgaata aatgaaacaa       180
ttaataatca agagaagtca ttt                                               203

<210> SEQ ID NO 66
<211> LENGTH: 20
<212> TYPE: DNA
<213> ORGANISM: Glycine max

<400> SEQUENCE: 66
aaaaatcagc acccatcgac                                                    20

<210> SEQ ID NO 67
<211> LENGTH: 20
<212> TYPE: DNA
<213> ORGANISM: Glycine max

<400> SEQUENCE: 67
```

```
agccctggcc ttattttgtt                                               20

<210> SEQ ID NO 68
<211> LENGTH: 20
<212> TYPE: DNA
<213> ORGANISM: Glycine max

<400> SEQUENCE: 68
ctctcctttc attccccaca                                               20

<210> SEQ ID NO 69
<211> LENGTH: 20
<212> TYPE: DNA
<213> ORGANISM: Glycine max

<400> SEQUENCE: 69
ttcttggagc ttcggaggta                                               20

<210> SEQ ID NO 70
<211> LENGTH: 22
<212> TYPE: DNA
<213> ORGANISM: Glycine max

<400> SEQUENCE: 70
gaactccact taatcatctc ac                                            22

<210> SEQ ID NO 71
<211> LENGTH: 21
<212> TYPE: DNA
<213> ORGANISM: Glycine max

<400> SEQUENCE: 71
ttcactccgt cctcggcggc g                                             21

<210> SEQ ID NO 72
<211> LENGTH: 37
<212> TYPE: DNA
<213> ORGANISM: Glycine max

<400> SEQUENCE: 72
atttcctaat taagtgaaag tttgaaatgt tatatta                            37

<210> SEQ ID NO 73
<211> LENGTH: 28
<212> TYPE: DNA
<213> ORGANISM: Glycine max

<400> SEQUENCE: 73
gatttatcac actatcaaag tgtatgac                                      28

<210> SEQ ID NO 74
<211> LENGTH: 20
<212> TYPE: DNA
<213> ORGANISM: Glycine max

<400> SEQUENCE: 74
tcgcaatatt ggctacgatg                                               20

<210> SEQ ID NO 75
<211> LENGTH: 26
<212> TYPE: DNA
<213> ORGANISM: Glycine max
```

```
<400> SEQUENCE: 75
ctgaaaacaa aataaaagag aacaaa                                        26

<210> SEQ ID NO 76
<211> LENGTH: 18
<212> TYPE: DNA
<213> ORGANISM: Glycine max

<400> SEQUENCE: 76
ctctgtcccc acctctcc                                                 18

<210> SEQ ID NO 77
<211> LENGTH: 18
<212> TYPE: DNA
<213> ORGANISM: Glycine max

<400> SEQUENCE: 77
catggtcagt ttgatagc                                                 18

<210> SEQ ID NO 78
<211> LENGTH: 21
<212> TYPE: DNA
<213> ORGANISM: Glycine max

<400> SEQUENCE: 78
taagtgattc gtttgagtcc t                                             21

<210> SEQ ID NO 79
<211> LENGTH: 22
<212> TYPE: DNA
<213> ORGANISM: Glycine max

<400> SEQUENCE: 79
tatggtgtgg ctatggagat tg                                            22

<210> SEQ ID NO 80
<211> LENGTH: 21
<212> TYPE: DNA
<213> ORGANISM: Glycine max

<400> SEQUENCE: 80
gcatcaacac ttggcgcaag c                                             21

<210> SEQ ID NO 81
<211> LENGTH: 24
<212> TYPE: DNA
<213> ORGANISM: Glycine max

<400> SEQUENCE: 81
ggataatgcg ataattgttc tagc                                          24

<210> SEQ ID NO 82
<211> LENGTH: 20
<212> TYPE: DNA
<213> ORGANISM: Glycine max

<400> SEQUENCE: 82
aaatatagca ccctttagag                                               20

<210> SEQ ID NO 83
<211> LENGTH: 17
<212> TYPE: DNA
<213> ORGANISM: Glycine max
```

<400> SEQUENCE: 83
agcctcactc tccacat                                                    17

<210> SEQ ID NO 84
<211> LENGTH: 22
<212> TYPE: DNA
<213> ORGANISM: Glycine max

<400> SEQUENCE: 84
tttaactgaa aatactccgg ca                                              22

<210> SEQ ID NO 85
<211> LENGTH: 24
<212> TYPE: DNA
<213> ORGANISM: Glycine max

<400> SEQUENCE: 85
tcataattta agagaccaaa ccga                                            24

<210> SEQ ID NO 86
<211> LENGTH: 23
<212> TYPE: DNA
<213> ORGANISM: Glycine max

<400> SEQUENCE: 86
ttggaattct gaaagtgttg ttg                                             23

<210> SEQ ID NO 87
<211> LENGTH: 20
<212> TYPE: DNA
<213> ORGANISM: Glycine max

<400> SEQUENCE: 87
ggaaatccaa ccccaaaaat                                                 20

<210> SEQ ID NO 88
<211> LENGTH: 21
<212> TYPE: DNA
<213> ORGANISM: Glycine max

<400> SEQUENCE: 88
gcaaacttgc atcaacttca a                                               21

<210> SEQ ID NO 89
<211> LENGTH: 20
<212> TYPE: DNA
<213> ORGANISM: Glycine max

<400> SEQUENCE: 89 tccaccttt ccaacattcc                                                  20

<210> SEQ ID NO 90
<211> LENGTH: 21
<212> TYPE: DNA
<213> ORGANISM: Glycine max

<400> SEQUENCE: 90
catattttcc gctcactttg c                                               21

<210> SEQ ID NO 91
<211> LENGTH: 23
<212> TYPE: DNA

```
<213> ORGANISM: Glycine max

<400> SEQUENCE: 91
aaattagcaa aatgcatgta ccc                                        23

<210> SEQ ID NO 92
<211> LENGTH: 20
<212> TYPE: DNA
<213> ORGANISM: Glycine max

<400> SEQUENCE: 92
tcgtcgcatg caactttta                                             20

<210> SEQ ID NO 93
<211> LENGTH: 20
<212> TYPE: DNA
<213> ORGANISM: Glycine max

<400> SEQUENCE: 93
ttagctcgca acaccatcac                                            20

<210> SEQ ID NO 94
<211> LENGTH: 20
<212> TYPE: DNA
<213> ORGANISM: Glycine max

<400> SEQUENCE: 94
aatgggttgg aaacttgcag                                            20

<210> SEQ ID NO 95
<211> LENGTH: 22
<212> TYPE: DNA
<213> ORGANISM: Glycine max

<400> SEQUENCE: 95
tgggtacgtc aaaattagga aa                                         22

<210> SEQ ID NO 96
<211> LENGTH: 20
<212> TYPE: DNA
<213> ORGANISM: Glycine max

<400> SEQUENCE: 96
ttctttgttt gacggtggtg                                            20

<210> SEQ ID NO 97
<211> LENGTH: 22
<212> TYPE: DNA
<213> ORGANISM: Glycine max

<400> SEQUENCE: 97
tgactcgaac acaaaactcc tt                                         22

<210> SEQ ID NO 98
<211> LENGTH: 20
<212> TYPE: DNA
<213> ORGANISM: Glycine max

<400> SEQUENCE: 98
tggccagaac ttgaaggaac                                            20

<210> SEQ ID NO 99
<211> LENGTH: 21
```

```
<212> TYPE: DNA
<213> ORGANISM: Glycine max

<400> SEQUENCE: 99
tgcttattat tgcaccccat t                                      21

<210> SEQ ID NO 100
<211> LENGTH: 20
<212> TYPE: DNA
<213> ORGANISM: Glycine max

<400> SEQUENCE: 100 tgatccctttt aacccagcaa                                       20

<210> SEQ ID NO 101
<211> LENGTH: 20
<212> TYPE: DNA
<213> ORGANISM: Glycine max

<400> SEQUENCE: 101
caatgacaaa aagccaacca                                        20

<210> SEQ ID NO 102
<211> LENGTH: 20
<212> TYPE: DNA
<213> ORGANISM: Glycine max

<400> SEQUENCE: 102
ttccccgatg aattatttgc                                        20

<210> SEQ ID NO 103
<211> LENGTH: 22
<212> TYPE: DNA
<213> ORGANISM: Glycine max

<400> SEQUENCE: 103
tgtgataaaa ggatccagag ca                                     22

<210> SEQ ID NO 104
<211> LENGTH: 24
<212> TYPE: DNA
<213> ORGANISM: Glycine max

<400> SEQUENCE: 104
ggtagatcca ggagcttgag tcag                                   24

<210> SEQ ID NO 105
<211> LENGTH: 24
<212> TYPE: DNA
<213> ORGANISM: Glycine max

<400> SEQUENCE: 105
gcgcatctca ctgcacttga tttt                                   24

<210> SEQ ID NO 106
<211> LENGTH: 23
<212> TYPE: DNA
<213> ORGANISM: Glycine max

<400> SEQUENCE: 106
ttcttagctg ccactattta cga                                    23

<210> SEQ ID NO 107
```

```
<211> LENGTH: 20
<212> TYPE: DNA
<213> ORGANISM: Glycine max

<400> SEQUENCE: 107
tgccatgcat acacatcctt                                                   20

<210> SEQ ID NO 108
<211> LENGTH: 21
<212> TYPE: DNA
<213> ORGANISM: Glycine max

<400> SEQUENCE: 108
ttttgccacc taattgtgtc t                                                 21

<210> SEQ ID NO 109
<211> LENGTH: 20
<212> TYPE: DNA
<213> ORGANISM: Glycine max

<400> SEQUENCE: 109
tctcacaaca ggtgagtcgg                                                   20

<210> SEQ ID NO 110
<211> LENGTH: 23
<212> TYPE: DNA
<213> ORGANISM: Glycine max

<400> SEQUENCE: 110
ccaacttgaa attactagag aaa                                               23

<210> SEQ ID NO 111
<211> LENGTH: 21
<212> TYPE: DNA
<213> ORGANISM: Glycine max

<400> SEQUENCE: 111
cttactagcg tattaaccct t                                                 21

<210> SEQ ID NO 112
<211> LENGTH: 20
<212> TYPE: DNA
<213> ORGANISM: Glycine max

<400> SEQUENCE: 112
cccattacac catgtcacca                                                   20

<210> SEQ ID NO 113
<211> LENGTH: 23
<212> TYPE: DNA
<213> ORGANISM: Glycine max

<400> SEQUENCE: 113
atccgtgtta agggatctaa ctt                                               23

<210> SEQ ID NO 114
<211> LENGTH: 20
<212> TYPE: DNA
<213> ORGANISM: Glycine max

<400> SEQUENCE: 114
ccaagtggcc taatttccaa                                                   20
```

-continued

<210> SEQ ID NO 115
<211> LENGTH: 21
<212> TYPE: DNA
<213> ORGANISM: Glycine max

<400> SEQUENCE: 115
ttcaagaaga gaaccgtgca t                                        21

<210> SEQ ID NO 116
<211> LENGTH: 24
<212> TYPE: DNA
<213> ORGANISM: Glycine max

<400> SEQUENCE: 116
gccacttgac actcaaatct actt                                     24

<210> SEQ ID NO 117
<211> LENGTH: 23
<212> TYPE: DNA
<213> ORGANISM: Glycine max

<400> SEQUENCE: 117
ataacagatt atgagttctg cag                                      23

<210> SEQ ID NO 118
<211> LENGTH: 21
<212> TYPE: DNA
<213> ORGANISM: Glycine max

<400> SEQUENCE: 118
accctctcta gaatggtgtg t                                        21

<210> SEQ ID NO 119
<211> LENGTH: 22
<212> TYPE: DNA
<213> ORGANISM: Glycine max

<400> SEQUENCE: 119
agaagaatga aaatcaccca at                                       22

<210> SEQ ID NO 120
<211> LENGTH: 24
<212> TYPE: DNA
<213> ORGANISM: Glycine max

<400> SEQUENCE: 120
gtccactaaa atgacattgt gaaa                                     24

<210> SEQ ID NO 121
<211> LENGTH: 24
<212> TYPE: DNA
<213> ORGANISM: Glycine max

<400> SEQUENCE: 121
caggtatgga tatgtatgta tcaa                                     24

<210> SEQ ID NO 122
<211> LENGTH: 21
<212> TYPE: DNA
<213> ORGANISM: Glycine max

<400> SEQUENCE: 122
atgaactcat gtgttcaatg a                                        21

-continued

```
<210> SEQ ID NO 123
<211> LENGTH: 20
<212> TYPE: DNA
<213> ORGANISM: Glycine max

<400> SEQUENCE: 123
tgcacacgtt tgaattaggg                                                  20
```

COMPOSITIONS AND METHODS TO INCREASE RESISTANCE TO PHYTOPHTHORA IN SOYBEAN

CROSS REFERENCE TO RELATED APPLICATIONS

This application is a continuation of International Application no. PCT/US2021/063556, filed on Dec. 15, 2021 which claims priority to U.S. Provisional Application Ser. No. 63/126,283, filed on Dec. 16, 2020 and U.S. Provisional Application Ser. No. 63/154,913, filed on Mar. 1, 2021, respectively, the disclosures of which are expressly incorporated herein.

REFERENCE TO SEQUENCE LISTING SUBMITTED ELECTRONICALLY

The official copy of the sequence listing is submitted electronically via EFS-Web as an ASCII formatted sequence listing with a file named 83005_Sequence-Listing_ST25349117 created on Dec. 13, 2021 and having a size of 94.7 kilobytes and is filed concurrently with the specification. The sequence listing comprised in this ASCII formatted document is part of the specification and is herein incorporated by reference in its entirety.

FIELD

This disclosure relates generally to the field of molecular biology.

BACKGROUND

Soybean diseases are major threat for soybean production, resulting in yield losses and decrease in grain quality. *Phytophthora* root and stem root (PRSR), caused by the soil-borne oomycete pathogen *Phytophthora sojae*, is one of the top five most destructive diseases leading to soybean yield loss. From 1996 to 2016, the total estimated economic loss due to PRSR was 7.4 billion USD in the United States and ranked as the third most severe soybean disease after soybean cyst nematode (SCN) and seedling disease (Bandara A Y et al. 2019). Resistance to *Phytophthora* infection is conditioned by naturally occurring variation at the Resistance to *Phytophthora sojae* (Rps) loci. As races of *Phytophthora* in the fields shift, previously effective resistance sources are breaking down, causing damage and compromised yields in grower fields.

Accordingly, there is a need to develop new compositions and methods for conferring resistance to *Phytophthora sojae*. This disclosure provides such compositions and methods.

SUMMARY

In accordance with one embodiment an isolated gene construct is provided comprising a heterologous regulatory sequence operably linked to a polynucleotide encoding a polypeptide comprising an amino acid sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 2 or 4. In one embodiment the heterologous regulatory element is a heterologous promoter. In one embodiment the isolated gene construct comprises a heterologous promoter operably linked to a polynucleotide sequence encoding a polypeptide comprising SEQ ID NOs: 2 or 4. In one embodiment the isolated gene construct comprises a heterologous promoter operably linked to a polynucleotide sequence having at least 95% sequence identity with SEQ ID NO: 1 or 3.

In one embodiment soybean plants or soybean seeds are provided comprising a targeted genetic modification increasing expression of a polynucleotide encoding a polypeptide comprising an amino acid sequence having at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 2 or 4 as compared to a control plant not comprising the targeted genetic modification. In certain embodiments, the soybean plant or a plant grown from the soybean seed comprising the targeted genetic modification has improved resistance to *Phytophthora* infection as compared to the control plant. In certain embodiments, the targeted genetic modification introduces a polynucleotide sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 1 or 3, optionally wherein said polynucleotide is operably linked to a heterologous promoter.

Further provided are plants grown from seed whose cells comprise a polynucleotide encoding a polypeptide having at least 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO: 2 or 4, and methods of plant breeding comprising crossing such soybean plants with a second soybean plant to produce a progeny seed. In certain embodiments, the second soybean plant is susceptible to the at least one race of *Phytophthora*. In certain embodiments, the progeny seed comprises the targeted genetic modification and a plant produced from the seed has increased resistance to at least one race of *Phytophthora*.

Also provided are methods for generating a *Phytophthora* resistant soybean plant comprising introducing in a regenerable soybean plant cell a polynucleotide encoding a polypeptide comprising an amino acid sequence having at least 80% sequence identity to any one of SEQ ID NOs: 2 or 4, and generating the plant wherein the plant expresses the polynucleotide and has increased resistance to *Phytophthora* as compared to a control plant not expressing the polynucleotide. In certain embodiments, the regenerable plant cell is isolated from a soybean plant susceptible to at least one race of *Phytophthora* and the plant generated has increased resistance to the at least one race of *Phytophthora*. In certain embodiments, the polynucleotide is introduced in the regenerable soybean plant cell using a targeted genetic modification Further provided are methods for generating a *Phytophthora* resistant soybean plant comprising introducing in a regenerable soybean plant cell a targeted genetic modification increasing the expression of a polynucleotide encoding a polypeptide comprising an amino acid sequence having at least 80% sequence identity to any one of SEQ ID NOs: 2 or 4, optionally at least 95% sequence identity to any one of SEQ ID NOs: 2 or 4, and generating the plant wherein the plant has increased expression of the polynucleotide and increased resistance to *Phytophthora* infection as compared to a control plant not comprising the targeted genetic modification, optionally compared to the parent plant that was used to generate the modified plant that exhibits increased expression of a polynucleotide encoding a polypeptide comprising an amino acid sequence having at least 80% sequence identity to any one of SEQ ID NOs: 2 or 4.

Also provided are soybean plants or seed comprising a recombinant DNA construct comprising a polynucleotide encoding a polypeptide comprising an amino acid sequence that is at least 80% identical to any one of SEQ ID NOs: 2 or 4, wherein the soybean seed or soybean plant has increased expression of the polynucleotide as compared to a control plant not comprising the polynucleotide, optionally wherein the DNA construct comprises a heterologous promoter operably linked to a polynucleotide encoding a polypeptide comprising an amino acid sequence that is at least 80% identical to any one of SEQ ID NOs: 2 or 4.

Further provided are methods for increasing resistance to *Phytophthora* infection in a soybean plant comprising expressing in a regenerable soybean plant cell a recombinant DNA construct comprising a polynucleotide encoding a polypeptide comprising an amino acid sequence having at least 80% sequence identity to any one of SEQ ID NOs: 2 or 4, and generating the plant wherein the plant has increased expression of the polynucleotide and increased resistance to *Phytophthora* infection as compared to a control plant not comprising the recombinant DNA construct.

Also provided are methods for identifying a soybean plant that displays increased resistance to *Phytophthora*, comprising detecting in a soybean plant or seed thereof a polynucleotide sequence encoding a polypeptide comprising an amino acid sequence that is at least 80% identical to any one of SEQ ID NOs: 2 or 4 or detecting in a soybean plant or seed thereof at least one allele of a marker locus associated with Rps11, Rps2b (also known as Rps2cas), Rps15 (also known as Rps2f), or Rps14 (also known as Rps1f).

BRIEF DESCRIPTION OF THE DRAWINGS AND THE SEQUENCE LISTING

The disclosure can be more fully understood from the following detailed description and the accompanying drawings and Sequence Listing, which form a part of this application, which are incorporated herein by reference.

FIG. 1 depicts the expression level of the twelve NBS-LRR genes across the Rps11 locus in the Rps11 donor line.

Figure 2:
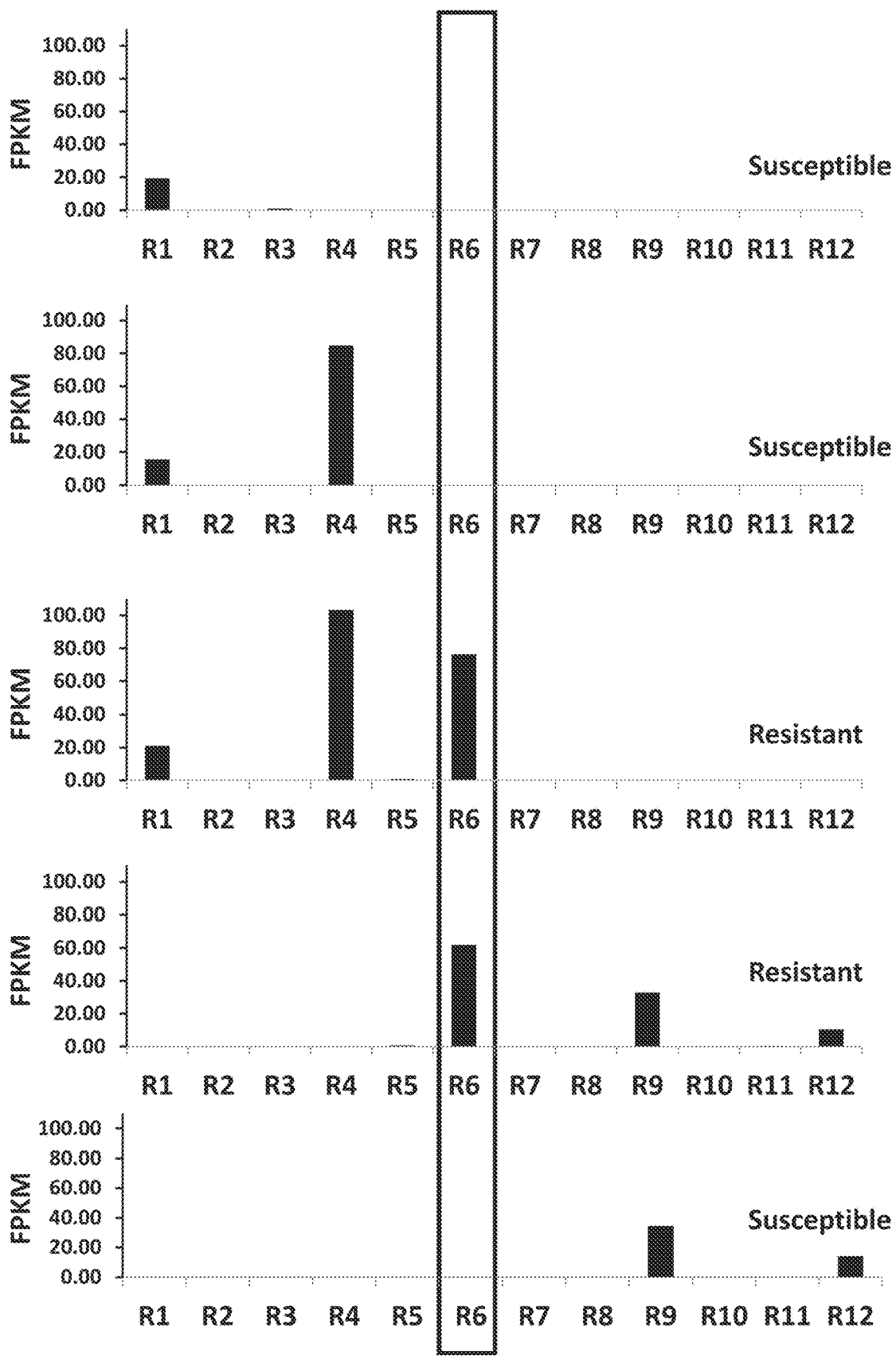

FIG. 2 provides experimental results depicting the expression profile of the NBS-LRR genes in 9 recombinants. The y-axis is the expression value in Fragments per Kilobase per Million mapped reads (FPKM) and the x-axis is the code of twelve NBS-LRR genes at Rps11 locus. The phenotype (i.e., susceptible or resistant) of each recombinant is listed and recombinants with the same expression pattern are combined together.

Figure 3:
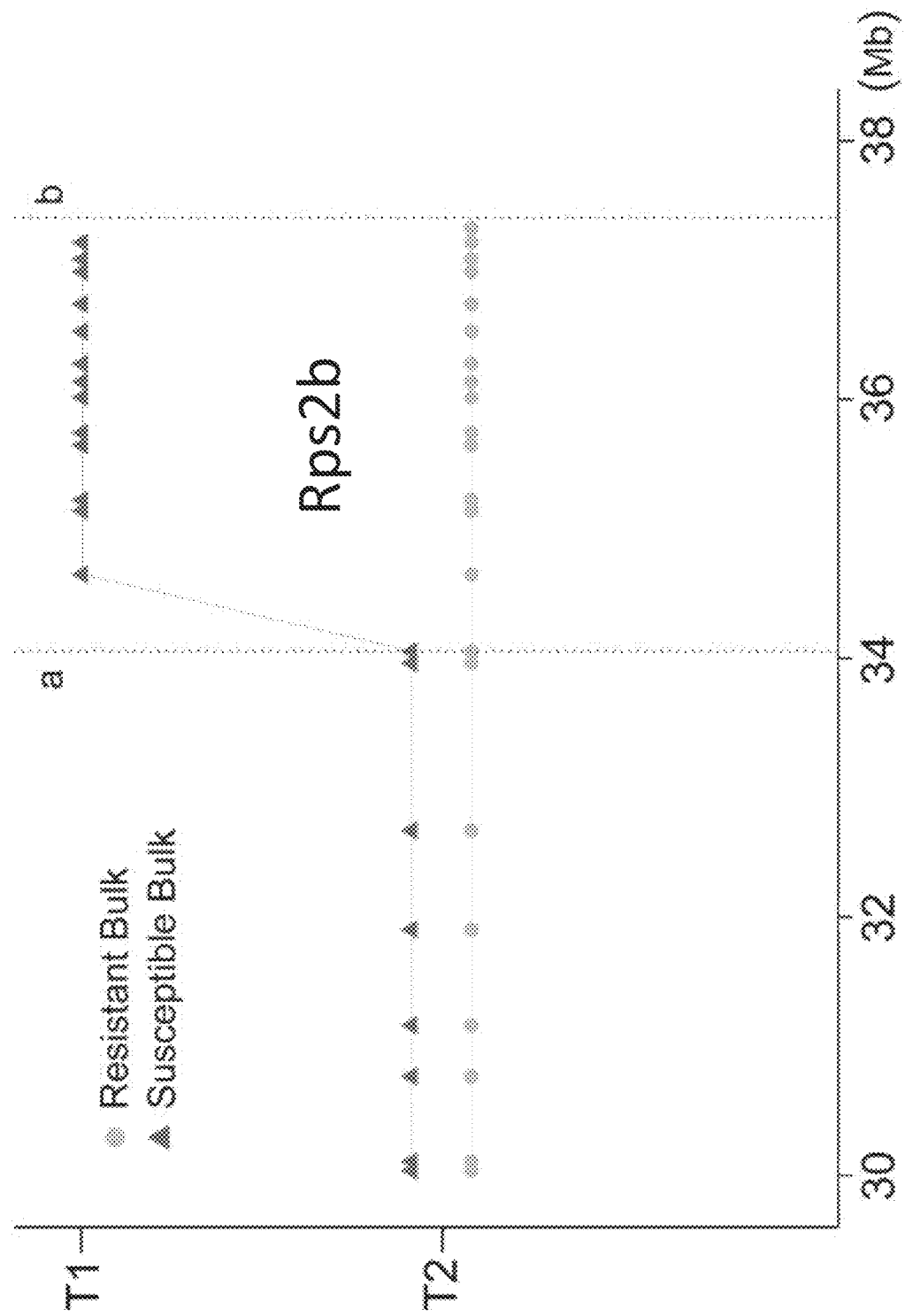

FIG. 3 provides experimental results showing the initial mapping of Rp2cas from the bulked segregant analysis (BSA). Triangles represent the genotypes of the susceptible bulk at the SNP sites between the two parental lines, while circles are genotypes of the resistant bulk at the same set of SNP sites. The x-axis shows the physical positions of these SNP sites along chromosome 16. On the y-axis, the T1 position represents the homozygous genotype detected in the susceptible bulk, and the T2 position indicates the heterozygous genotypes that were detected in susceptible or/and resistant bulks. Dotted vertical lines a and b define the two boundaries of the Rps2b region from initial BSA mapping.

Figure 4:
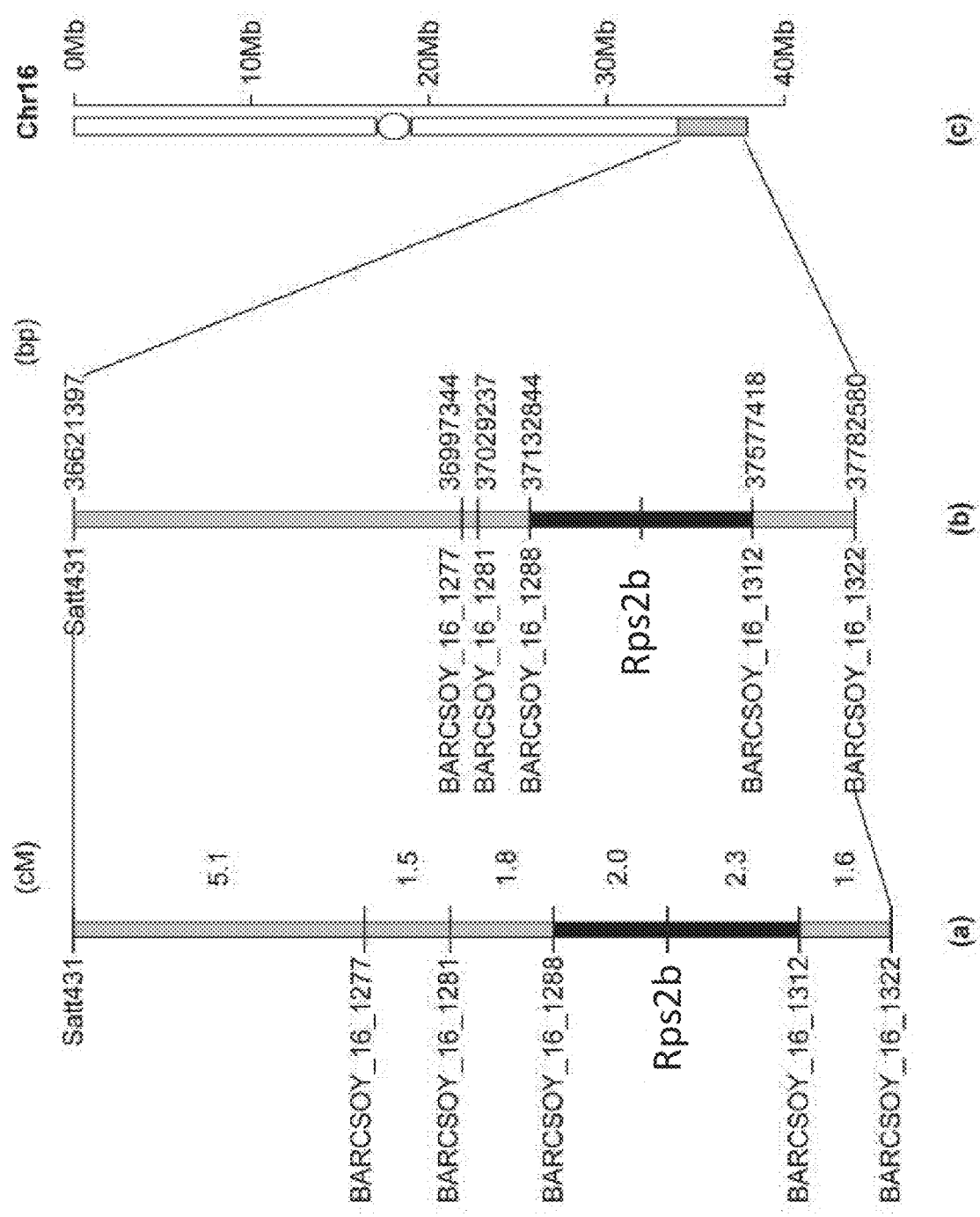

FIG. 4 provides the genetic and physical map of the Rps2b region. The left bar (a) provides the genetic map of the Rps2b region according to linkage analysis. SSR markers are listed on the left side and the genetic distance (centimorgan, cM) between adjacent markers are shown on the right side of the map. The middle bar (b) provides the physical positions of molecular markers on chromosome 16 based on soybean reference genome (Wms82 v2.1). Both genetic and physical regions of Rps2b defined by the two most closely linked markers are marked with solid dark bars. The right bar (c) provides the physical location of the Rps2b initial mapping region on Chromosome 16 based on BSA analysis. The Circle represents approximate position of centromere, whereas the two bars connected to centromere represent two arms of chromosome.

Figure 5A:
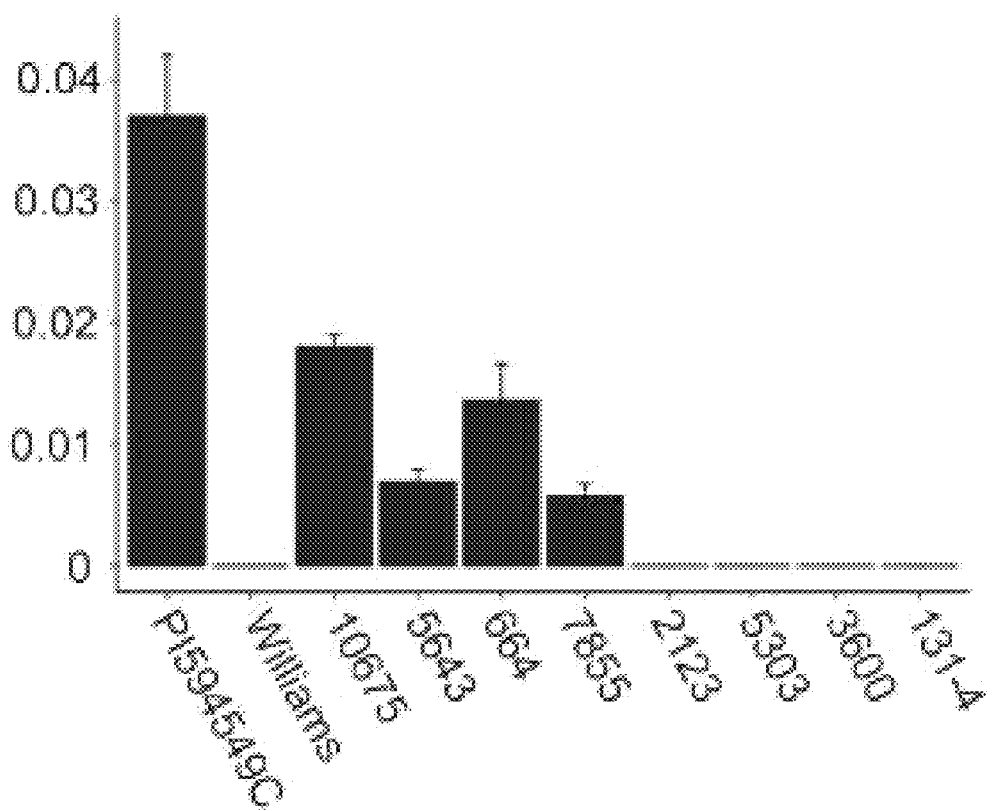
Figure 5B:
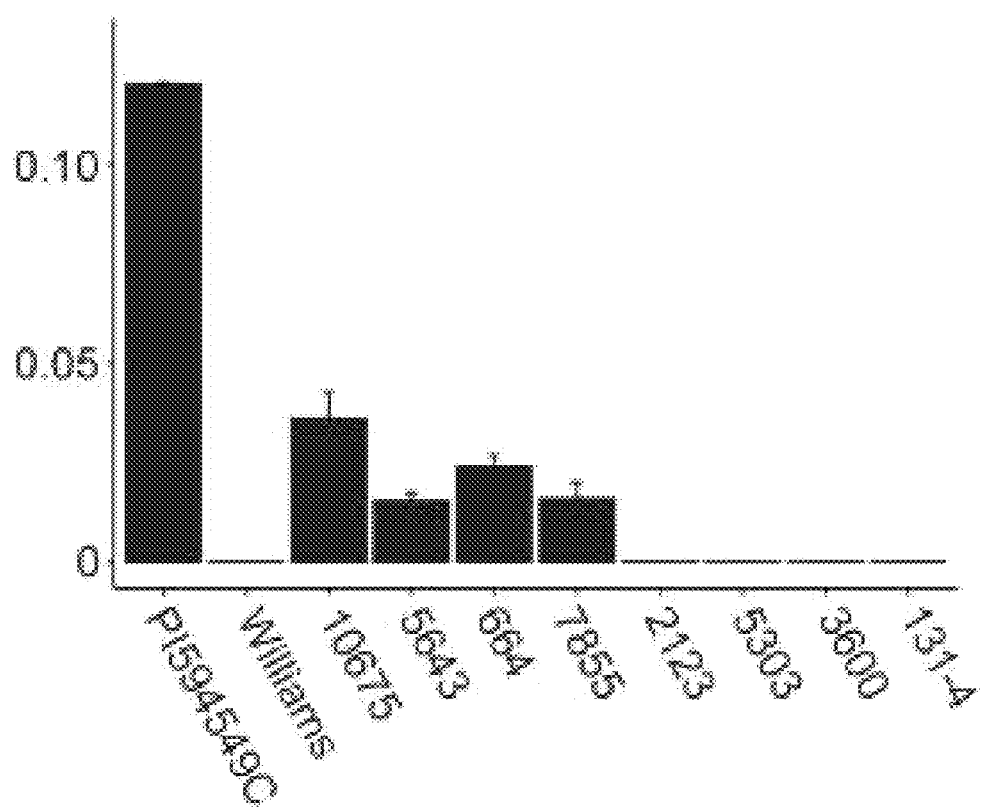
Figure 5C:
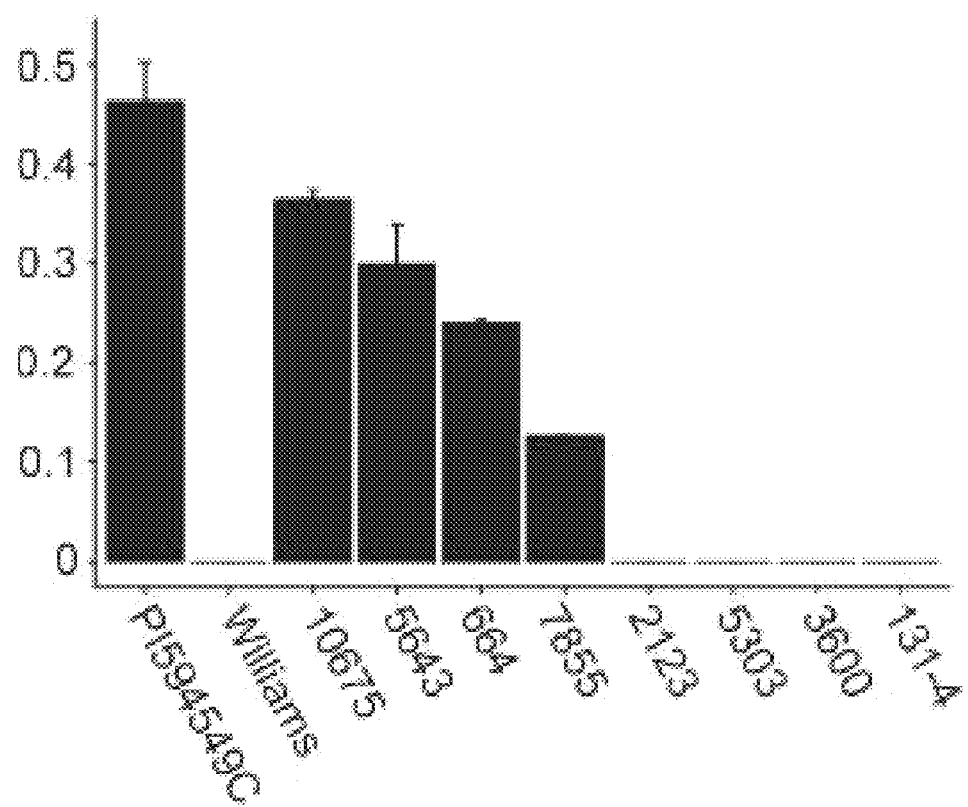

FIGS. 5A-5C provide the experimental results showing the expression pattern of the 3 tested Rps2b locus R-genes in the recombinants. The phenotype of first four recombinants (10675, 5643, 664, 7855) are all heterozygous resistance, while the phenotypes of the last four recombinants (2123, 5303, 3600, 131-4) are all susceptible. FIG. 5A provides the results of Rps2b R-gene2. FIG. 5B provides the results of Rps2b R-gene3. FIG. 5C provides the results of Rps2b R-gene4.

Figure 6A:
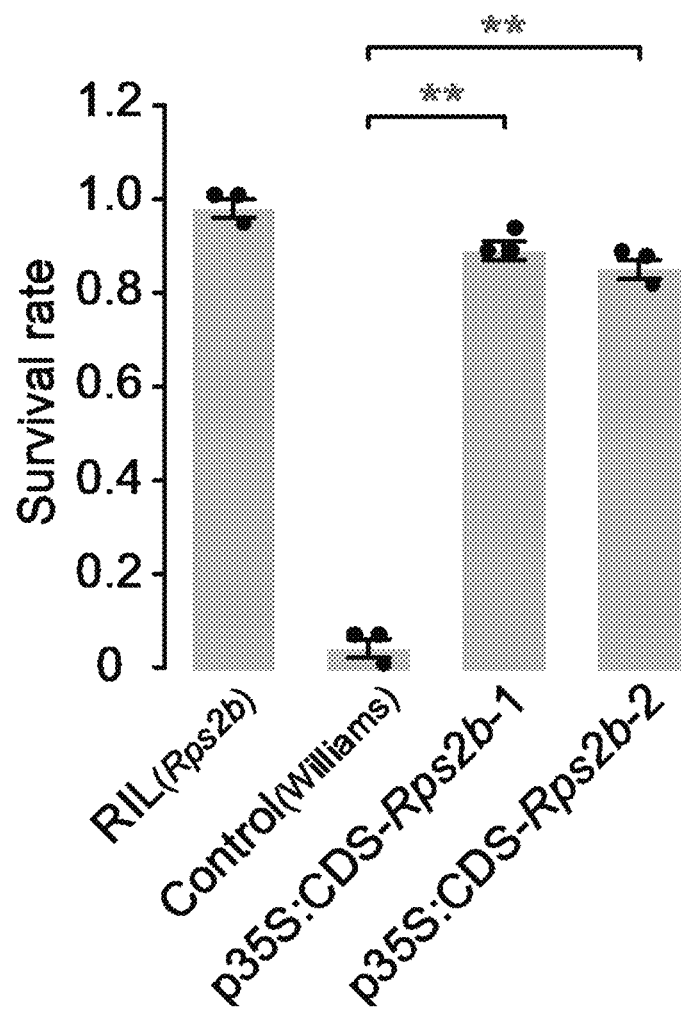
Figure 6B:
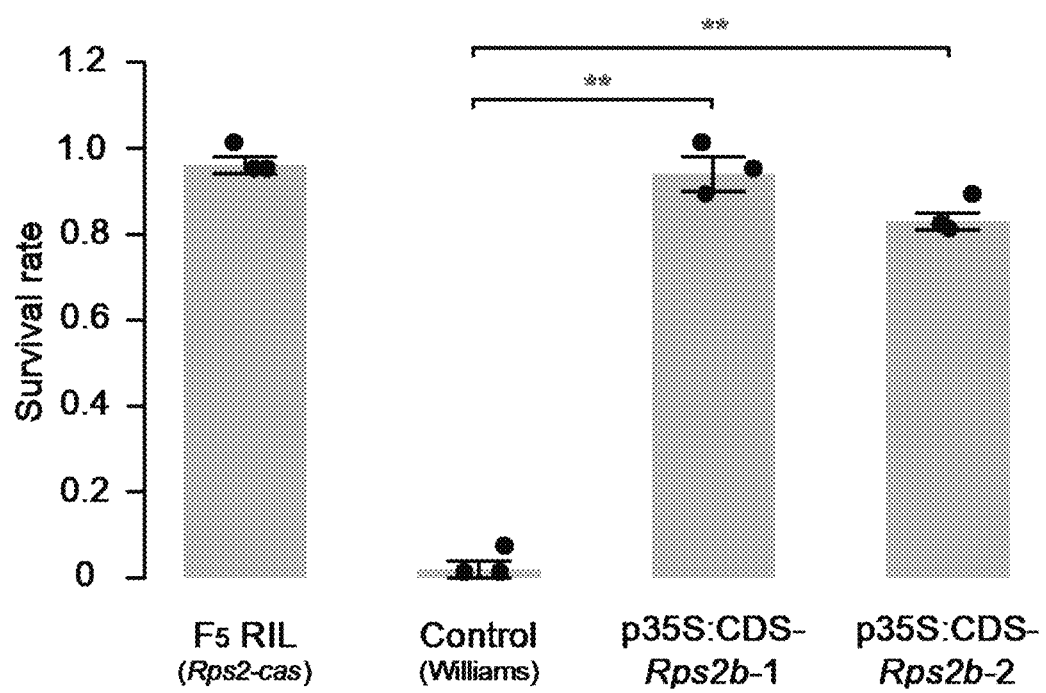

FIGS. 6A and 6B provide graphs of experimental results of a complementation test to *P. sojae* Race 1 (FIG. 6A) and Race 25 (FIG. 6B) in transgenic soybean plants expressing the Rps2b gene, soybean variety $F_5$ RIL (positive control line), or soybean Williams (negative control).

Figure 6C:
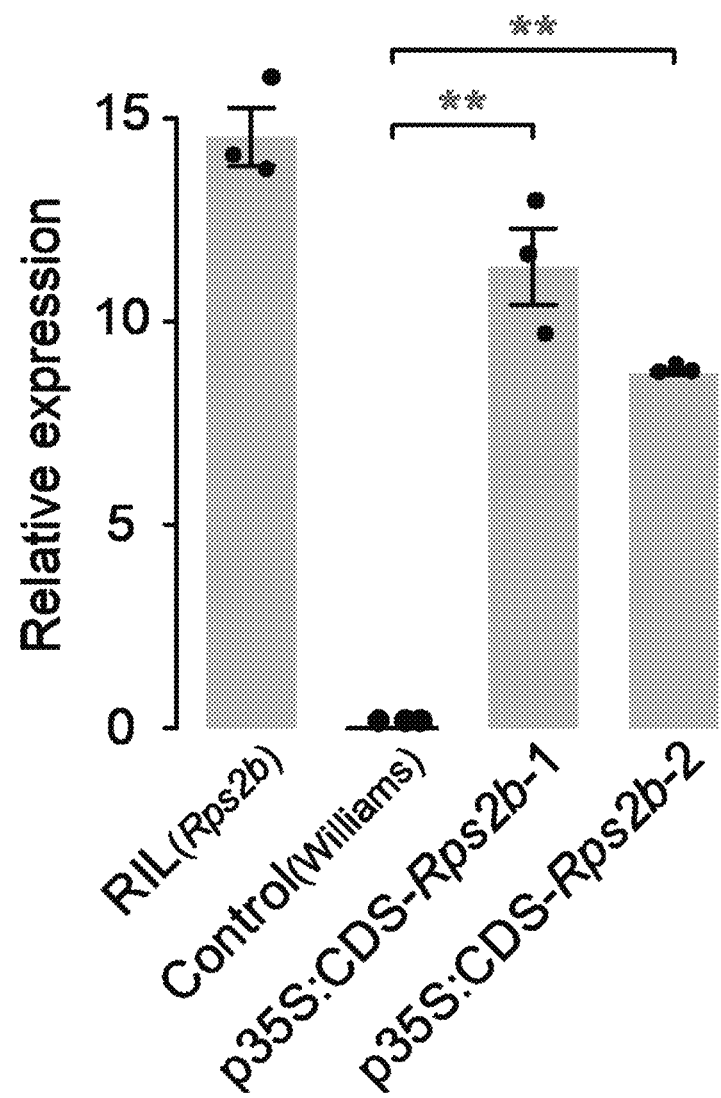

FIG. 6C provides a graph of experimental results providing the relative expression level of Rps2b in the transgenic soybean plants expressing the Rps2b gene, the soybean variety $F_5$ RIL (positive control line), and the soybean Williams (negative control).

Figure 7:
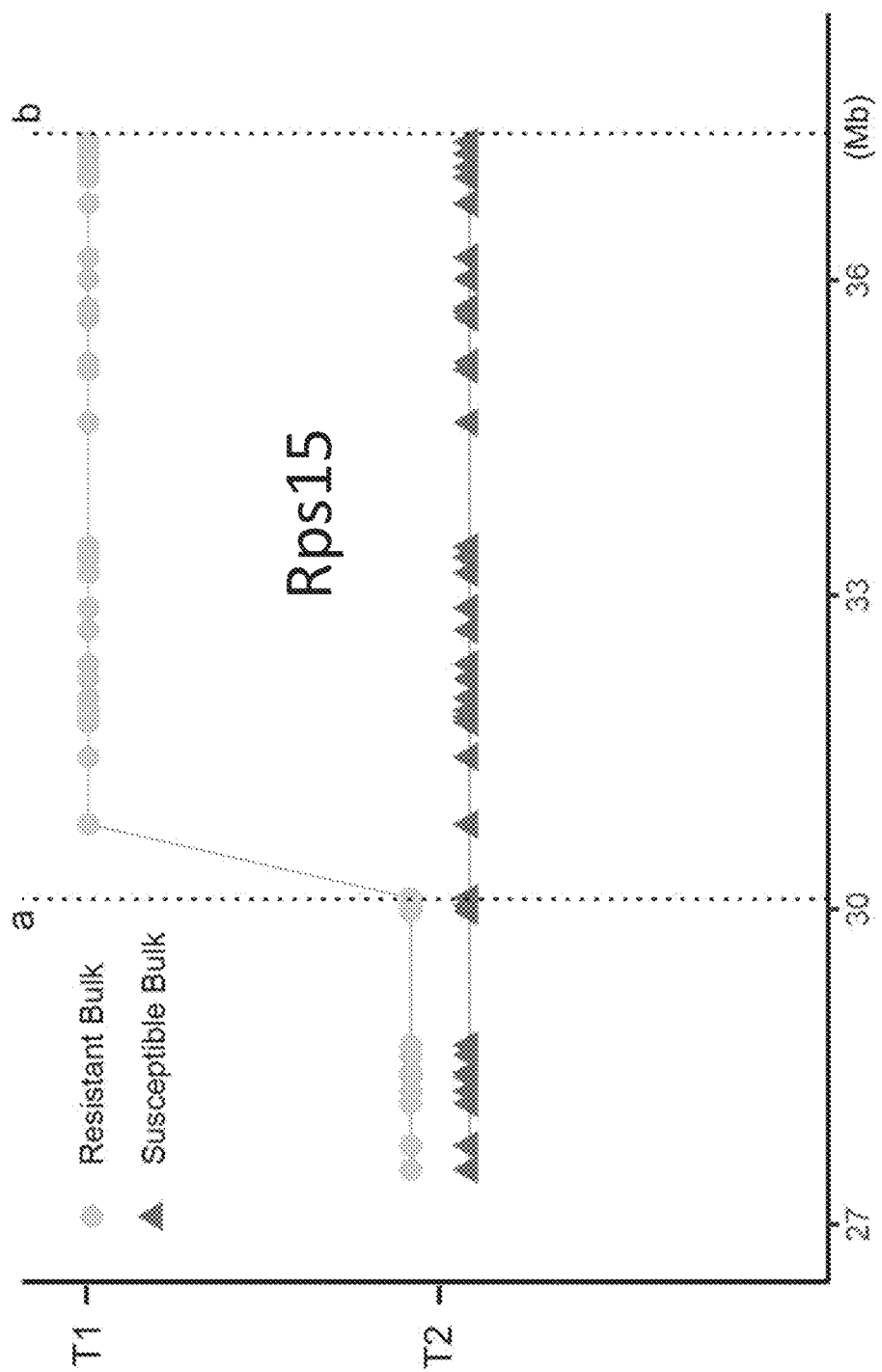

FIG. 7 provides experimental results depicting the initial mapping of Rps15 from the bulked segregant analysis (BSA). Circles represent the genotypes of the resistant bulk at the SNP sites between the two parental lines, while triangles are the genotypes of the susceptible bulk at the same set of SNP sites. The x-axis shows the physical positions of these SNP sites along chromosome 16 and on the y-axis, the T1 position represents homozygous genotype detected in the resistant bulk, and the T2 position indicates the heterozygous genotypes that were detected in susceptible or/and resistant bulks. Dotted vertical line a and b define two boundaries of Rps15 region from initial BSA mapping.

Figure 8:
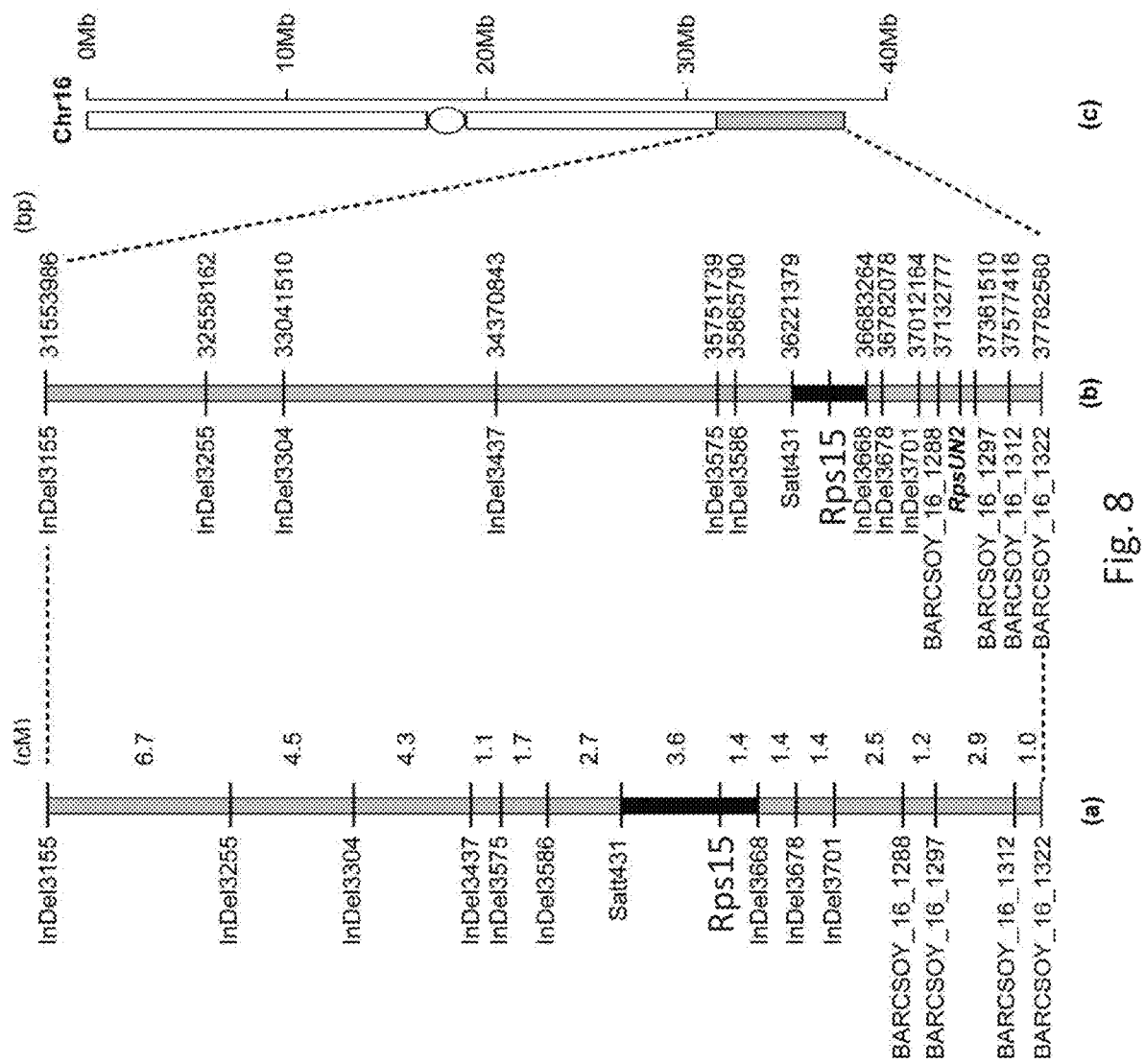

FIG. 8 provides the genetic and physical map of the Rps15 region. The left bar (a) provides a genetic map of the Rps15 region according to linkage analysis. Molecular markers (SSR/InDels) are listed on the left side and the genetic distance (centimorgan, cM) between adjacent markers are shown on the right side of the map. The center bar (b) provides the physical positions of molecular markers on chromosome 16 based on soybean reference genome (Wms82 v2.1). Both genetic and physical regions of Rps15 defined by two most closely linked markers are marked with solid dark bars. Fine mapping region of RpsUN2 is within the region defined by BARCSOY_16_1288 and BARCSOY_16_1297 (Li et al. 2016). The right bar (c) provides the physical location of the Rps15 initial mapping region on Chromosome 16 based on BSA analysis. Circle represents approximate position of centromere, whereas two bars connected to centromere represent two arms of chromosome.

Figure 9:
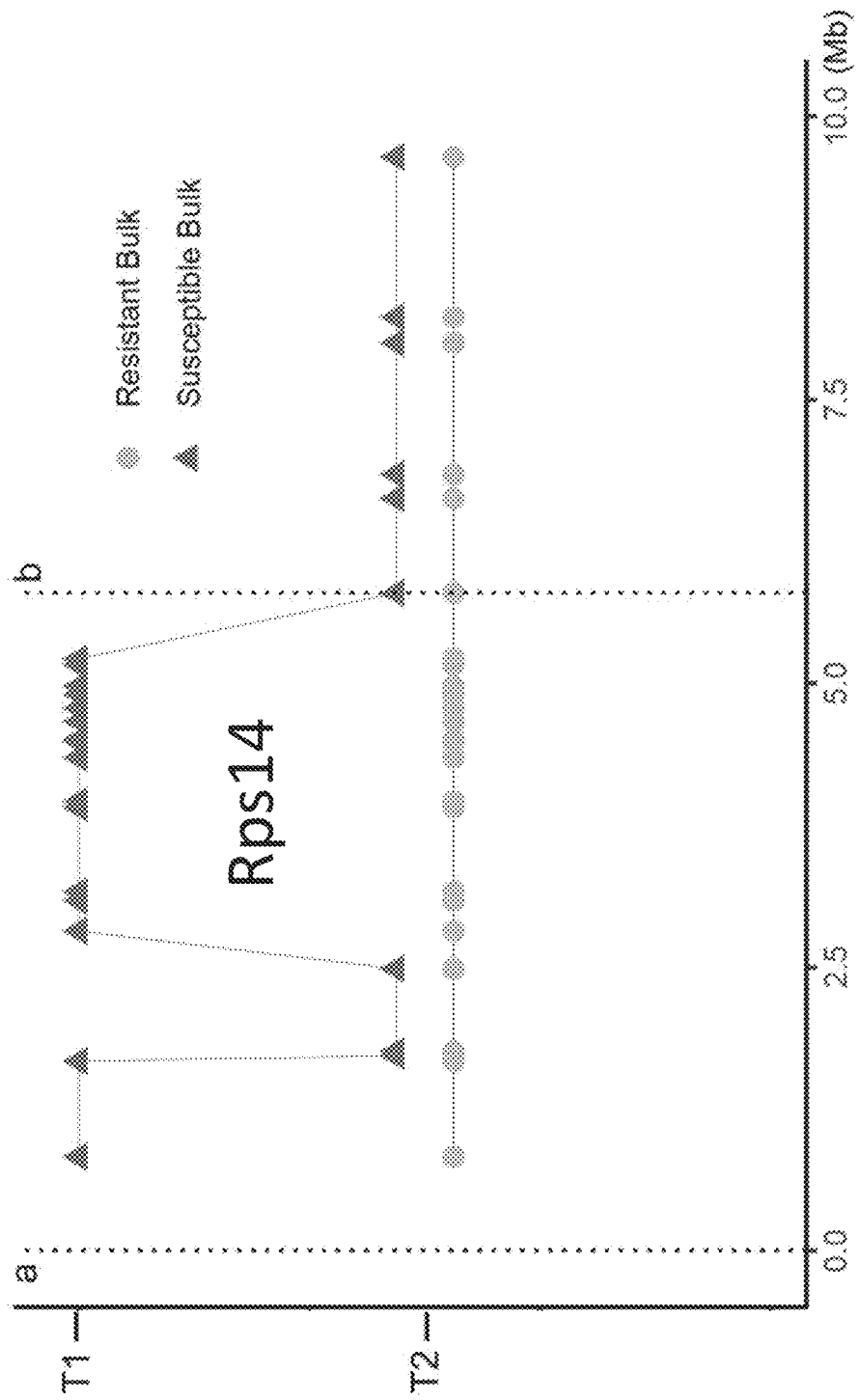

FIG. 9 provides experimental results depicting the initial mapping of Rplf from bulked segregant analysis (BSA). Circles represent the genotypes of the resistant bulk at the SNP sites between the two parental lines, while triangles are genotypes of the susceptible bulk at the same set of SNP sites. The x-axis shows the physical positions of these SNP sites along chromosome 3 and on the y-axis, the T1 position represents homozygous genotype detected in the susceptible bulk, and the T2 position indicates the heterozygous genotypes that were detected in susceptible or/and resistant bulks. Dotted vertical line a and b define two boundaries of Rps14 region from initial BSA mapping.

Figure 10:
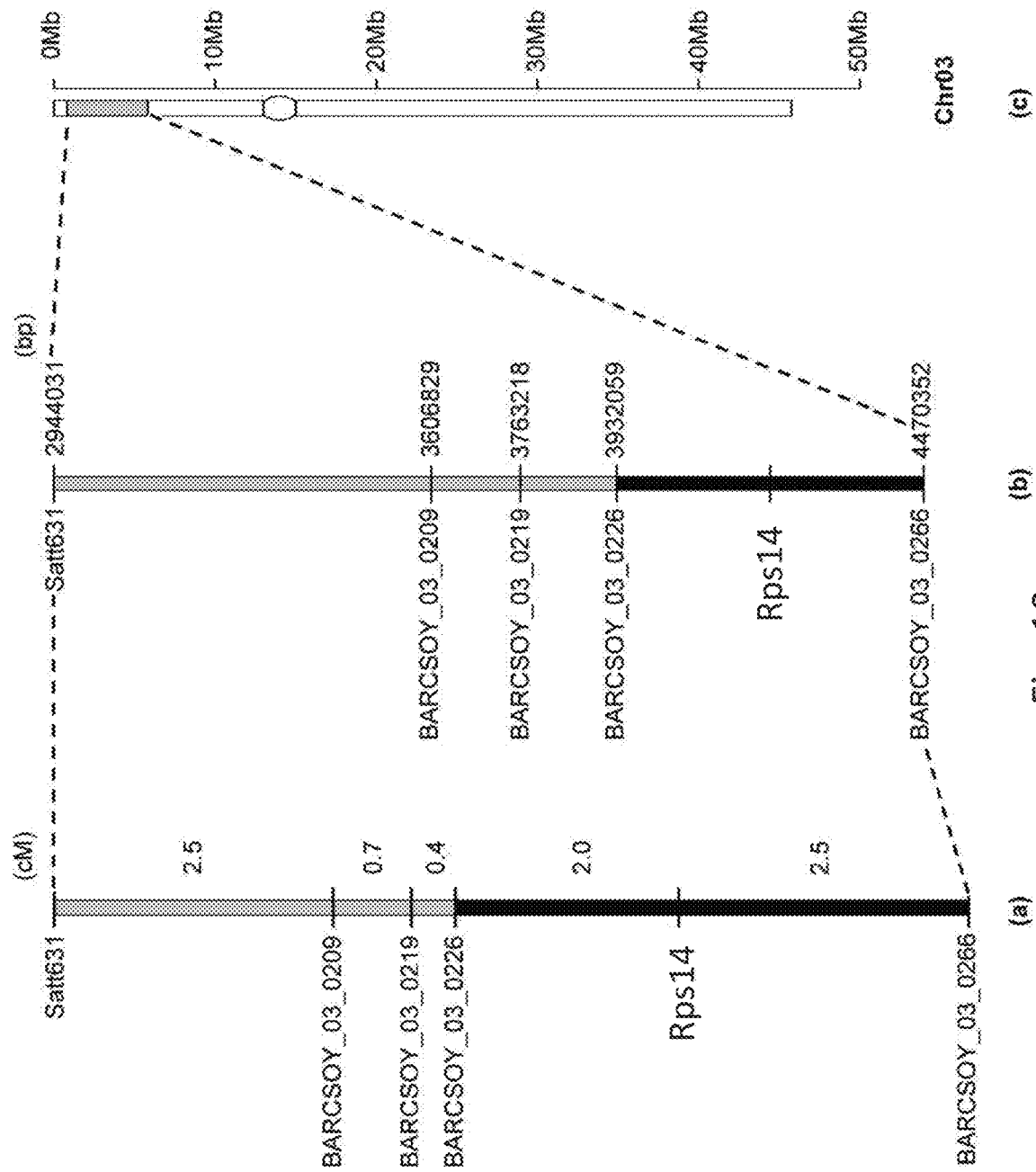

FIG. 10 provides the genetic and physical map of the Rps14 region. The left bar (a) provides the genetic map of the Rps14 region according to linkage analysis. SSR markers are listed on the left side and the genetic distance (centimorgan, cM) between adjacent markers are shown on the right side of the map. The middle bar (b) provides the physical positions of molecular markers on chromosome 3 based on soybean reference genome (Wms82 v2.1). Both genetic and physical regions of Rps14 defined by two most closely linked markers are marked with solid dark bars. The right bar (c) provides the physical location of the Rps14 initial mapping region on Chromosome 3 based on BSA analysis. The circle represents approximate position of centromere, whereas the two bars connected to centromere represent the two arms of the chromosome.

The sequence descriptions summarize the Sequence listing attached hereto, which is hereby incorporated by reference and as indicated below in Table 1. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

TABLE 1

Sequence Listing Description

| Polynucleotide SEQ ID NO: | Polypeptide SEQ ID NO: | Name |
| --- | --- | --- |
| 1 | 2 | Rps11 |
| 3, 5 | 4 | Rps2b |
| 6, 8 | 7 | Rps2b-Rgene2 |
| 9, 11 | 10 | Rps2b-Rgene4 |
| 12 | | Rps11 forward primer |
| 13 | | Rps11 reverse primer |
| 14 | | Rps2b forward primer |
| 15 | | Rps2b reverse primer |
| 16 | | Rps2b-Rgene2 forward primer |
| 17 | | Rps2b-Rgene2 reverse primer |
| 18 | | Rps2b-Rgene4 forward primer |
| 19 | | Rps2b-Rgene4 reverse primer |
| 20 | | Satt431_F |
| 21 | | Satt431_R |
| 22 | | BARCSOYSSR_16_1277_F |
| 23 | | BARCSOYSSR_16_1277_R |
| 24 | | BARCSOYSSR_16_1281_F |
| 25 | | BARCSOYSSR_16_1281_R |
| 26 | | BARCSOYSSR_16_1288_F |
| 27 | | BARCSOYSSR_16_1288_R |
| 28 | | BARCSOYSSR_16_1294_F |
| 29 | | BARCSOYSSR_16_1294_R |
| 30 | | BARCSOYSSR_16_1297_F |
| 31 | | BARCSOYSSR_16_1297_R |
| 32 | | BARCSOYSSR_16_1312_F |
| 33 | | BARCSOYSSR_16_1312_R |
| 34 | | BARCSOYSSR_16_1322_F |
| 35 | | BARCSOYSSR_16_1322_R |
| 36 | | MappingMarker-KASP-Gm16_36635129_A_G_Susceptible |
| 37 | | MappingMarker-KASP-Gm16_36635129_A_G_Resistant |
| 38 | | MappingMarker-KASP-Gm16_36641187_T_A_Susceptible |
| 39 | | MappingMarker-KASP-Gm16_36635129_A_G_Resistant |
| 40 | | MappingMarker-KASP-Gm16_36687038_T_C_Susceptible |
| 41 | | MappingMarker-KASP-Gm16_36687038_T_C_Resistant |
| 42 | | MappingMarker-KASP-Gm16_36742320_G_A_Susceptible |
| 43 | | MappingMarker-KASP-Gm16_36742320_G_A_Resistant |
| 44 | | MappingMarker-KASP-Gm16_36745870_T_C_Susceptible |
| 45 | | MappingMarker-KASP-Gm16_36745870_T_C_Resistant |
| 46 | | MappingMarker-KASP-Gm16_36789567_C_T_Susceptible |
| 47 | | MappingMarker-KASP-Gm16_36789567_C_T_Resistant |
| 48 | | MappingMarker-KASP-Gm16_36805209_C_G_Susceiptble |
| 49 | | MappingMarker-KASP-Gm16_36805209_C_G_Resistant |
| 50 | | MsppingMarker-KASP-Gm16_36818299_T_A_Susceptible |
| 51 | | MappingMarker-KASP-Gm16_36818299_T_A_Resistant |
| 52 | | MappingMarker-KASP-Gm16_36825046_C_T_Susceptible |
| 53 | | MappingMarker-KASP-Gm16_36825046_C_T_Resistant |
| 54 | | MappingMarker-KASP-Gm16_36840817_A_G_Susceptible |
| 55 | | MappingMarker-KASP-Gm16_36840817_A_G_Resistant |
| 56 | | MappingMarker-KASP-Gm16_36844181_C_T_Susceptible |
| 57 | | MappingMarker-KASP-Gm16_36844181_C_T_Resistant |
| 58 | | MappingMarker-KASP-Gm16_36849203_G_A_Susceptible |
| 59 | | MappingMarker-KASP-Gm16_36849203_G_A_Resistant |
| 60 | | MappingMarker-KASP-Gm16_36854790_A_T_Susceptible |
| 61 | | MappingMarker-KASP-Gm16_36854790_A_T_Resistant |
| 62 | | MappingMarker-KASP-Gm16_36870179_G_C_Susceptible |
| 63 | | MappingMarker-KASP-Gm16_36870179_G_C_Resistant |
| 64 | | MappingMarker-KASP-Gm16_36889339_T_G_Susceptible |

TABLE 1-continued

Sequence Listing Description

| Polynucleotide SEQ ID NO: | Polypeptide SEQ ID NO: | Name |
|---|---|---|
| 65 | | MappingMarker-KASP-Gm16_36889339_T_G_Resistant |
| 66 | | MappingMarker-SSR-07-286F |
| 67 | | MappingMarker-SSR-07-286R |
| 68 | | MappingMarker-SSR-07-295F |
| 69 | | MappingMarker-SSR-07-295R |
| 70 | | MappingMarker-InDel-626F |
| 71 | | MappingMarker-InDel-626R |
| 72 | | MappingMarker-InDel-5UTR-43F |
| 73 | | MappingMarker-InDel-5UTR-43R |
| 74 | | MappingMarker-SSR-07-300F |
| 75 | | MappingMarker-SSR-07-300R |
| 76 | | MappingMarker-176kb-F |
| 77 | | MappingMarker-176kb-R |
| 78 | | MappingMarker-InDel-327kb-F |
| 79 | | MappingMarker-InDel-327kb-R |
| 80 | | MappingMarker-InDel-5.922-F |
| 81 | | MappingMarker-InDel-5.922-R |
| 82 | | MappingMarker-InDel-6.036-F |
| 83 | | MappingMarker-InDel-6.036-R |
| 84 | | MappingMarker-SSR-07-320F |
| 85 | | MappingMarker-SSR-07-320R |
| 86 | | InDel3155-F |
| 87 | | InDel3155-R |
| 88 | | InDel3255-F |
| 89 | | InDel3255-R |
| 90 | | InDel3304-F |
| 91 | | InDel3304-R |
| 92 | | InDel3437-F |
| 93 | | InDel3437-R |
| 94 | | InDel3575-F |
| 95 | | InDel3575-R |
| 96 | | InDel3568-F |
| 97 | | InDel3568-R |
| 98 | | InDel3668-F |
| 99 | | InDel3668-R |
| 100 | | InDel3678-F |
| 101 | | InDel3678-R |
| 102 | | InDel3701-F |
| 103 | | InDel3701-R |
| 104 | | Satt631-F |
| 105 | | Satt631-R |
| 106 | | BARCSOYSSR_03_0209-F |
| 107 | | BARCSOYSSR_03_0209-R |
| 108 | | BARCSOYSSR_03_0219-F |
| 109 | | BARCSOYSSR_03_0219-R |
| 110 | | BARCSOYSSR_03_0226-F |
| 111 | | BARCSOYSSR_03_0226-R |
| 112 | | BARCSOYSSR_03_0229-F |
| 113 | | BARCSOYSSR_03_0229-R |
| 114 | | BARCSOYSSR_03_0266-F |
| 115 | | BARCSOYSSR_03_0266-R |
| 116 | | InDel3971-F |
| 117 | | InDel3971-R |
| 118 | | InDel4033-F |
| 119 | | InDel4033-R |
| 120 | | InDel4263-F |
| 121 | | InDel4263-R |
| 122 | | InDel4330-F |
| 123 | | InDel4330-R |

DETAILED DESCRIPTION

I. Compositions

A. Rps Polynucleotides and Polypeptides

One aspect of the disclosure provides a polynucleotide encoding a resistant to *Phytophthora sojae* (Rps) polypeptide comprising an amino acid sequence that is at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2, 4, 7 or 10.

As used herein "encoding," "encoded," or the like, with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma capri-*

*colum* (Yamao, et al., (1985) *Proc. Natl. Acad. Sci. USA* 82:2306-9) or the ciliate *Macronucleus*, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) *Nucleic Acids Res.* 17:477-98 and herein incorporated by reference).

The terms "polypeptide," "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

As used herein "percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

Unless otherwise stated, sequence identity/similarity values provided herein refer to the value obtained using the BLAST 2.0 suite of programs using default parameters (Altschul, et al., (1997) Nucleic Acids Res. 25:3389-402).

B. Recombinant DNA Construct

Also provided is a recombinant DNA construct comprising any of the Rps polynucleotides described herein. In certain embodiments, the recombinant DNA construct further comprises at least one regulatory element. In certain embodiments, the at least one regulatory element of the recombinant DNA construct comprises a promoter. In certain embodiments, the promoter is the native Rps polynucleotide promoter sequence. In certain embodiments, the promoter is heterologous to the Rps polynucleotide sequence.

As used herein, a "recombinant DNA construct" comprises two or more operably linked DNA segments, preferably DNA segments that are not operably linked in nature (i.e., heterologous). Non-limiting examples of recombinant DNA constructs include a polynucleotide of interest operably linked to regulatory elements, which aid in the expression, autologous replication, and/or genomic insertion of the sequence of interest. Such regulatory elements include, for example, promoters, expression modulating elements (EMEs), termination sequences, enhancers, etc., or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

The Rps polynucleotides described herein can be provided in expression cassettes for expression in a plant of interest or any organism of interest. The cassette can include 5' and 3' regulatory sequences operably linked to a Rps polynucleotide. "Operably linked" is intended to mean a functional linkage between two or more elements. For, example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the Rps polynucleotide to be under the transcriptional regulation of the regulatory regions. The expression cassette may additionally contain selectable marker genes.

The expression cassette can include in the 5'-3' direction of transcription, a transcriptional and translational initiation region (e.g., a promoter), a Rps polynucleotide, and a transcriptional and translational termination region (e.g., termination region) functional in plants. The regulatory regions (e.g., promoters, transcriptional regulatory regions, and translational termination regions) and/or the Rps polynucleotide may be native/analogous to the host cell or to each other. Alternatively, the regulatory regions and/or the Rps polynucleotide may be heterologous to the host cell or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide that is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region, with the plant host, or may be derived from another source (i.e., foreign or heterologous) than the promoter, the Rps polynucleotide, the plant host, or any combination thereof.

The expression cassette may additionally contain a 5' leader sequences. Such leader sequences can act to enhance translation. Translation leaders are known in the art and include viral translational leader sequences.

In preparing the expression cassette, the various DNA fragments may be manipulated, to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

As used herein "promoter" refers to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such Agrobacterium or Rhizobium. Certain types of promoters preferentially initiate transcription in certain tissues, such as leaves, roots, seeds, fibres, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026); GOS2 (U.S. Pat. No. 6,504,083), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Also contemplated are synthetic promoters which include a combination of one or more heterologous regulatory elements.

The promoter of the recombinant DNA constructs described herein can be any type or class of promoter known in the art, such that any one of a number of promoters can be used to express the various Rps polynucleotide sequences disclosed herein, including the native promoter of the polynucleotide sequence of interest. The promoters for use in the recombinant DNA constructs of the invention can be selected based on the desired outcome.

In certain embodiments, the recombinant DNA construct, described herein, is expressed in a plant or seed. In certain embodiments, the plant or seed is a soybean plant or soybean seed. The polynucleotides or recombinant DNA constructs disclosed herein may be used for transformation of any plant species.

C. Plants and Plant Cells

Provided are plants, plant cells, plant parts, seeds, and grain comprising at least one of the Rps polynucleotide sequences or recombinant DNA constructs, described herein, so that the plants, plant cells, plant parts, seeds, and/or grain express any of the Rps polypeptides described herein. In certain embodiments, the plants, plant cells, plant parts, seeds, and/or grain have stably incorporated at least one Rps polynucleotide described herein into its genome. In certain embodiments, the plants, plant cells, plant parts, seeds and grain are soybean plants, plant cells, plant parts, seeds and grain. In certain embodiments, the plants, plant cells, plant parts, seeds, and/or grain can comprise multiple Rps polynucleotides (i.e., at least 1, 2, 3, 4, 5, 6 or more).

Also provided are plants, plant cells, plant parts, seeds, and grain comprising a targeted genetic modification increasing expression of a polynucleotide encoding a polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 2, 4, 7 or 10 as compared to a control plant not comprising the targeted genetic modification. In certain embodiments, the plants, plant cells, plant parts, seeds and grain are soybean plants, plant cells, plant parts, seeds and grain. In certain embodiments, the plant (e.g., soybean plant) comprising the targeted genetic modification has improved resistance to Phytophthora infection as compared to the control plant. In certain embodiments, the targeted genetic modification comprises the insertion of a polynucleotide sequence comprising and one of SEQ ID NOs: 1, 3, 6 and 9 into the genome of the plant.

"Phytophthora", "Phtophthora sojae", and "P. sojae" are used interchangeably herein and refer to the soil-born oomycete pathogen that is the causative agent for Phytophthora root and stem rot.

As used herein "increasing expression" "increased expression" or the like refers to any detectable increase in the level of the polynucleotide or encoded polypeptide as compared to a control plant (e.g., non-modified plant). The level of expression can be measure using routine methods known in the art such as PCR, Western blotting, mass spectrometry, and ELISA.

As used herein, a "targeted" genetic modification or "targeted" DNA modification, refers to the direct manipulation of an organism's genes. The targeted modification may be introduced using any technique known in the art, such as, for example, plant breeding, genome editing, or single locus conversion.

The DNA modification of the genomic locus may be done using any genome modification technique known in the art or described herein. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In certain embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

As used herein, the term "plant" includes plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like.

Grain is intended to mean the mature seed produced by commercial growers for purposes other than growing or reproducing the species. Progeny, variants, and mutants of the regenerated plants are also included within the scope of the disclosure, provided that these parts comprise the introduced polynucleotides.

Also provided are plants, plant cells, plant parts, seeds, and grain comprising a polynucleotide encoding a Rps polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 2, 4, 7 or 10 operably linked to a regulatory element. In certain embodiments, the regulatory element is the native Rps promoter sequence. In certain embodiments, the regulatory element is a heterologous regulatory element, such as, for example, a heterologous promoter.

In certain embodiments, the plants described herein (e.g., plants comprising an Rps polynucleotide described herein) have a yield of soybean seeds by weight at 13% moisture that is at least 80%, 81%, 82%, 83%, 84%, 85%, 86%, 87%, 88%, 89%, 90%, 91%, 92%, 93%, 94%, 95%, 96%, 97%, 98% 99%, 100%, 101%, 102%, 103%, 104%, 105%, 106%, 107%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134% or 135% and less than 250%, 240%, 203%, 220%, 210%, 200%, 195%, 190%, 185%, 180%, 175%, 170%, 165%, 160%, 155%, 150%, 145% or 140% of the yield of seeds by weight of soybean variety 93B83 (U.S. Pat. No. 5,792,909), when grown under the same environmental conditions. Representative seed of soybean variety 93B83 were deposited under ATCC Accession No. 209766 on Apr. 10, 1998. As used herein, "under the same environmental conditions" means the plants are grown in proximity in the field or a greenhouse under non-stress conditions suitable for growth of a soybean plant to maturity, with the plants being exposed to the same environment and seeds harvested from each plant at maturity growth stage R8.

Applicant has made a deposit of at least 2500 seeds of Soybean Variety 93B83 with the American Type Culture Collection (ATCC), 10801 University Boulevard, Manassas, Va. 20110 USA, as ATCC Deposit No. 209766. The seeds were deposited with the ATCC on Apr. 10, 1998 have been accepted under the Budapest Treaty. This deposit of the Soybean Variety 93B83 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§ 1.801-1.809. Upon allowance of any claims in the application, the Applicant(s) will maintain and will make this deposit available to the public pursuant to the Budapest Treaty.

As used herein, "yield" refers to the amount of agricultural production harvested per unit of land and may include reference to bushels per acre or kilograms per hectare of a crop at harvest, as adjusted for grain moisture. Grain moisture is measured in the grain at harvest. The adjusted test weight of grain is determined to be the weight in pounds per bushel or kilogram, adjusted for grain moisture level at harvest.

II. Methods

A. Methods for Increasing *Phytophthora* Resistance

Provided are methods for generating a *Phytophthora* resistant soybean plant or increasing resistance to *Phytophthora* in a soybean plant comprising expressing in a soybean plant a polynucleotide encoding a Rps polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 2, 4, 7 or 10.

"Resistance" and "improved resistance" are used interchangeably herein and refer to any type of increase in resistance or tolerance to, or any type of decrease in susceptibility. A "resistant plant" or "resistant plant variety" need not possess absolute or complete resistance. Instead, a "resistant plant," "resistant plant variety," or a plant or plant variety with "improved tolerance" will have a level of resistance or tolerance which is higher than that of a comparable susceptible plant or variety. A person of ordinary skill in the art can readily identify plants having resistance or improved resistance to *Phytophthora* using methods known in the art.

The plants of the compositions and methods described herein can have resistance or improved resistance to any race or isolate of *Phytophthora sojae* known in the art (e.g., any one of races 1 to 55). In certain embodiments, the plants are resistant or have improved resistance to at least 1, 2, 3, 4, 5, 6, 7, 8, 9, 10, 11, 12, 13, 14, 15, 16, 17, 18, 19, 20 races and/or isolates of *Phytophthora sojae*. In certain embodiments, the plants are resistant or have improved resistance to at least one, at least two, at least three, at least four, at least five, at least six, at least seven, at least eight, at least nine, or at least 10 races and/or isolates of *Phytophthora sojae* selected from the group consisting of Race1, Race 2, Race3, Race4, Race5, Race6, Race7, Race8, Race9 Race13, Race17, Race25, Race31, OH001, OHC2S1, OH003, ISA19A-1, ISA71D-1, MIN12001.01.05, MIN12002.01.05, MIN12002.05.01, MIN12002.05.05, MIN12004.01.01, MIN12004.03.01, MIN12005.07.02. In certain embodiments, the plant has resistance to Race1, Race3, Race4, Race7, Race13, Race17, Race25, ISA19A-1, ISA71D-1, MIN12001.01.05, MIN12004.01.01, MIN12004.03.01, MIN12005.07.02. In certain embodiments, the plant has resistance to Race1, Race 2, Race3, Race4, Race5, Race6, Race7, Race8, Race9, Race13, Race17, Race25, ISA19A-1, ISA71D-1, MIN12001.01.05, MIN12004.01.01, MIN12004.03.01, MIN12005.07.02. In certain embodiments, the plant has resistance to Race1, Race3, Race4, Race7, Race13, Race17, Race25, Race31, OH001, OHC2S1, OH003, MIN12002.01.05, MIN12002.05.01, MIN12002.05.05, ISA19A-1, ISA71D-1, MIN12001.01.05, MIN12004.01.01, MIN12004.03.01, MIN12005.07.02.

In certain embodiments, the method comprises introducing in a regenerable soybean plant cell a targeted genetic modification increasing the expression of a polynucleotide encoding a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 2, 4, 7 or 10 and generating the plant wherein the plant has increased expression of the polynucleotide and increased resistance to *Phytophthora* infection as compared to a control plant not comprising the targeted genetic modification. In certain embodiments, the method comprises introducing in a regenerable soybean plant cell a targeted genetic modification that inserts an exogenous polynucleotide into the plant cell genome, wherein the exogenous polynucleotide encodes a polypeptide comprising an amino acid sequence having at least 95%, 96%, 97%, 98%, or 99% sequence identity to SEQ ID NOs: 2, or 4 and generating the plant from the transformed plant cell, wherein the generated plant expresses the polynucleotide and has increased resistance to *Phytophthora* infection as compared to a control plant not comprising the exogenous polynucleotide.

In certain embodiments, the method comprises introducing in a regenerable soybean plant cell isolated from a soybean plant susceptible to at least one race of *Phytophthora* a polynucleotide encoding a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 2, 4, 7 or 10, and generating the plant wherein the plant expresses the polynucleotide and is resistant to the at least one race of *Phytophthora* as compared to a control plant not expressing the polynucleotide. In certain embodiments, the polynucleotide is introduced in the regenerable soybean plant cell using a targeted genetic modification. In certain embodiments, the polynucleotide is introduced in the regenerable soybean plant cell by a recombinant DNA construct comprising the polynucleotide operably linked to a regulatory element, optionally wherein the regulatory element is a heterologous plant promoter.

In certain embodiments, the method comprises providing a guide RNA, at least one polynucleotide modification template, and at least one Cas endonuclease to a soybean plant cell, wherein the at least one Cas endonuclease introduces a double strand break at a locus in the soybean plant cell, and wherein the polynucleotide modification template introduces and/or inserts a polynucleotide encoding a polypeptide comprising an amino acid sequence that is at least 80% identical to any one of SEQ ID NOs: 2, 4, 7 or 10, obtaining a soybean plant from the soybean plant cell, and generating a progeny plant that comprises the polynucleotide and has increased resistance to *Phytophthora* as compared to a control pant not comprising the targeted genetic modification. In certain embodiments, the locus in the soybean plant cell is an endogenous Rps gene or locus. In certain embodiments, the Cas endonuclease is Cas9.

In certain embodiments of the methods described herein, the regenerable plant cell is derived from a soybean plant that is susceptible to at least on race of *Phytophthora*.

In certain embodiments of the methods described herein, the targeted genetic modification is introduced using a genome modification technique selected from the group consisting of polynucleotide-guided endonuclease, CRISPR-Cas endonucleases, based editing deaminases, a zinc finger nuclease, a transcription activator-like effector nuclease (TALEN), engineered site-specific meganucleases, or Argonaute.

Various methods can be used to introduce a genetic modification at a genomic locus that encodes a Rps polypeptide into the plant, plant part, plant cell, seed, and/or grain. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In certain embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

In one embodiment the DSB-inducing agent is sequence specific endonuclease. The endonuclease can be provided to a cell by any method known in the art, for example, but not limited to, transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

TAL effector nucleases (TALEN) are a class of sequence-specific nucleases that can be used to make double-strand breaks at specific target sequences in the genome of a plant or other organism (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognized a sequence of 9 contiguous nucleotides, with a dimerization requirement of the nuclease, two sets of zinc finger triplets are used to bind an 18-nucleotide recognition sequence.

Genome editing using DSB-inducing agents, such as Cas9-gRNA complexes, has been described, for example in U.S. Patent Application US 2015-0082478 A1, WO2015/026886 A1, WO2016007347, and WO201625131 all of which are incorporated by reference herein.

In certain embodiments the genetic modification is introduced without introducing a double strand break using base editing technology, see e.g., Gaudelli et al., (2017) Programmable base editing of A*T to G*C in genomic DNA without DNA cleavage. Nature 551(7681):464-471; Komor et al., (2016) Programmable editing of a target base in genomic DNA without double-stranded DNA cleavage, Nature 533 (7603):420-4.

In certain embodiments, base editing comprises (i) a catalytically impaired CRISPR-Cas9 mutant that is mutated such that one of their nuclease domains cannot make DSBs; (ii) a single-strand-specific cytidine/adenine deaminase that converts C to U or A to G within an appropriate nucleotide window in the single-stranded DNA bubble created by Cas9; (iii) a uracil glycosylase inhibitor (UGI) that impedes uracil excision and downstream processes that decrease base editing efficiency and product purity; or (iv) nickase activity to cleave the non-edited DNA strand, followed by cellular DNA repair processes to replace the G-containing DNA strand.

In certain embodiments, the targeted genetic modification is selected from the group consisting of an insertion, deletion, single nucleotide polymorphism (SNP), and a polynucleotide modification. In certain embodiments, the targeted genetic modification is present in (a) the coding region; (b) a non-coding region; (c) a regulatory sequence; (d) an untranslated region; or (e) any combination of (a)-(d) of the genomic locus that encodes the RPS polypeptide.

In certain embodiments the DNA modification increasing the level and or activity of the RPS polypeptide is an insertion of one or more nucleotides, preferably contiguous, in the genomic locus. For example, the insertion of an expression modulating element (EME), such as an EME described in PCT/US2018/025446 (WO2018183878), in operable linkage with the RPS gene. In certain embodiments, the targeted DNA modification may be the replacement of the endogenous RPS promoter with another promoter known in the art to have higher expression. In certain embodiments, the targeted DNA modification may be the insertion of a promoter known in the art to have higher expression into the 5'UTR so that expression of the endogenous RPS polypeptide is controlled by the inserted promoter. In certain embodiments, the DNA modification is a modification to optimize Kozak context to increase expression. In certain embodiments, the DNA modification is a polynucleotide modification or SNP at a site that regulates the stability of the expressed protein.

In certain embodiments, the method comprises expressing in a regenerable soybean plant cell any of the recombinant DNA constructs described herein and generating the plant wherein the plant has increased expression of the polynucleotide and increased resistance to *Phytophthora* infection as compared to a control plant not comprising the recombinant DNA construct.

Various methods can be used to introduce the RPS sequences (e.g., modified RPS sequence or recombinant DNA comprising the modified RPS sequence) into a plant, plant part, plant cell, seed, and/or grain. "Introducing" is intended to mean presenting to the plant, plant cell, seed, and/or grain the inventive polynucleotide or resulting polypeptide in such a manner that the sequence gains access to the interior of a cell of the plant. The methods of the disclosure do not depend on a particular method for introducing a sequence into a plant, plant cell, seed, and/or grain, only that the polynucleotide or polypeptide gains access to the interior of at least one cell of the plant.

"Stable transformation" is intended to mean that the polynucleotide introduced into a plant integrates into the genome of the plant of interest and is capable of being inherited by the progeny thereof. "Transient transformation" is intended to mean that a polynucleotide is introduced into the plant of interest and does not integrate into the genome of the plant or organism or a polypeptide is introduced into a plant or organism.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (U.S. Pat. Nos. 5,563,055 and 5,981,840), *Ochrobacterium*-mediated transformation (U.S. Patent Application Publication 2018/0216123 and WO20/092494) direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the RPS sequences can be provided to a plant using a variety of transient transformation methods. Such transient transformation methods include, but are not limited to, the introduction of the RPS protein directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al.

(1994) *Proc. Natl. Acad. Sci.* 91: 2176-2180 and Hush et al. (1994) *The Journal of Cell Science* 107:775-784, all of which are herein incorporated by reference.

In other embodiments, the inventive polynucleotides disclosed herein may be introduced into plants by contacting plants with a virus or viral nucleic acids. Generally, such methods involve incorporating a nucleotide construct of the disclosure within a DNA or RNA molecule. It is recognized that the inventive polynucleotide sequence may be initially synthesized as part of a viral polyprotein, which later may be processed by proteolysis in vivo or in vitro to produce the desired recombinant protein. Further, it is recognized that promoters disclosed herein also encompass promoters utilized for transcription by viral RNA polymerases.

Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide disclosed herein can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided, and the transfer cassette is integrated at the target site. The polynucleotide of interest is thereby integrated at a specific chromosomal position in the plant genome. Other methods to target polynucleotides are set forth in WO 2009/114321 (herein incorporated by reference), which describes "custom" meganucleases produced to modify plant genomes, in particular the genome of maize. See, also, Gao et al. (2010) *Plant Journal* 1:176-187.

One of skill will recognize that after the expression cassette containing the inventive polynucleotide is stably incorporated in transgenic plants and confirmed to be operable, it can be introduced into other plants by sexual crossing. Any of a number of standard breeding techniques can be used, depending upon the species to be crossed.

Parts obtained from the regenerated plants described herein, such as flowers, seeds, leaves, branches, fruit, and the like are included, provided that these parts comprise cells comprising the inventive polynucleotide. Progeny and variants, and mutants of the regenerated plants are also included, provided that these parts comprise the introduced nucleic acid sequences.

In one embodiment, a homozygous transgenic plant can be obtained by sexually mating (selfing) a heterozygous transgenic plant that contains a single added heterologous nucleic acid, germinating some of the seed produced and analyzing the resulting plants produced for altered cell division relative to a control plant (i.e., native, non-transgenic). Back-crossing to a parental plant and out-crossing with a non-transgenic plant are also contemplated.

B. Breeding Method for Increasing *Phytophthora* Resistance

Further provided are methods of producing plants having increased *Phytophthora* resistance comprising crossing a plant comprising a targeted genetic modification increasing expression of a polynucleotide encoding a polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 2, 4, 7 or 10 as compared to a control plant not comprising the targeted genetic modification with a second plant line and harvesting the seed produced thereby. In certain embodiments, the seed produced thereby comprises the polynucleotide. In certain embodiments, the second plant is susceptible to *Phytophthora* and the harvested seed produces a plant that is resistant and/or has increased resistance to *Phytophthora*.

In certain embodiments, the method further comprises growing the seed to produce a second-generation progeny plant that comprises the polypeptide and backcrossing the second-generation progeny plant to the second plant to produce a backcross progeny plant that comprises the polypeptide and produces backcrossed seed with increased *Phytophthora* resistance.

Also provided are methods of producing plants having increased *Phytophthora* resistance comprising crossing a plant comprising increased expression of a polynucleotide encoding a polypeptide comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to any one of SEQ ID NOs: 2, 4, 7 or 10 as compared to a control plant not comprising the polynucleotide with a second plant line and harvesting the seed produced thereby. In certain embodiments, the plant comprises a recombinant DNA construct described herein. In certain embodiments, the seed produced thereby comprises the polynucleotide. In certain embodiments, the second plant is susceptible to *Phytophthora* and the harvested seed produces a plant that is resistant and/or has increased resistance to *Phytophthora*.

In certain embodiments, the method further comprises growing the seed to produce a second-generation progeny plant that comprises the polypeptide and backcrossing the second-generation progeny plant to the second plant to produce a backcross progeny plant that comprises the polypeptide and produces backcrossed seed with increased *Phytophthora* resistance.

C. Methods to Detect a *Phytophthora* Resistant Plant

Also provided herein are methods for detecting a *Phytophthora* resistant plant comprising identifying plants comprising a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2, 4, 7 or 10. In certain embodiments, the method comprises detecting the nucleic acid sequence using primers and probes that selectively detect a polynucleotide comprising a nucleic acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 2, 4, 7 or 10.

Also provided herein are methods for detecting a *Phytophthora* resistant plant comprising detecting a molecular marker linked to or associated with Rps11, Rps2b, Rps15, or Rps14.

In certain embodiments, the method comprises detecting a marker linked to or associated with Rps11. In certain embodiments, the method comprises detecting in germplasm of a soybean plant at least one allele of a marker locus within a chromosomal interval comprising and flanked by SSR-07-286 (SEQ ID NOs: 66 and 67) and SSR-07-320 (SEQ ID NOs: 84 and 85). In certain embodiments, the method comprises detecting in germplasm of a soybean plant at least one allele of a marker locus within a chromosomal interval comprising and flanked by maker_176kb (SEQ ID NOs: 76 and 77) and InDel_327kb (SEQ ID NOs: 78 and 79). In certain embodiments, the method comprises detecting a marker selected from the group consisting of SSR-07-286, SSR-07-295 (SEQ ID NOs: 68 and 69), InDel-626 (SEQ ID NOs: 70 and 71), InDel-SUTR-43 (SEQ ID NOs: 72 and 73), SSR-07-300 (SEQ ID NOs: 74 and 75), 176kb (SEQ ID NOs: 76 and 77), InDel-327kb (SEQ ID NOs: 78 and 79), InDel-5.922 (SEQ ID NOs: 80 and 81), InDel-6.036 (SEQ ID NOs: 82 and 83), and SSR-07-320 (SEQ ID NOs: 84 and 85).

In certain embodiments, the method comprises detecting a marker linked to or associated with Rps2b. In certain embodiments, the method comprises detecting in germplasm of a soybean plant at least one allele of a marker locus within a chromosomal interval comprising and flanked by Satt431 (SEQ ID NOs: 20 and 21) and BARCSOY_16_1322 (SEQ ID NOs: 34 and 35). In certain embodiments, the method comprises detecting in germplasm of a soybean plant at least one allele of a marker locus within a chromosomal interval comprising and flanked by BARCSOY_16_1277 (SEQ ID NOs: 22 and 23) and BARCSOY_16_1322 (SEQ ID NOs: 34 and 35). In certain embodiments, the method comprises detecting in germplasm of a soybean plant at least one allele of a marker locus within a chromosomal interval comprising and flanked by BARCSOY_16_1288 (SEQ ID NOs: 26 and 27) and BARCSOY_16_1312 (SEQ ID NOs: 32 and 33). In certain embodiments, the method comprises detecting a marker selected from the group consisting of Satt431, BARCSOY_16_1277, BARCSOY_16_1281 (SEQ ID NOs: 24 and 25), BARCSOY_16_1288, BARCSOY_16_1294 (SEQ ID NOs: 28 and 29), BARCSOY_16_1297 (SEQ ID NOs: 30 and 31), BARCSOY_16_1312, BARCSOY_16_1322, a G at Gm16_36635129 (SEQ ID NO: 37), an A at Gm16_36641187 (SEQ ID NO: 39), a C at Gm16_36687038 (SEQ ID NO: 41), an A at Gm16_36742320 (SEQ ID NO: 43), a C at Gm16_36745870 (SEQ ID NO: 45), a T at Gm16_36789567 (SEQ ID NO: 47), a G at Gm16_36805209 (SEQ ID NO: 49), an A at Gm16_36818299 (SEQ ID NO: 51), a T at Gm16_36825046 (SEQ ID NO: 53), a G at Gm16_36840817 (SEQ ID NO: 55), a T at Gm16_36844181 (SEQ ID NO: 57), an A at Gm16_36849203 (SEQ ID NO: 59), a T at Gm16_36854790 (SEQ ID NO: 61), a C at Gm16_36870179 (SEQ ID NO: 63), and a G at Gm16_36889339 (SEQ ID NO: 65).

In certain embodiments, the method comprises detecting a marker linked to or associated with Rps15. In certain embodiments, the method comprises detecting in germplasm of a soybean plant at least one allele of a marker locus within a chromosomal interval comprising and flanked by InDel3155 and InDel3701. In certain embodiments, the method comprises detecting in germplasm of a soybean plant at least one allele of a marker locus within a chromosomal interval comprising and flanked by InDel3437 and InDel3701. In certain embodiments, the method comprises detecting in germplasm of a soybean plant at least one allele of a marker locus within a chromosomal interval comprising and flanked by Satt431 and InDel3668. In certain embodiments, the method comprises detecting a marker selected from the group consisting of InDel3155, InDel3255, InDel3304, InDel3437, InDel3575, InDel3586, Satt431, InDel3668, InDel3678, InDel3701, a T at Gm_30813568, a C at Gm16_31787658, a T at Gm16_31837545, an A at Gm16_31899513, a C at Gm16_32017661, a C at Gm16_32200441, an A at Gm16_32340079, a C at Gm16_32665742, a G at Gm16_32876100, a C at Gm16_33210540, a C at Gm16_33360539, a G at Gm16_33457667, a G at Gm16_34645180, a G at Gm16_35148803, a T at Gm16_35218386, a T at Gm16_35643452, a T at Gm16_35700223, a G at Gm16_35738081, an A at Gm16_36013043, a C at Gm16_36217195, a C at Gm16_36732450, an A at Gm16_36983033, a G at Gm16_37078478, and a G at Gm16_37209075. In certain embodiments, the marker is detected by a primer comprising a nucleotide sequence of any one of SEQ ID NOs: 20-21 and 86-103. In certain embodiments, the marker is detected by a primer pair comprising a nucleotide sequences of SEQ ID NOs: 20 and 21, SEQ ID NOs: 86 and 87, SEQ ID NOs: 88 and 89, SEQ ID NOs: 90 and 91, SEQ ID NOs: 92 and 93, SEQ ID NOs: 94 and 95, SEQ ID NOs: 96 and 97, SEQ ID NOs: 98 and 99, SEQ ID NOs: 100 and 101, and SEQ ID NOs: 102 and 103.

In certain embodiments, the method comprises detecting a marker linked to or associated with Rps14. In certain embodiments, the method comprises detecting in germplasm of a soybean plant at least one allele of a marker locus within a chromosomal interval comprising and flanked by Satt631 and BARCSOY_03_0266. In certain embodiments, the method comprises detecting in germplasm of a soybean plant at least one allele of a marker locus within a chromosomal interval comprising and flanked by BARCSOY_03_0226 and BARCSOY_03_0266. In certain embodiments, the method comprises detecting a marker selected from the group consisting of Satt631, BARCSOY_03_0209, BARCSOY_03_0219, BARCSOY_03_0226, BARCSOYSSR_03_229, BARCSOY_03_0266, InDel3971, InDel4033, InDel4263, InDel4330, a T at Gm03_829023, an A at Gm03_1671384, a G at Gm03_1718435, an A at Gm03_3087237, a G at Gm03_3907697, a C at Gm03_4487138, an A at Gm03_4509101, a Cat Gm03_4665923, a Cat Gm03_4782127, an A at Gm03_5165511, and a C at Gm03_5217414. In certain embodiments, the marker is detected by a primer comprising a nucleotide sequence of any one of SEQ ID NOs: 104-123. In certain embodiments, the marker is detected by a primer pair comprising a nucleotide sequences of SEQ ID NOs: 104 and 105, SEQ ID NOs: 106 and 107, SEQ ID NOs: 108 and 109, SEQ ID NOs: 110 and 111, SEQ ID NOs: 112 and 113, SEQ ID NOs: 114 and 115, SEQ ID NOs: 116 and 117, SEQ ID NOs: 118 and 119, SEQ ID NOs: 120 and 121, and SEQ ID NOs: 122 and 123.

In certain embodiments, the method further comprises crossing the *Phytophthora* resistant plant detected by the methods described herein with a second plant to produce progeny seed. In certain embodiments, the second plant is susceptible to *Phytophthora*. In certain embodiments, the second plant lacks the Rps11, Rps2b, Rps15, or Rps14 gene.

In certain embodiments, the progeny seed comprises the nucleotide sequence detected using the primers and probes. In certain embodiments, the progeny seed comprises the molecular marker linked to or associated with Rps11, Rps2b, Rps15, or Rps14. In certain embodiments, the progeny seed comprises the at least one allele of a marker locus associated with Rps2b within a chromosomal interval comprising and flanked by BARCSOY_16_1288 and BARCSOY_16_1312. In certain embodiments, the progeny seed and plant produced thereby comprises the at least one allele of a marker locus associated with Rps15 within a chromosomal interval comprising and flanked by Satt431 and InDel3668. In certain embodiments, the progeny seed comprises the at least one allele of a marker locus associated with Rps14 within a chromosomal interval comprising and flanked by BARCSOY_03_0226 and BARCSOY_03_0266. In certain embodiments, the progeny seed and plant produced thereby comprises the Rps11, Rps2b, Rps15, or Rps14 gene.

Any suitable detection method known in the art can be used to detect the polynucleotide. In some examples, the presence of the polynucleotide is directly detected in unamplified genomic DNA by performing a Southern blot on a sample of genomic DNA using probes to the marker loci. In other examples, amplification-based techniques are employed. PCR, RT-PCR, and LCR are in particularly broad use as amplification and amplification-detection methods for amplifying nucleic acids of interest, thus facilitating detection of the polynucleotide. Procedures for performing Southern blotting, amplification (PCR, LCR, or the like), and many other nucleic acid detection methods are well established and are taught, e.g., in Sambrook et al., *Molecular Cloning—A Laboratory Manual* (3d ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis et al. eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

"Primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are oligonucleotides from 10 to 30 nucleic acids in length, but longer or shorter sequences can be employed. Primers may be provided in double-stranded form, though the single-stranded form is preferred. A primer can further contain a detectable label, for example a 5' end label.

"Probe" refers to an oligonucleotide (synthetic or occurring naturally) that is complementary (though not necessarily fully complementary) to a polynucleotide of interest and forms a duplexed structure by hybridization with at least one strand of the polynucleotide of interest. Typically, probes are oligonucleotides from 10 to 50 nucleic acids in length, but longer or shorter sequences can be employed. A probe can further contain a detectable label. The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin, or haptens), and the like. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

Chromosomal interval" designates a contiguous linear span of genomic DNA that resides in planta on a single chromosome. The genetic elements or genes located on a single chromosomal interval are physically linked. The size of a chromosomal interval is not particularly limited. In certain embodiments, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

The term "introgression" or "introgressing" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a quantitative trait loci (QTL), a transgene, or the like. In any case, offspring comprising the desired allele can be repeatedly backcrossed to a line having a desired genetic background and selected for the desired allele, to result in the allele becoming fixed in a selected genetic background. For example, the chromosome 3, 7, or 16 locus described herein may be introgressed into a recurrent parent that is susceptible to *Phytophthora*. The recurrent parent line with the introgressed gene or locus then has increased resistance to *Phytophthora*.

As used herein, the term "linkage" or "linked" is used to describe the degree with which one marker locus is associated with another marker locus or some other locus (for example, a *Phytophthora* locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units for cM). In certain embodiments, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10 (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

"Locus" and "marker locus" are used interchangeably herein and mean a position on a chromosome where a gene and/or marker is located.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of soybean molecular markers are known in the art, and are published or available from various sources, such as the SoyBase internet resource.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus.

A "marker locus" is a specific chromosome location in the genome of a species when a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in certain embodiments, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a via a plant without the insertion. Thus, the marker need only indicate whether the indel region is present or absent. Any suitable marker detection technology may be used to identify such a hybridization marker, e.g., SNP technology is used in the examples provided herein.

The following are examples of specific embodiments of some aspects of the invention. The examples are offered for illustrative purposes only and are not intended to limit the scope of the invention in any way.

In accordance with embodiment 1, a soybean plant or soybean seed is provided comprising a targeted genetic modification increasing expression of a polynucleotide encoding a polypeptide comprising an amino acid sequence having at least 80% sequence identity to any one of SEQ ID NOs: 2 or 4 as compared to a control plant not comprising the targeted genetic modification.

In accordance with embodiment 2 the soybean plant or soybean seed of embodiment 1 is provided, wherein the soybean plant or a plant grown from the soybean seed comprising the targeted genetic modification has improved resistance to *Phytophthora* infection as compared to the control plant.

In accordance with embodiment 3 the soybean plant or soybean seed of embodiment 1 or 2 is provided, wherein the soybean plant or a plant grown from the soybean seed comprising the targeted genetic modification has improved resistance at least one race of *Phytophthora* selected from the group consisting of Race1, Race 2, Race3, Race4, Race5, Race6, Race7, Race8, Race9 Race13, Race17, Race25, Race31 as compared to the control plant.

In accordance with embodiment 4 the soybean plant or soybean seed of any one of embodiments 1-3 is provided, wherein the targeted genetic modification introduces a polynucleotide sequence having at least 80% sequence identity to any one of SEQ ID NOs: 1 or 3.

In accordance with embodiment 5 a plant produced by the soybean seed of any one of embodiments 1-4 is provided.

In accordance with embodiment 6 a method of plant breeding is provided comprising crossing the soybean plant of any one of embodiments 1-5 with a second soybean plant to produce a progeny seed.

In accordance with embodiment 7 the method of any one of embodiments 1-6 is provided, wherein the progeny seed comprises the targeted genetic modification and a plant produced from the seed has increased resistance to at least one race of *Phytophthora*.

In accordance with embodiment 8 the method of any one of embodiments 1-7 is provided, wherein the second soybean plant is susceptible to the at least one race of *Phytophthora*.

In accordance with embodiment 9 the method of any one of embodiments 1-9 is provided, wherein the the plant, seed or plant produced from the seed has increased resistance to at least one race of *Phytophthora* selected from Race1, Race 2, Race3, Race4, Race5, Race6, Race7, Race8, Race9 Race13, Race17, Race25, or Race31.

In accordance with embodiment 10 a method for generating a *Phytophthora* resistant soybean plant is provided, the method comprising:
  (a) introducing in a regenerable soybean plant cell a polynucleotide encoding a polypeptide comprising an amino acid sequence having at least 80% sequence identity to any one of SEQ ID NOs: 2 or 4, and
  (b) generating the plant wherein the plant expresses the polynucleotide and has increased resistance to *Phytophthora* as compared to a control plant not expressing the polynucleotide.

In accordance with embodiment 11 the method of embodiment 10 is provided, wherein the regenerable plant cell is isolated from a soybean plant susceptible to at least one race of *Phytophthora* and the plant generated has increased resistance to the at least one race of *Phytophthora*.

In accordance with embodiment 12 the method of embodiment 10 or 11 is provided, wherein the at least one race of *Phytophthora* is at least one of Race1, Race 2, Race3, Race4, Race5, Race6, Race7, Race8, Race9 Race13, Race17, Race25, Race31.

In accordance with embodiment 13 the method of any one of embodiments 10-12 is provided, wherein the polynucleotide is introduced in the regenerable soybean plant cell using a targeted genetic modification.

In accordance with embodiment 14 the method of embodiment 13 is provided, wherein the targeted genetic modification is introduced using a genome modification technique selected from the group consisting of polynucleotide-guided endonuclease, CRISPR-Cas endonucleases, based editing deaminases, a zinc finger nuclease, a transcription activator-like effector nuclease (TALEN), engineered site-specific meganucleases, or Argonaute.

In accordance with embodiment 15 the method of any one of embodiments 10-14 is provided, wherein the polynucleotide is introduced in the regenerable soybean plant cell by a recombinant DNA construct comprising the polynucleotide operably linked to at least one regulatory element.

In accordance with embodiment 16 the method of any one of embodiments 10-15 is provided, wherein the at least one regulatory element is a promoter.

In accordance with embodiment 17 the method of embodiment 17 is provided, wherein the promoter is a heterologous promoter.

In accordance with embodiment 18 a method for increasing resistance to *Phytophthora* infection in a soybean plant, the method comprising:
  (a) introducing in a regenerable soybean plant cell a targeted genetic modification increasing the expression of a polynucleotide encoding a polypeptide comprising an amino acid sequence having at least 80% sequence identity to any one of SEQ ID NOs: 2 or 4, and
  (b) generating the plant wherein the plant has increased expression of the polynucleotide and increased resistance to *Phytophthora* infection as compared to a control plant not comprising the targeted genetic modification.

In accordance with embodiment 19 the method of embodiment 18 is provided, wherein the targeted genetic modification is introduced using a genome modification technique selected from the group consisting of polynucleotide-guided endonuclease, CRISPR-Cas endonucleases, based editing deaminases, a zinc finger nuclease, a transcription activator-like effector nuclease (TALEN), engineered site-specific meganucleases, or Argonaute.

In accordance with embodiment 20 the method of embodiment 18 or 19 is provided, wherein the method comprises:
  (a) providing a guide RNA, at least one polynucleotide modification template, and at least one Cas endonuclease to a soybean plant cell, wherein the at least one Cas endonuclease introduces a double strand break at a locus in the soybean plant cell, and wherein the polynucleotide modification template inserts a polynucleotide encoding a polypeptide comprising an amino acid sequence that is at least 80% identical to any one of SEQ ID NOs: 2 or 4;
  (b) obtaining a soybean plant from the soybean plant cell; and
  (c) generating a progeny plant that comprises the polynucleotide and has increased resistance to *Phytophthora* as compared to a control pant not comprising the targeted genetic modification.

In accordance with embodiment 21 the method of any one of embodiments 18-20 is provided, wherein the locus is an endogenous Rps locus.

In accordance with embodiment 22 the method of any one of embodiments 18-21, wherein the Cas endonuclease is Cas9.

In accordance with embodiment 23 the method of any one of embodiments 18-22 is provided, wherein the plant cell is isolated from a soybean plant susceptible to at least one race of *Phytophthora* and the progeny plant has increased resistance to the at least one race of *Phytophthora*.

In accordance with embodiment 24 the method of embodiment 23 is provided, wherein the at least one race of *Phytophthora* is at least one of Race1, Race 2, Race3, Race4, Race5, Race6, Race7, Race8, Race9 Race13, Race17, Race25, Race31.

In accordance with embodiment 25 a method for producing a soybean plant with increased resistance to *Phytophthora*, the method comprising:
  (a) expressing in a regenerable plant cell a polynucleotide encoding a polypeptide comprising an amino acid sequence having at least 80% sequence identity to any one of SEQ ID NOs: 2 or 4, and
  (b) generating a plant wherein the plant expresses the polynucleotide and has increased resistance to *Phytophthora* infection as compared to a control plant.

In accordance with embodiment 26 the method of embodiment 25 is provided, wherein the method comprises:
  (a) providing a guide RNA, at least one polynucleotide modification template, and at least one Cas endonuclease to a soybean plant cell, wherein the at least one Cas endonuclease introduces a double strand break in the genome of the soybean plant cell, and wherein the polynucleotide modification template inserts a polynucleotide encoding a polypeptide comprising an amino acid sequence that is at least 80% identical to any one of SEQ ID NOs: 2 or 4;
  (b) obtaining a soybean plant from the soybean plant cell; and
  (c) generating a progeny plant that comprises the polynucleotide and has increased resistance to *Phytophthora* as compared to a control pant not comprising the targeted genetic modification.

In accordance with embodiment 27 the method of embodiment 18-26 is provided, wherein the double strand break is introduced at an endogenous Rps gene in the soybean plant cell.

In accordance with embodiment 28 the method of any one of embodiments 18-27 is provided, wherein the Cas endonuclease is Cas9.

In accordance with embodiment 29 the method of any one of embodiments 18-28 is provided, wherein the plant cell is isolated from a soybean plant susceptible to at least one race of *Phytophthora* and the progeny plant has increased resistance to the at least one race of *Phytophthora*.

In accordance with embodiment 30 the method of embodiment 29 is provided, wherein the at least one race of *Phytophthora* is at least one of Race1, Race 2, Race3, Race4, Race5, Race6, Race7, Race8, Race9 Race13, Race17, Race25, Race31.

In accordance with embodiment 31 a soybean plant or soybean seed comprising a recombinant DNA construct comprising a polynucleotide encoding a polypeptide comprising an amino acid sequence that is at least 80% identical to any one of SEQ ID NOs: 2 or 4, wherein the soybean seed or soybean plant has increased expression of the polynucleotide as compared to a control plant not comprising the polynucleotide.

In accordance with embodiment 32 the soybean plant or soybean seed of embodiment 31 is provided, wherein the polynucleotide is operably linked to the endogenous promoter.

In accordance with embodiment 33 the soybean plant or soybean seed of embodiment 31 or 32 is provided, wherein the soybean plant or a plant grown from the soybean seed comprising the recombinant DNA construct has improved *Phytophthora* resistance as compared to the control plant.

In accordance with embodiment 34 a plant produced by the soybean seed of any one of embodiments 31-33 is provided.

In accordance with embodiment 35 a method of plant breeding is provided comprising crossing the soybean plant of any one of embodiments 31-34 with a second soybean plant to produce a progeny seed.

In accordance with embodiment 36 the method of embodiment 35 is provided, wherein the second soybean plant is susceptible to at least one race of *Phytophthora* and a plant produced from the progeny seed is resistant or has increased resistance to the at least one race of *Phytophthora*.

In accordance with embodiment 37 a method for increasing resistance to *Phytophthora* infection in a soybean plant, the method comprising:
  (a) expressing in a regenerable soybean plant cell a recombinant DNA construct comprising a polynucleotide encoding a polypeptide comprising an amino acid sequence having at least 80% sequence identity to any one of SEQ ID NOs: 2 or 4, and
  (b) generating the plant wherein the plant has increased expression of the polynucleotide and increased resistance to *Phytophthora* infection as compared to a control plant not comprising the recombinant DNA construct.

In accordance with embodiment 38 the method of embodiment 37 is provided, wherein the polynucleotide is operably linked to the endogenous promoter.

In accordance with embodiment 39 a method for identifying a soybean plant that displays increased resistance to *Phytophthora* is provided, the method comprising detecting in a soybean plant or seed thereof a polynucleotide sequence encoding a polypeptide comprising an amino acid sequence that is at least 80% identical to any one of SEQ ID NOs: 2 or 4.

In accordance with embodiment 40 the method of embodiment 39 is provided, wherein the polynucleotide sequence is detected using a primer comprising a nucleotide sequence of any one of SEQ ID NOs: 12-19.

In accordance with embodiment 41 The method of embodiment 39 or 40, further comprising:
  a. obtaining a first soybean plant comprising the polynucleotide;
  b. crossing the first soybean plant to a second soybean plant;
  c. evaluating the progeny for the at least one allele; and
  d. selecting progeny plants that possess the at least one allele thereby selecting plants with increased *Phytophthora* resistance.

In accordance with embodiment 42 a method for identifying a soybean plant that displays increased resistance to *Phytophthora*, the method comprising detecting in a soybean plant or seed thereof at least one allele of a marker locus associated with Rps11, Rps2b, Rps15, or Rps14.

In accordance with embodiment 43 the method of embodiment 42 is provided, wherein:
  e. the marker locus is located within a chromosomal interval comprising and flanked by SSR-07-286 and SSR-07-320;
  f. the marker locus is located within a chromosomal interval comprising and flanked by InDel3437 and InDel3701;
  g. the marker locus is located within a chromosomal interval comprising and flanked by Satt431 and BARCSOY_16_1322; and
  h. the marker locus is located within a chromosomal interval comprising and flanked by Satt631 and BARCSOY_03_0266.

In accordance with embodiment 44 the method of embodiment 42 or 43 is provided, further comprising:
  i. obtaining a first soybean plant comprising the at least one allele of the marker locus;
  j. crossing the first soybean plant to a second soybean plant;
  k. evaluating the progeny for the at least one allele; and
  l. selecting progeny plants that possess the at least one allele thereby selecting plants with increased *Phytophthora* resistance.

Example 1

This example demonstrates the determination of the spectrum of resistance of Rps11 to *Phytophthora sojae*.

To explore the resistance spectrum of Rps11, a sub population derived from the Rps11 donor line (PI 594527) and Williams, including 14 lines with Rps11 and 14 lines without Rps11, were inoculated with 16 isolates of *P. sojae*.

The mapping populations were generated from an initial cross between PI 594527 and Williams. In 2015, 2640 F3 plants derived from heterozygous F2 individuals were screened for the identification of recombinants. In 2016 and 2017, two additional larger populations of 7680 and 6730 F4 plants, respectively, derived from heterozygous F3 individuals, were screened for additional recombinants.

About 30 seedlings from each recombinant were inoculated with various isolates of *Phytophthora sojae* using a protocol previously described (Dorrance et al. 2008; Lin et al. 2013). Recombinants, in which less than 25% of the progenies survived after inoculation, were classified as susceptible; recombinants, with more than 25% progeny survival, were classified as segregation. The evaluation was repeated twice for each recombinant. For the resistance spectrum test, lines in which less than 25% of the progenies survived after inoculation were classified as susceptible, lines in which 25% to 75% of the progenies survived after inoculation were classified as partially resistant, and lines in which more than 75% of the progenies survived after inoculation were classified as completely resistant.

As shown in Table 2 all the lines with Rps11 were resistant to all 15 isolates, while all lines without Rps11 were susceptible to 14 isolates except Race 31, suggesting that Rps11 was resistant to all 15 isolates and another gene in the donor line was specifically resistant to Race 31 (Table 2).

These results demonstrated that Rps11 has a broad resistance spectrum to *Phytophthora sojae*.

Example 2

This example demonstrates the identification of the Rps11 sequence.

Whole genome sequencing and assembly was performed to obtain an assembly of the Rps11 region in the donor line.

TABLE 2

Resistance Spectrum of Rps11

| Sample | Rps11[a] genotype | Race4[b] | Race7 | Race25 | Race3 | Race31 | OH001 | OHC2S1 |
|---|---|---|---|---|---|---|---|---|
| 1 | rps11 | S | S | S | S | S | S | S |
| 2 | rps11 | S | S | S | S | S | S | S |
| 3 | rps11 | S | S | S | S | H | S | S |
| 4 | rps11 | S | S | S | S | R | S | S |
| 5 | rps11 | S | S | S | S | H | S | S |
| 6 | rps11 | S | S | S | S | H | S | S |
| 7 | rps11 | S | S | S | S | S | S | S |
| 8 | rps11 | S | S | S | S | R | S | S |
| 9 | rps11 | S | S | S | S | H | S | S |
| 10 | rps11 | S | S | S | S | H | S | S |
| 11 | rps11 | S | S | S | S | R | S | S |
| 12 | rps11 | S | S | S | S | H | S | S |
| 13 | rps11 | S | S | S | S | S | S | S |
| 14 | rps11 | S | S | S | S | H | S | S |
| 15 | RPS11 | R | R | R | R | R | R | R |
| 16 | RPS11 | R | R | R | R | R | R | R |
| 17 | RPS11 | R | R | R | R | R | R | R |
| 18 | RPS11 | R | R | R | R | R | R | R |
| 19 | RPS11 | R | R | R | R | R | R | R |
| 20 | RPS11 | R | R | R | R | R | R | R |
| 21 | RPS11 | R | R | R | R | R | R | R |
| 22 | RPS11 | R | R | R | R | R | R | R |
| 23 | RPS11 | R | R | R | R | R | R | R |
| 24 | RPS11 | R | R | R | R | R | R | R |
| 25 | RPS11 | R | R | R | R | R | R | R |
| 26 | RPS11 | R | R | R | R | R | R | R |
| 27 | RPS11 | R | R | R | R | R | R | R |
| 28 | RPS11 | R | R | R | R | R | R | R |

| Sample | OH003 | MIN1 2004.03.01 | MIN1 2004.01.01 | MIN1 2002.01.05 | MIN1 2002.05.01 | MIN1 2005.07.02 | MIN1 2002.05.05 |
|---|---|---|---|---|---|---|---|
| 1 | S | S | S | S | S | S | S |
| 2 | S | S | S | S | S | S | S |
| 3 | S | S | S | S | S | S | S |
| 4 | S | S | S | S | S | S | S |
| 5 | S | S | S | S | S | S | S |
| 6 | S | S | S | S | S | S | S |
| 7 | S | S | S | S | S | S | S |
| 8 | S | S | S | S | S | S | S |
| 9 | S | S | S | S | S | S | S |
| 10 | S | S | S | S | S | S | S |
| 11 | S | S | S | S | S | S | S |
| 12 | S | S | S | S | S | S | S |
| 13 | S | S | S | S | S | S | S |
| 14 | S | S | S | S | S | S | S |
| 15 | R | R | R | R | R | R | R |
| 16 | R | R | R | R | R | R | R |
| 17 | R | R | R | R | R | R | R |
| 18 | R | R | R | R | R | R | R |
| 19 | R | R | R | R | R | R | R |
| 20 | R | R | R | R | R | R | R |
| 21 | R | R | R | R | R | R | R |
| 22 | R | R | R | R | R | R | R |
| 23 | R | R | R | R | R | R | R |
| 24 | R | R | R | R | R | R | R |
| 25 | R | R | R | R | R | R | R |
| 26 | R | R | R | R | R | R | R |
| 27 | R | R | R | R | R | R | R |
| 28 | R | R | R | R | R | R | R |

[a]RPS11 represents homozygous Rps11 genotype, rps11 means homozygous Williams genotype (No Rps11)
[b]S represents susceptible, R represents resistant, H represents heterozygous (segregation)

The genome was built with 34 kb PacBio reads which assembled into 424 contigs with a contig N50 of 13.8 Mb. These contigs were polished with PacBio and Chromium 10× data. The contigs were scaffolded with 45 BioNano maps with a map N50 of 26.7 Mb into 43 hybrid scaffolds with a scaffold N50 of 26.4 Mb, essentially 1-2 scaffolds per chromosome. Gene annotation identified 510 NBS-LRR genes across the entire genome, and twelve NBS-LRR genes were annotated at the Rps11 region, designated as R1 to R12. However, only five (R1, R4, R6, R9 and R12) out of the twelve NBS-LRR genes at Rps11 region were expressed based on RNA-seq analysis (FIG. 1).

In order to fine map the gene underlying Rps11 locus, 17,050 progenies derived from heterozygous $F_2$ or $F_3$ individuals were screened using flanking markers. In total, 43 recombinants were identified, and seedlings derived from these recombinants were inoculated with Race 1 isolate. The combination of additional markers and phenotypic data mapped Rps11 to a 151 kb genome interval, defined by maker_176kb and InDel_327kb, harboring 4 intact NBS-LRR genes (R5, R6, R7 and R8), but only R6 was expressed during inoculation, indicating R6 was the best candidate gene responsible for the resistance of Rps11.

Expression of the NBS-LRR genes was further examined in 9 key recombinants that have different combinations of NBS-LRR genes. These studies determined that recombinants with R1 alone, a combination of R1 and R4, or a combination of R9 and R12 were susceptible, whereas the recombinants carrying R6 were resistant (FIG. 2).

These data indicate that R6, which encodes an NBS-LRR protein composed of 2,463 amino acids, is the gene underlying Rps11 locus.

Example 3

This example demonstrates expression of the Rps11 in plants to increase resistance to *Phytophthora sojae*.

Gene constructs of the Rps11 candidate gene, R6 were made using the coding sequence of R6 (SEQ ID NO: 1) from the Rps11 donor line (PI 594527) for overexpression in soybean plants using the *Ochrobactrum*-mediated soybean embryonic axis transformation as previously described (US20180216123A1; WO2020/005933A1; WO2020/092494A1). The R6 gene construct was transformed into a proprietary soybean line that did not carry the Rps11 gene. Single copy T0 transgenic events were selected based on the PCR analysis with primers specific to the cloning vector. T1 seed was harvested for phenotypic confirmation and expression of the Rps11 in plants. Since the T1 plants are expected to segregate for the transgene the screening for *Phytophthora sojae* races was used as an initial confirmation of the expression of the Rps11 candidate gene.

About 20 seedlings from three T1 families were inoculated with four isolates of *Phytophthora sojae*. Each of these isolates were previously tested on the soybean line used for the transformation to confirm that this line is not resistant to these isolates. For the resistance test, lines with less than 25% seedling survival after inoculation were classified as susceptible, lines with 25% to 75% seedling survival after inoculation were classified as heterozygous, and lines with more than 75% seedling survival after inoculation were classified as resistant.

As shown in Table 3 all the T1 families for the Rps11 candidate transgene construct were segregating or resistant to all the isolates, while the transformable line (TG) without Rps11 was susceptible and the Rps11 donor line, PI 594527 was resistant to all the isolates, suggesting that the candidate gene R6 confers increased resistance expression in the soybean plants that were otherwise susceptible to the *Phytophthora sojae* isolates and is therefore the Rps11 gene (Table 3).

For final confirmation of the Rps11 transgene expression in plants for resistance to *Phytophthora sojae*, T2 seed was generated by selling the T1 plants. Homozygous, hemizygous and null T2 plants for the Rps11 candidate transgene were selected based on the PCR analysis. Phenotypic screening of the T2 plants was done using 3 different *Phytophthora sojae* isolates, 25, 31 and 06-03, using same method as was done for the T1 screening. As shown in Table 4, the phenotypic screening results showed significantly higher survival rate in homozygous plants as compared to the null plants with mean percent survival rate after inoculation with *Phytophthora sojae* isolate 31 ranging from 93.5% to 98.8% in homozygous plants and 0% to 11.33% in null plants. Similar level of *Phytophthora* disease resistance response was also observed when inoculated with isolates 31 and 06-03. Dosage effect of the R6 transgene was also observed with hemizygous plants showing intermediate level of resistance as compared to the homozygous and nulls (Table4). These results confirm that the expression of the Rps11 R6 gene provides increased resistance to *Phytophthora sojae*.

TABLE 3

Resistance response of T1 families to Phytophthora sojae isolates

| Genotype[a] | R31 | R25 | 06-03 | OH002 |
|---|---|---|---|---|
| T1-Fam 1 | NE | NE | H | H |
| T1-Fam 2 | H | S[b] | NE | NE |
| T1-Fam 3 | R | R | R | H |
| TG | S | S | S | S |
| P1594527 | R | R | R | R |

[a]T1-Fam represents segregating genotype for Rps11 event; TG- Soybean line used for transformation

[b]Single replication data for 6 plants only

[c]S represents susceptible, R represents resistant, H represents heterozygous (segregation)

TABLE 4

Resistance response in T2 families to *Phytophthora sojae* isolates

| | | | Percent Survival Rate | | | |
|---|---|---|---|---|---|---|
| Event | N | Race | Homozygous | Hemizygous | Null | p-value |
| Event 1 | 11 | 31 | $935^{A}$ (6) | $69.0^{A}$ (2) | $11.33^{B}$ (3) | 7.872e−06 |
| | | 25 | $93.33^{A}$ | $82.0^{A}$ | $40.33^{B}$ | 5.02e−09 |
| | | 06-03 | $74.8^{3A}$ | $61.50^{A}$ | $16.67^{B}$ | 2.29e−04 |
| Event 2 | 13 | 31 | $93.71^{A}$ (7) | $56.67^{B}$ (3) | $0.00^{C}$ (3) | 1.395e−09 |
| | | 25 | $97.43^{A}$ | $52.0^{A}$ | $26.67^{B}$ | 1.42e−07 |
| | | 06-03 | $85.0^{A}$ | $25.0^{B}$ | $2.33^{B}$ | 6.73e−09 |
| Event 3 | 8 | 31 | $98.8^{A}$ (5) | NA | $8.33^{B}$ (3) | 7.306e−07 |
| | | 25 | $92.2^{A}$ | NA | $15.0^{B}$ | 5.461e−05 |
| | | 06-03 | $84.6^{A}$ | NA | $0.00^{B}$ | 5.657e−06 |

N = total no. of T2 lines screened for each event. No. of lines in each genotypic class denoted in parenthesis for race 31. Same no. of lines in each genotypic class was screened for race 31 and 06-03.

Example 4

This example demonstrates the identification of the Rps2b sequence.

PI 594549 C is a soybean landrace identified as a potential source of novel resistance to *Phytophthora sojae* in soybean according to USDA Germplasm Information Network (GRIN).

To determine the resistance of PI 594549 C to various races of *Phytophthora sojae*, disease evaluation was performed using the standard hypocotyl method for all the inoculation experiments. Briefly, 7-day-old seedlings growing in a greenhouse (~25° C.) were tested by injecting 14-day-old *Phytophthora sojae* culture grown on ½ LBA into the hypocotyl of the seedling. In the first day of inoculation, trays holding injected soybean plants were covered by transparent plastic lids to maintain moisture for infection. Disease would further grow for another 5 to 7 days before scoring phenotypes.

For a single plant, if the plant continued to grow after inoculation, it was recorded as resistant, while susceptible would be counted for a dead brown hypocotyl seedling. For a single family, 12 to 36 seedlings were tested dependent on amounts of harvested seeds. If 75% or more seedlings in a family were resistant, then the family was classified as homozygous resistant (R), or homozygous susceptible (S) when less than 25% seedlings were resistant. The remaining families were counted as heterozygous resistant (Rs).

As shown in Table 5, the hypocotyl inoculation studies determined that PI 594594 C was resistant to all *Phytophthora sojae* isolates tested including race 1, race 3, race 4, race 7, race 13, race 17, race 25, four novel isolates from Minnesota (MIN12001.01.05, MIN12001.03.01, MIN12004.01.01 and MIN12005.07.02) and two novel isolates from Indiana (ISA19A-1, ISA71D-1).

TABLE 5

Responses of Soybean Landrace PI 5945493 to Different P. sojae Isolates

| P. sojae isolate | Virulence pathotype | No. of plants examined | No. of plants survived | Phenotype |
|---|---|---|---|---|
| Race 1 | 7 | 12 | 12 | Resistant |
| Race 3 | 1a, 7 | 9 | 10 | Resistant |
| Race 4 | 1a, 1c, 7 | 11 | 10 | Resistant |
| Race 7 | 1a, 2, 3a, 3c, 4, 5, 6, 7 | 10 | 10 | Resistant |
| Race 13 | 4, 6, 7 | 11 | 9 | Resistant |
| Race 17 | 1b, 1d, 2, 3a, 3b, 3c, 4, 5, 6, 7, 8 | 25 | 22 | Resistant |
| Race 25 | 1a, 1b, 1c, 1k, 7 | 10 | 9 | Resistant |
| ISA19A-1 | 1a, 1b, 1k, 4, 6, 7 | 10 | 10 | Resistant |
| ISA71D-1 | 1a, 1c, 1d, 7 | 11 | 10 | Resistant |
| MIN12001.01.05 | NA | 10 | 10 | Resistant |
| MIN12004.01.01 | NA | 10 | 10 | Resistant |
| MIN12004.03.01 | NA | 10 | 10 | Resistant |
| MIN12005.07.02 | NA | 11 | 11 | Resistant |

A single isolate ISA 124C-1 (race 1) was used to characterize the *P. sojae* resistance pattern found in PI 594549 C. By crossing PI 594549 C with the susceptible Williams cultivar, 173 $F_2$ individuals from self-pollination of $F_1$ were generated for a resistance test. For 59 $F_2$ individuals, 50 were resistant and 9 were susceptible, and the null hypothesis that resistance was carried by single dominant locus cannot be rejected ($\chi^2$=2.89, p=0.09) (Table 6). Single locus inheritance pattern was further confirmed by evaluating the 104 $F_{2:3}$ families against *P. sojae* race 1. The segregation of R (homozygous resistant): H (heterozygous resistant): S (homozygous susceptible) observed for resistance to race 1 was 26:48:30, which fits the expected 1:2:1 ratio ($\chi^2$=0.92, p=0.63) (Table 6). In all, these results indicate that the resistance for *P. sojae* race 1 in PI 594549C is carried by a single Rps locus.

TABLE 6

Segregation Ratios of Phenotypes in the Mapping Population

| Parental lines and mapping population | Observed numbers | | | $\chi^2$ goodness of fit test | | |
|---|---|---|---|---|---|---|
| | R | Rs | S | Expected ratio | $\chi^2$ | p |
| PI 594549C | 12 | — | 0 | | | |
| Williams | 0 | — | 12 | | | |
| (PI 594549C × Williams) $F_2$ plants | 50 | — | 9 | 3:1 | 2.89 | 0.09 |
| (PI 594549C × Williams) $F_{2:3}$ families | 26 | 48 | 30 | 1:2:1 | 1.47 | 0.63 |

R-homozygous resistant, Rs-heterozygous resistant, S-homozygous susceptible

To detect chromosomal segments linked to the resistance gene for *P. sojae* race 1 in PI 594549C, ten resistant $F_{2:3}$ families and ten susceptible $F_{2:3}$ families were selected for bulked segregant analysis (BSA). Resistant and susceptible bulks were formed by pooling DNA samples of 10 resistant families and 10 susceptible families separately. The pooled samples were genotyped by the SoySNP6K BeadChip comprising 6210 effective SNP markers together with two parental lines. A total of 2,420 SNPs distributed along the 20 chromosomes were polymorphic between both parents. According to the principle of BSA, in the susceptible bulks, the SNP makers closely linked with the rps locus would be homozygous nucleotides that are the same as shown in the susceptible parental line Williams; whereas in the resistant bulk, such SNPs would be heterozygous nucleotides from both parental lines. Meanwhile, there will be no differences between resistant and susceptible bulks by the SNP markers unlinked with the Rps/rps locus and heterozygous nucleotides would be shown in both bulks. After comparison of the genotypes of the two bulks, a roughly 2-Mb region spanning from about 35 Mb to the end of chromosome 16 (FIG. 3) was found. This region also harbors a previously identified Rps2 and RpsUN2, thus the gene was designated as Rps2b (Rps2 Corteva Agriscience).

According to initial mapping using the BSA method, six polymorphic SSR markers Satt431 (SEQ ID NOs: 20 and 21), BARCSOYSSR_16_1277 (SEQ ID NOs: 22 and 23), BARCSOYSSR_12_1281 (SEQ ID NOs: 24 and 25), BARCSOYSSR_12_1288 (SEQ ID NOs: 26 and 27), BARCSOYSSR_16_1312 (SEQ ID NOs: 32 and 33), BARCSOYSSR_16_1322 (SEQ ID NOs: 34 and 35) from a total of 36 SSR markers were selected for the construction of a linkage map. All markers were observed at the expected 1:2:1 segregation ratio (Table 7), and 18, 11, 10, 9, 8 and 12 recombinants between each of these six markers and the Rps2b locus were defined, respectively. Among these 6 markers, Rps2b is more tightly linked with BARCSOYSSR_16_1288 and BARCSOYSSR_16_1312 compared with the rest of the four markers. A linkage map was constructed with these 6 makers and all markers were consistent with their order annotated on the Williams 82 reference genome (FIG. 4). On the map, Rps2b was defined to a 4.3-cM region flanked by BACSOYSSR_16_1288 and BARCSOYSSR_16_1312, and the physical distance between the two markers is about 444.6 kb.

TABLE 7

Chi-Square ($X^2$) Goodness of Fit Test for the Markers in the $F_2$ Population Deduced Based on the $F_{2:3}$ Progenies Derived from PI 594549c × Williams

| Marker[a] | Observed number[b] | | | $\chi^2$ goodness of fit test | |
|---|---|---|---|---|---|
| | a | h | b | $\chi^2$1:2:1 | p |
| Satt431 | 30 | 46 | 28 | 1.50 | 0.48 |
| BARCSOYSSR_16_1288 | 26 | 47 | 31 | 1.44 | 0.49 |
| BARCSOYSSR_16_1294 | 26 | 47 | 31 | 1.44 | 0.49 |
| BARCSOYSSR_16_1297 | 23 | 51 | 30 | 4.39 | 0.11 |
| BARCSOYSSR_16_1312 | 26 | 49 | 28 | 0.98 | 0.61 |
| BARCSOYSSR_16_1322 | 26 | 50 | 28 | 0.23 | 0.89 |

[a]SSR markers were obtained from Song et al. (2010)
[b]a means homozygous for the marker allele from the resistant PI 594549C; b means homozygous for the marker allele from the susceptible Williams; h means heterozygous for the marker alleles from both parents In order to narrow the mapping region of Rps2b, an $F_3$ population consisting of 1212 individuals and an $F_4$ population containing about 12,000 individuals were developed. Polymorphic KASP markers between PI 594549C and the Williams cultivar were developed from the soybean reference genome Wm82.a1 and were used for genotyping recombinants. The whole genome sequence of PI 594549C was sequenced by PacBio single molecule sequencing platform. No contig harbors both BARCSOYSSR_16_1288 and BARCSOYSSR_16_1312 in the sequencing library. A contig (tig14) harboring BARCSOYSSR_16_1288, BARCSOY, BARSCOYSSR_16_1294, BARCSOYSSR_16_1297 and BARCSOYSSR_16_1302 was used as a reference sequence for finer mapping of the Rps2b gene since it includes all R-genes in the mapping region. The KASP markers which can be uniquely mapped to tig14 were kept for accurate genotyping. There are 25 recombinants defined by BARCSOYSSR_16_1288 and BARCSOYSSR_16_1302, including 3 from the $F_3$ population and 22 from heterozygous-susceptible recombinants of the $F_4$ population. Phenotypes of these recombinants were identified from their derived families by hypocotyl inoculation methods. 2 recombinants (664, 7855) defined Rps2b downstream of KASP marker Gm16_36745870, while 7 recombinants (2123, 3600, 5303, 131-4, 10675, 5643, 31-1) defined the Rps2b upstream of KASP maker Gm16_36789567. For the remaining 16 recombinants, 15 of them were consistent with the 9 key recombinants, while the remaining recombinant defined Rps2b downstream of KASP marker Gm16_36789567. The physical distance between Gm16_36745870 and Gm_36789567 is 32.6 kb on tig14 and 7 genes are located is this region including 4 NBS type R-genes. Rps2 was mapped physically downstream of RpsUN2. Using RpsUN2 as a reference, Rps2b is also a different gene compared with Rps2, but likely to be a new locus of RpsUN2.

By genotyping with two flanking markers, BARCSOYSSR_16_1288 and BARCSOYSSR_16_1312, eight homozygous resistance families were tested with eight homozygous susceptible families as control (Table 8). Rps2b had resistance to 11 of 13 P. sojae isolates, and was susceptible to race 7 and race 17. By comparing Rps2 and RpsUN2, which is also mapped to the end of chromosome 16, Rps2b showed broader resistance as Rps2 showed complete resistance to only 7 of the isolates and RpsUN2 showed resistance to only 6 of the isolates. The results further indicate that Rps2b is a novel Rps gene.

TABLE 8

Marker Assisted Resistance Spectrum Analysis of Rps2b to Isolates of P. sojae

| P. sojae | | $F_{2:3}$ families selected[a] | | Parental lines | | Rps genes on Chr16 | |
|---|---|---|---|---|---|---|---|
| Isolate | Race | Rps2b | Rps2b | PI594549C | Williams | Rps2 | RpsUN2 |
| 124C-1 | 1 | R[b] | S | R | S | R | R |
| 94-14-432(2) | 3 | R | S | R | S | R | R |
| 94-13p-197 | 4 | R | S | R | S | R | I |
| 95-11-117(4) | 7 | S | S | R | S | S | S |
| pmg(13)-1 | 13 | R | S | R | S | S | I |
| pmg(17)-1 | 17 | S | S | R | S | S | S |
| pmg(25)-1 | 25 | R | S | R | S | R | R |
| ISA 19A-1 | N/A | R | S | R | S | I | I |
| ISA 71D-1 | N/A | R | S | R | S | I | I |
| MIN12001.01.05 | N/A | R | S | R | S | R | R |
| MIN12004.01.01 | N/A | R | S | R | S | I | R |
| MIN12004.03.01 | N/A | R | S | R | S | R | R |
| MIN12005.07.02 | N/A | R | S | R | S | R | S |

[a]BARCSOYSSR_16_1288 and BARCSOYSSR_16_1312 are two molecular markers used for selections. The resistance pattern of Rps2b against each P. sojae isolate was scored by the proportion of resistance progenies in 8 selected homozygous resistant $F_{2:3}$ families. The reaction of Rpscas was evaluated from 8 homozygous susceptible $F_{2:3}$ families.
[b]A family was recorded as resistant if >75% of seedlings survived after inoculation, susceptible if <25% of seedlings survived, and intermediate resistant if the proportion of resistant seedlings was between 25% and 75%.

The first of the 4 NBS type R-gene in the fine-mapping region on tig14 was completely shared by PI 594549C and Williams with 100% sequence identity, while the remaining 3 R-genes were not found in the mapping region of Williams 82 reference genome. In recombinants whose phenotypes are susceptible, expression of these 3 genes is not detected, while for recombinants whose genotypes are heterozygous resistant, all these three genes are expressed (FIGS. 5A-5C).

The gene-structure of these three NBS type R-genes were further analyzed and of the three genes only R-gene3 is a complete TIR-NBS-LRR type R-gene. For Rgene2, though the length of its transcript is 4410 bp and shares 99% sequence identity with Glycine soja TMV resistance gene in newly sequenced wild soybean W05 genome, it has a premature stop codon. As a result, the length of its potential longest open reading frame is only 1926 bp which encodes incomplete 641-amino acid R gene carrying only a TIR-NBS domain. For Rgene4, the length of its longest ORF is 1152 bp and also encodes 383-amino acid R gene with only a TIR-NBS domain. Taken together these results indicate that Rgene3 is likely to be the candidate gene for Rps2b.

Example 5

This example demonstrates expression of Rps2b in plants to increase resistance to *Phytophthora sojae*.

A gene construct comprising the Rps2b candidate gene (Rgene3) was made using the CDS of Rgene3 from the Rps2b donor line (PI 594549 C). The Rps2b gene construct was transformed into the susceptible Williams soybean line and single copy T0 transgenic events were selected based on the PCR analysis with primers specific to the cloning vector. Two independent transgenic lines were obtained for further testing.

T2 plants expressing the Rps2b gene, the soybean line $F_5$ RIL (positive control line), and the native Williams line (negative control) were inoculated with *P. sojae* Race 1 and Race 25. As shown in FIGS. 6A and 6B, transgenic lines expressing the Rps2b gene had similar levels of resistance to Race 1 (FIG. 6A) and Race 25 (FIG. 6B) as compared with the $F_5$ RIL line. The expression level of Rps2b in the T2 transgenic lines were similar to the expression level of Rps2b in the $F_5$ RIL line (FIG. 6C), suggesting that the resistance does not result from autoimmunity triggered by the over-expression of an NBS-LRR gene.

Taken together, these results indicate that Rgene3 is the Rps2b gene.\

Example 6

This example demonstrates the identification of the Rps15 sequence.

PI 594592 carries resistance to *P. sojae* races 1, 3, 7 and 25. Evaluation of *P. sojae* resistance/susceptibility to other *Phytophthora sojae* races was examined using a modified hypocotyl inoculation. 7-day-old soybean seedlings growing in a greenhouse (about 25° C.) were inoculated with mycelial slurry from 14-day-old isolates maintained on ½ LBA media. A small incision was made approximately 1 cm below the cotyledon for insertion of mycelium into the wound. After inoculation, each tray holding seedlings was covered with a transparent plastic lid for one day to create an environment with a high humidity level to promote infection. Before scoring phenotypes, disease growth was maintained for another 5-7 days after removal of the lid.

For a single plant, if the seedling kept growing after inoculation, it was recorded as resistant, and if the seedlings died with necrosis in the hypocotyl it was marked as susceptible. 20 to 36 progeny was analyzed for phenotype scoring for each family. A family was classified as homozygous resistant (R) if no less than 75% progenies survived, segregating (Rs) if 25-75% of progenies survived, or heterozygous susceptible (S) if less than 25% of the seedlings were alive.

As shown in Table 9, resistance to *P. sojae* races 1, 3, 7 and 25 was confirmed and it was further determined that PI 594592 carries resistance to *P. sojae* races 4, 13, 17, and two newly found predominant isolates collected from soybean fields in Indiana (ISA19A-1, ISA17D-1) and four isolates collected from soybean fields in Minnesota (MIN12001.01.05, MIN12004.01.01, MIN12004.03.01 and MIN12005.07.02).

TABLE 9

Responses of Soybean Landrace PI 594592 to Different P. sojae Isolates

| P. sojae isolate | Virulence pathotype | No. of plants examined | No. of plants survived | Phenotype |
|---|---|---|---|---|
| Race 1 | 7 | 10 | 10 | Resistant |
| Race 3 | 1a, 7 | 11 | 11 | Resistant |
| Race 4 | 1a, 1c, 7 | 10 | 10 | Resistant |
| Race 7 | 1a, 2, 3a, 3c, 4, 5, 6, 7 | 12 | 11 | Resistant |
| Race 13 | 4, 6, 7 | 11 | 11 | Resistant |
| Race 17 | 1b, 1d, 2, 3a, 3b, 3c, 4, 5, 6, 7, 8 | 12 | 11 | Resistant |
| Race 25 | 1a, 1b, 1c, 1k, 7 | 10 | 10 | Resistant |
| ISA19A-1 | 1a, 1b, 1k, 4, 6, 7 | 11 | 11 | Resistant |
| ISA71D-1 | 1a, 1c, 1d, 7 | 11 | 11 | Resistant |
| MIN12001.01.05 | NA | 10 | 10 | Resistant |
| MIN12004.01.01 | NA | 10 | 10 | Resistant |
| MIN12004.03.01 | NA | 11 | 11 | Resistant |
| MIN12005.07.02 | NA | 10 | 10 | Resistant |

To determine the inheritance pattern of *P. sojae* resistance in PI 594592, 60 $F_2$ plants derived from a cross between PI 594592 and the Williams cultivar were tested using race 1. Of the 60 plants, 46 were resistant to race 1, while 14 were susceptible. This observation suggests that resistance to *P. sojae* race 1 is carried by a single locus in PI 594592 since the segregation fits a phenotypic ratio of 3:1($x^2$=0.09, p=0.77) (Table 10). 200 $F_{2:3}$ families from $F_2$ plants were subsequently developed by self-pollination, and tested for resistance to race 1. Among these 200 families, 47 were homozygous resistant (R), 107 showed heterozygous resistance, and 50 were homozygous susceptible, which fit a phenotypic ratio of 1:2:1 (($\chi^2$=0.09, p=0.77). This observation further indicates the resistance to *P. sojae* race1 is conferred by a single locus.

TABLE 10

Segregation Ratios of Phenotypes in the Mapping Population

| Parental lines and mapping population | Observed numbers R | Rs | S | $\chi^2$ goodness of fit test Expected ratio | $\chi^2$ | p |
|---|---|---|---|---|---|---|
| PI 594592 | 12 | — | 0 | | | |
| Williams | 0 | — | 12 | | | |
| (PI 594592 × Williams) $F_2$ plants | 46 | — | 14 | 3:1 | 0.09 | 0.77 |
| (PI 594592 × Williams) $F_{2:3}$ families | 43 | 107 | 50 | 1:2:1 | 1.47 | 0.48 |

R-homozygous resistant, Rs-heterozygous resistant, S-homozygous susceptible 10 completely susceptible $F_{2:3}$ families and 10 completely resistant $F_{2:3}$ families were selected to make up susceptible and resistant bulks. The resistant and susceptible bulks, along with the two parental lines Williams and PI 594592, were genotyped with the SoySNP6K Infinium BeadChips consisting of 6000 SNP markers. In total, there are 2509 polymorphic SNPs distributed along all 20 chromosomes between the two parental lines. If there were differences detected between resistant and susceptible bulks, and the SNP markers detected homozygous nucleotides that are same as shown in the resistant parental line PI 594592, then the SNP markers are believed to closely linked to Rps locus. Based on this principle, a ~6.5 Mb genomic region on chromosome 16 showing homozygous SNP sites in resistant bulk and heterozygous SNP sites in susceptible bulk was identified, starting from ~30.8 Mb to the end of chromosome16 according to soybean reference genome Wm82.a1 (Table 11 and FIG. 7).

TABLE 11

Genotypic Comparison Between the Resistant and Susceptible Bulks at the SNP Sites Detected Between the Two Parental Lines at the End of Chromosome 16

| SNP ID | Chromosome | Position(bp) | Williams | Susceptible Bulk | Resistant Bulk | PI 594592 |
|---|---|---|---|---|---|---|
| SNP1912 | Gm16 | 28266706 | TT | TC | TC | CC |
| SNP1913 | Gm16 | 28407237 | AA | AC | AC | CC |
| SNP1914 | Gm16 | 28443553 | TT | TC | TC | CC |
| SNP1915 | Gm16 | 28613278 | CC | TC | TC | TT |
| SNP1916 | Gm16 | 28706800 | AA | AG | AG | GG |
| SNP1917 | Gm16 | 29985920 | AA | AG | AG | GG |
| SNP1918 | Gm16 | 30038668 | GG | TG | TG | TT |
| SNP1919 | Gm16 | 30108889 | CC | AC | AC | AA |
| SNP1920 | Gm16 | 30813568 | GG | TG | TT | TT |
| SNP1921 | Gm16 | 31454423 | GG | AG | AA | AA |
| SNP1922 | Gm16 | 31787658 | TT | TC | CC | CC |
| SNP1923 | Gm16 | 31837545 | CC | TC | TT | TT |
| SNP1924 | Gm16 | 31899513 | GG | AG | AA | AA |
| SNP1925 | Gm16 | 32017661 | AA | AC | CC | CC |
| SNP1926 | Gm16 | 32200441 | AA | AC | CC | CC |
| SNP1927 | Gm16 | 32340079 | GG | AG | AA | AA |
| SNP1928 | Gm16 | 32665742 | TT | TC | CC | CC |
| SNP1929 | Gm16 | 32876100 | AA | AG | GG | GG |
| SNP1930 | Gm16 | 33210540 | TT | TC | CC | CC |
| SNP1931 | Gm16 | 33360539 | TT | TC | CC | CC |
| SNP1932 | Gm16 | 33457667 | TT | TT | GG | GG |
| SNP1933 | Gm16 | 34645180 | AA | AG | GG | GG |
| SNP1934 | Gm16 | 35148803 | TT | TG | GG | GG |
| SNP1935 | Gm16 | 35218386 | GG | TG | TT | TT |
| SNP1936 | Gm16 | 35643452 | CC | TC | TT | TT |
| SNP1937 | Gm16 | 35700223 | GG | TG | TT | TT |
| SNP1938 | Gm16 | 35738081 | AA | AG | GG | GG |
| SNP1939 | Gm16 | 36013043 | AA | AC | AA | CC |
| SNP1940 | Gm16 | 36217195 | TT | TC | CC | CC |
| SNP1941 | Gm16 | 36732450 | TT | TT | CC | CC |
| SNP1942 | Gm16 | 36983033 | CC | CC | AA | AA |
| SNP1943 | Gm16 | 37078478 | AA | AA | GG | GG |
| SNP1944 | Gm16 | 37209075 | TT | TT | GG | GG |

In order to fine map the Rps gene, the re-sequencing data of the two parental lines combined with the reference genome was used in marker design. 10 InDel markers in the defined region were designed and confirmed for polymorphism between the two parental lines. 6 potential SSR markers that are closely linked with two previously identified Rps genes, Rps2 and RpsUN2 were also tested. These markers also showed polymorphism between the two parental lines (Table 12). These 16 markers are evenly distributed within the defined ~6.5 Mb Rps15 region and were used for genotyping 200 $F_{2:3}$ families. Each of these markers revealed a 1:2:1 ratio for three possible genotypes (R, Rs, S) in the mapping population (Table 13). Combining all the genotypic and phenotypic data from the $F_{2:3}$ families, a linkage map comprising all the sixteen markers in the Rps15 locus (FIG. 8) was constructed. In the map, Rps15 is flanked by SSR marker Satt431 and InDel marker InDel3618, and the genetic distance to Rps15 were 3.6 and 1.4 cM, respectively. According to the soybean Williams82 reference genome, the 5 cM region corresponds to a roughly 462 kb region harboring 58 different genes (Table 14).

TABLE 12

Polymorphic Insertion/Deletion (InDel) and SSR Markers Identified Between PI594592 and Williams

| SSR Marker | Chr | Forward primer | Reverse primer |
|---|---|---|---|
| InDel3155 | 16 | SEQ ID NO: 86 | SEQ ID NO: 87 |
| InDel3255 | 16 | SEQ ID NO: 88 | SEQ ID NO: 89 |
| InDel3304 | 16 | SEQ ID NO: 90 | SEQ ID NO: 91 |
| InDel3437 | 16 | SEQ ID NO: 92 | SEQ ID NO: 93 |
| InDel3575 | 16 | SEQ ID NO: 94 | SEQ ID NO: 95 |
| InDel3586 | 16 | SEQ ID NO: 96 | SEQ ID NO: 97 |
| InDel3668 | 16 | SEQ ID NO: 98 | SEQ ID NO: 99 |
| InDel3678 | 16 | SEQ ID NO: 100 | SEQ ID NO: 101 |
| InDel3701 | 16 | SEQ ID NO: 102 | SEQ ID NO: 103 |
| Satt431 | 16 | SEQ ID NO: 20 | SEQ ID NO: 21 |
| BARCSOYSSR_16_1288 | 16 | SEQ ID NO: 26 | SEQ ID NO: 27 |
| BARCSOYSSR_16_1294 | 16 | SEQ ID NO: 28 | SEQ ID NO: 29 |
| BARCSOYSSR_16_1297 | 16 | SEQ ID NO: 30 | SEQ ID NO: 31 |
| BARCSOYSSR_16_1312 | 16 | SEQ ID NO: 32 | SEQ ID NO: 33 |
| BARCSOYSSR_16_1322 | 16 | SEQ ID NO: 34 | SEQ ID NO: 35 |

TABLE 13

Chi-Square ($X^2$) Goodness of Fit Test for the Markers in the $F_2$ Population
Deduced Based on the $F_{2:3}$ Progenies Derived From Pi 594592 × Williams

| Marker | Observed number[a] | | | $\chi^2$ goodness of fit test | |
|---|---|---|---|---|---|
| | a | h | b | $\chi^2$1:2:1 | p |
| | 43 | 107 | 50 | 1.47 | 0.48 |
| InDel3155 | 48 | 103 | 49 | 0.19 | 0.91 |
| InDel3255 | 50 | 98 | 52 | 0.12 | 0.94 |
| InDel3304 | 47 | 106 | 47 | 0.72 | 0.70 |
| InDel3437 | 48 | 105 | 47 | 0.51 | 0.77 |
| InDel3575 | 44 | 109 | 47 | 1.71 | 0.43 |
| InDel3586 | 44 | 109 | 47 | 1.71 | 0.43 |
| Satt431 | 47 | 104 | 49 | 0.36 | 0.84 |
| InDel3668 | 45 | 106 | 49 | 0.88 | 0.64 |
| InDel3678 | 45 | 109 | 46 | 1.63 | 0.44 |
| InDel3701 | 43 | 110 | 47 | 2.16 | 0.34 |
| BARCSOYSSR_16_1288 | 40 | 113 | 47 | 3.87 | 0.14 |
| BARCSOYSSR_16_1294 | 41 | 113 | 46 | 3.63 | 0.16 |
| BARCSOYSSR_16_1297 | 41 | 112 | 47 | 3.24 | 0.20 |
| BARCSOYSSR_16_1312 | 42 | 112 | 46 | 3.04 | 0.22 |
| BARCSOYSSR_16_1322 | 44 | 110 | 46 | 2.04 | 0.36 |

[a] a means homozygous for the marker allele from the resistant PI 594592; b means homozygous for the marker allele from the susceptible Williams; h means heterozygous for the marker alleles from both parents

TABLE 14

Gene Annotation in the Mapped Region
According to the Soybean Reference Genome (Wm82.a2. v1)

| Genes | Annotation |
|---|---|
| Glyma.16g200900 | MEMBER OF 'GDXG' FAMILY OF LIPOLYTIC ENZYMES |
| Glyma.16g201000 | MEMBER OF 'GDXG' FAMILY OF LIPOLYTIC ENZYMES |
| Glyma.16g201100 | Helix-loop-helix DNA-binding domain |
| Glyma.16g201200 | LEUCINE-RICH REPEAT RECEPTOR-LIKE PROTEIN KINASE |
| Glyma.16g201300 | Helix-loop-helix DNA-binding domain |
| Glyma.16g201400 | Helix-loop-helix DNA-binding domain |
| Glyma.16g201500 | LEUCINE-RICH REPEAT RECEPTOR-LIKE PROTEIN KINASE |
| Glyma.16g201600 | EXOSTOSIN (HEPARAN SULFATE GLYCOSYLTRANSFERASE)-RELATED |
| Glyma.16g201700 | PROPROTEIN CONVERTASE SUBTILISIN/KEXIN |
| Glyma.16g201800 | Transferase family |
| Glyma.16g201900 | cysteine-rich RLK (RECEPTOR-like protein kinase) 25 |
| Glyma.16g202000 | Embryo-specific protein 3 |
| Glyma.16g202100 | cysteine-rich RLK (RECEPTOR-like protein kinase) 25 |
| Glyma.16g202200 | LEUCINE-RICH REPEAT RECEPTOR-LIKE PROTEIN KINASE |
| Glyma.16g202300 | HXXXD-type acyl-transferase family protein |
| Glyma.16g202400 | LEUCINE-RICH REPEAT RECEPTOR-LIKE PROTEIN KINASE |
| Glyma.16g202500 | Embryo-specific protein 3 |
| Glyma.16g202600 | F-box family protein |
| Glyma.16g202700 | 40S RIBOSOMAL PROTEIN S14/30S RIBOSOMAL PROTEIN S11 |
| Glyma.16g202800 | F-box family protein |
| Glyma.16g202900 | F-box family protein |
| Glyma.16g203000 | F-box family protein |
| Glyma.16g203100 | Iron-binding zinc finger CDGSH type |
| Glyma.16g203200 | POTASSIUM/PROTON ANTIPORTER-RELATED |
| Glyma.16g203300 | LEUCINE-RICH REPEAT RECEPTOR-LIKE PROTEIN KINASE |
| Glyma.16g203400 | BOX C/D SNORNA PROTEIN 1 |
| Glyma.16g203500 | RING FINGER DOMAIN-CONTAINING |
| Glyma.16g203600 | 1-AMINOCYCLOPROPANE-1-CARBOXYLATE SYNTHASE |
| Glyma.16g203700 | GLUTAMATE DEHYDROGENASE/NADP-SPECIFIC GLUTAMATE DEHYDROGENASE 1-RELATED |
| Glyma.16g203800 | No functional annotations |
| Glyma.16g203900 | DNA REPAIR/RNA PROCESSING CPSF FAMILY/CLEAVAGE AND POLYADENYLATION SPECIFICITY FACTOR SUBUNIT 1 |
| Glyma.16g204000 | ATP-DEPENDENT CLP PROTEASE |
| Glyma.16g204100 | ATP-DEPENDENT CLP PROTEASE |
| Glyma.16g204200 | BED zinc finger/hAT family C-terminal dimerisation region |
| Glyma.16g204300 | PROTEIN REGULATOR OF CYTOKINESIS 1 PRC1-RELATED |
| Glyma.16g204400 | No functional annotations |
| Glyma.16g204500 | integral component of membrane |
| Glyma.16g204600 | Enolase, C-terminal TIM barrel domain/Enolase, N-terminal domain |
| Glyma.16g204700 | nucleic acid binding |
| Glyma.16g204800 | Tetratricopeptide repeat (TPR)-like superfamily protein |
| Glyma.16g204900 | SPFH domain/Band 7 family |
| Glyma.16g205000 | No functional annotation |
| Glyma.16g205100 | LEUCINE-RICH REPEAT RECEPTOR-LIKE PROTEIN KINASE |

TABLE 14-continued

Gene Annotation in the Mapped Region
According to the Soybean Reference Genome (Wm82.a2. v1)

| Genes | Annotation |
|---|---|
| Glyma.16g205200 | CHLOROPHYLL A/B BINDING PROTEIN |
| Glyma.16g205300 | integral component of membrane |
| Glyma.16g205400 | No functional annotation |
| Glyma.16g205500 | APO PROTEIN 1, CHLOROPLASTIC |
| Glyma.16g205600 | No functional annotation |
| Glyma.16g205700 | AAA domain (Cdc48 subfamily)/C-terminal, D2-small domain, of ClpB protein |
| Glyma.16g205800 | No functional annotation |
| Glyma.16g205900 | No functional annotation |
| Glyma.16g206000 | Pentatricopeptide repeat (PPR) superfamily protein |
| Glyma.16g206100 | Trypsin and protease inhibitor |
| Glyma.16g206200 | Hsp20/alpha crystallin family |
| Glyma.16g206300 | Trypsin and protease inhibitor |
| Glyma.16g206400 | chloroplast relocation |
| Glyma.16g206500 | Ribosomal Proteins L2, C-terminal domain |
| Glyma.16g206600 | ATP binding; nucleic acid binding; helicases |

Previously, RpsUN2 was fine mapped downstream of BARCSOY_SSR_1288 and Rps15 is 7.7 cM upstream of the same marker. Meanwhile, Rps2 was mapped 12.2 cM downstream to Satt431, which means the genetic distance between Rps15 and Rps2 is about 8.6 cM. This result suggests that Rps15 is more likely to be a novel Rps gene rather than a new allele for Rps2 or RpsUN2.

Of the 13 isolates of P. sojae used, Rps15 conferred resistance to 12 isolates and only showed susceptibility to Race 7 (Table 15). Rps2 was resistant to 7 isolates, partially resistant to 4, and susceptible to 3 (Race7, Race 13 and Race 17). RpsUN2 was resistant to 6 isolates, with intermediate resistance to 4 and susceptibility to 4. (Race 7, Race 17 and MIN12005.07.02). These results indicated that Rps15 had a much broader resistance spectrum compared with Rps2 and RpsUN2.

phenotyped with Phytophthora sojae isolate Race 1. Based on the fine mapping, the Rps15 QTL region will be narrowed down to a smaller genomic interval comprising a few candidate genes for further confirmation. To identify candidate genes for Rps15, a whole genome sequence of PI 594592 will be generated using the PacBio sequencing platform. A contig harboring the flanking markers for the Rps15 genomic interval will be used as a reference sequence for comparing to the sequence data from the susceptible lines, characterizing the genes and identifying candidate genes based on the NBS type R-genes as candidates for Rps15. The NBS type R-genes will be further analyzed for their gene structure to determine if it is a complete NBS type gene or truncated. Gene expression analysis will also be done to determine the expression profile of the NBS type R-genes in the recombinants. Together, with these analyses

TABLE 15

Marker Assisted Resistance Spectrum Analysis of Rps15 to Isolates of P. sojae

| P. sojae | | $F_{2:3}$ families selected[a] | | Parental lines | | Rps genes on Chr16 | |
|---|---|---|---|---|---|---|---|
| Isolate | Race | Rps15 | Rps15 | PI 594592 | Williams | Rps2 | RpsUN2 |
| 124C-1 | 1 | R[b] | S | R | S | R | R |
| 94-14-432(2) | 3 | R | Segregation | R | S | R | R |
| 94-13p-197 | 4 | R | S | R | S | R | I |
| 95-11-117(4) | 7 | S | S | R | S | S | S |
| pmg(13)-1 | 13 | R | Segregation | R | S | S | I |
| pmg(17)-1 | 17 | R | Segregation | R | S | S | S |
| pmg(25)-1 | 25 | R | S | R | S | R | R |
| ISA 19A-1 | N/A | R | S | R | S | I | I |
| ISA 71D-1 | N/A | R | S | R | S | I | I |
| MIN12001.01.05 | N/A | R | S | R | S | R | R |
| MIN12004.01.01 | N/A | R | S | R | S | I | R |
| MIN12004.03.01 | N/A | R | S | R | S | R | R |
| MIN12005.07.02 | N/A | R | S | R | S | R | S |

[a]Satt431 and InDel3668 are two molecular markers used for selections. The resistance pattern of Rps15 against each P. sojae isolate was scored by the proportion of resistance progenies in 8 selected homozygous resistant $F_{2:3}$ families The reaction of Rps15 was evaluated from 8 homozygous susceptible $F_{2:3}$ families
[b]A family was recorded as resistant if >75% of seedlings survived after inoculation, susceptible if <25% of seedlings survived, and intermediate resistant if the proportion of resistant seedlings was between 25% and 75%.

To further determine the candidate gene for Rps15, NBS type R-genes, such as those provided in Table 14, will be identified in the Rps15 locus and analyzed. The Rps15 genomic interval will be further fine mapped using a large $F_3$ mapping population derived from a cross between PI 594592 and the susceptible parental Williams cultivar. The mapping population will be genotyped with molecular markers to identify recombinant lines. The recombinants will be candidate genes will be expected to be identified for Rps15. Constructs comprising the candidate genes will be generated and transformed into soybean lines that do not carry the Rps15 candidate gene to confirm the Rps15 candidate gene and determining if expression of Rps15 candidate gene in plants increases resistance to Phytophthora sojae.

Single copy T0 transgenic events will be selected based on the PCR analysis with primers specific to the cloning vector. Final confirmation of the Rps15 gene expression in plants for resistance to *Phytophthora sojae* will be done in the homozygous T2 plants for the Rps15 candidate gene. T2 plants homozygous for the Rps15 candidate gene will be expected to increase resistance to *Phytophthora sojae* isolates as compared to plants not carrying the Rps15 gene. These results would confirm the Rps15 gene.

Example 7

This example demonstrates the identification of the Rps14 sequence.

PI 340029 carries broad resistance to *P. sojae*, including *P. sojae* races 1, 2, 3, 4, 5, 6, 7, 8, and 9. To determine if PI 340029 carries resistance to other races of *P. sojae* hypocotyl inoculation, as described above, was performed. As shown in Table 16, the hypocotyl inoculation studies determined PI 340029 also shows resistance to race 13, race 17, race 25, and two other isolates (ISA19A-1, ISA71D-1) from Indiana soybean fields and four isolates (MIN12001.01.05, MIN12004.01.01, MIN12004.03.01 and MIN12005.07.02) from Minnesota whose pathotypes that do not match any known *P. sojae* race designations. These findings demonstrate that PI 340029 can be a new source for broad *P. sojae* resistance.

TABLE 16

Responses of Soybean Landrace PI 340029 to Different *P. sojae* Isolates

| *P. sojae* Isolate | Virulence Pathlotype | No. of plants examined | No. of plants survived | No. of plants killed | Proportion of resistant | Phenotype |
|---|---|---|---|---|---|---|
| Race1 | 7 | 12 | 12 | 0 | 1.00 | Resistant |
| Race17 | 1b, 1d, 2, 3a, 3b, 3c, 4, 5, 6, 7, 8 | 24 | 24 | 0 | 1.00 | Resistant |
| Race25 | 1a, 1b, 1c, 1k, 7 | 12 | 12 | 0 | 1.00 | Resistant |
| Race13 | 4, 6, 7 | 8 | 8 | 0 | 1.00 | Resistant |
| ISA 19A-1 | 1a, 1b, 1k, 4, 6, 7 | 10 | 10 | 0 | 1.00 | Resistant |
| ISA 71D-1 | 1a, 1c, 1d, 7 | 7 | 7 | 0 | 1.00 | Resistant |
| MIN12001.01.05 | NA | 10 | 10 | 0 | 1.00 | Resistant |
| MIN12004.01.01 | NA | 9 | 9 | 0 | 1.00 | Resistant |
| MIN12004.03.01 | NA | 10 | 10 | 0 | 1.00 | Resistant |
| MIN12005.07.02 | NA | 10 | 10 | 0 | 1.00 | Resistant |
| *Race2 | 1a, 7 | — | — | — | — | Resistant |
| *Race3 | 1a, 2, 3a, 3c, 4, 5, 6, 7 | — | — | — | — | Resistant |
| *Race4 | 1a, 1c, 5, 7 | Resistant | | | | |
| *Race5 | 1a, 1c, 2, 4, 6, 7 | Resistant | | | | |
| *Race6 | 1a, 1d, 3a, 6, 7 | Resistant | | | | |
| *Race7 | 1a, 2, 3a, 3c, 4, 5, 6, 7 | Resistant | | | | |
| *Race8 | 1a, 1d, 6, 7 | Resistant | | | | |
| *Race9 | 1a, 6, 7 | Resistant | | | | |

*P. sojae* isolates previously used to evaluate PI 340029

By crossing PI 340029 with the susceptible Williams cultivar, 167 $F_2$ individuals were produced from self-pollination of the $F_1$. 57 $F_2$ plants were tested for resistance to *P. sojae* race 1, of the 57 F2 plants, 48 were identified as resistant and 9 were identified as susceptible (Table 17). The null hypothesis that resistance was carried by a single locus cannot be rejected ($\chi^2$=2.58, p=0.11). In order to get more accurate phenotypes, $F_{2:3}$ families were tested for resistance to *P. sojae* race 1, the isolate avirulent to most known Rps genes. After harvesting seeds from the remaining $F_2$ plants, 20 to 36 $F_3$ seedlings were tested. Among 110 $F_{2:3}$ families, the segregation ratio of R (homozygous resistant): Rs (segregating): S (homozygous susceptible) observed for response to *P. sojae* race 1 was 28:48:34, which fits the expected ratio for 1:2:1 ($\chi^2$=3.4, p=0.30) (Table 17). This indicates that resistance for *P. sojae* race 1 in PI 340029 is carried by a single Rps locus.

TABLE 17

Segregation Ratios of Phenotypes in the Mapping Population

| Parental lines and mapping population | Observed numbers | | | $\chi^2$ goodness of fit test | | |
|---|---|---|---|---|---|---|
| | R* | Rs | S | Expected ratio | $\chi^2$ | p |
| PI 340029 | 12 | — | 0 | | | |
| Williams | 0 | — | 12 | | | |
| (PI 340029 × Williams) $F_2$ plants | 48 | — | 9 | 3:1 | 2.58 | 0.11 |
| (PI 340029 × Williams) $F_{2:3}$ families | 28 | 48 | 34 | 1:2:1 | 3.4 | 0.30 |

*R-homozygous resistant, Rs-heterozygous resistant, S-homozygous susceptible

To detect the genetic region linked to the resistance gene in PI 340029, bulked segregant analysis was performed to initially map the Rps gene on a chromosomal segment. 10 completely susceptible $F_{2:3}$ families and 10 completely resistant $F_{2:3}$ families were selected to make up the susceptible and resistant bulks. SoySNP6K BeadChip consisting of 7039 SNPs was used to genotype both bulks and the two parental lines. There are 1983 SNPs markers in all 20 chromosomes showing polymorphisms between the two parental lines, which were effective and reliable for BSA analysis. After comparing the genotypes of the two bulks, a ~5.8 Mb region was found at the beginning of chromosome 3, on which homozygous nucleotides that are the same as the susceptible parental Williams cultivar were found, while these nucleotides were found heterozygous from both parental lines in the resistance bulk (Table 18). Since no other regions on other chromosomes were found to be different between the two bulks, the chromosomal segment on chromosome 3 is considered closely linked with the rps locus according to the principle of BSA (FIG. 9). Since the region overlaps with some of previously defined Rps1 alleles/genes, the gene on this region was designated Rps14.

TABLE 18

Illustration of Genotypic Comparison Between the Resistant and Susceptible Bulks at the SNP Sites Detected Between the Two Parental Lines at the Beginning of Chromosome 3

| SNP ID | Chromosome | Position (bp) | PI340029 | Resistant Bulk | Susceptible Bulk | Williams |
|---|---|---|---|---|---|---|
| SNP178 | Gm03 | 829023 | TT | TG | GG | GG |
| SNP179 | Gm03 | 1671384 | AA | AC | CC | CC |
| SNP180 | Gm03 | 1718435 | GG | AG | AA | AA |
| SNP181 | Gm03 | 1758253 | CC | TC | TC | TT |
| SNP183 | Gm03 | 2818076 | CC | TC | TC | TT |
| SNP184 | Gm03 | 3087237 | AA | AG | GG | GG |
| SNP185 | Gm03 | 3907697 | GG | AG | AA | AA |
| SNP186 | Gm03 | 4487138 | CC | AC | AA | AA |
| SNP187 | Gm03 | 4509101 | AA | AG | GG | GG |
| SNP188 | Gm03 | 4665923 | CC | TC | TT | TT |
| SNP189 | Gm03 | 4782127 | CC | TC | TT | TT |
| SNP190 | Gm03 | 4903317 | GG | AG | AG | AA | with the other four markers. A linkage map was constructed with these five markers and all the five markers were in good agreement with their order annotated on the Williams 82 reference genome (FIG. 10). The Rps14 locus was narrowed to a 4.5 cM region flanked by BARCSOYSSR_03_0226 and BARCSOYSSR_03_0266.

TABLE 19

Polymorphic Insertion/Deletion and SSR Markers Identified Between PI340029 and Williams

| SSR Marker | Ch | Forward primer | Reverse primer |
|---|---|---|---|
| Satt631 | 03 | SEQ ID NO: 104 | SEQ ID NO: 105 |
| BARCSOYSSR_03_0209 | 03 | SEQ ID NO: 106 | SEQ ID NO: 107 |
| BARCSOYSSR_03_0219 | 03 | SEQ ID NO: 108 | SEQ ID NO: 109 |
| BARCSOYSSR_03_0226 | 03 | SEQ ID NO: 110 | SEQ ID NO: 111 |
| BARCSOYSSR_03_0229 | 03 | SEQ ID NO: 112 | SEQ ID NO: 113 |
| BARCSOYSSR_03_0266 | 03 | SEQ ID NO: 114 | SEQ ID NO: 115 |
| InDel3971 | 03 | SEQ ID NO: 116 | SEQ ID NO: 117 |
| InDel4033 | 03 | SEQ ID NO: 118 | SEQ ID NO: 119 |
| InDel4263 | 03 | SEQ ID NO: 120 | SEQ ID NO: 121 |
| InDel4330 | 03 | SEQ ID NO: 122 | SEQ ID NO: 123 |

TABLE 20

Chi-Square ($X^2$) Goodness of Fit Test for the Markers in the $F^2$ Population Deduced Based on the $F_{2:3}$ Progenies Derived From Pi 594592 × Williams

| | Observed number[a] | | | $\chi^2$ goodness of fit test | |
|---|---|---|---|---|---|
| Marker | a | h | b | $\chi^2 1:2:1$ | p |
| Satt631 | 25 | 50 | 34 | 2.23 | 0.33 |
| BARCSOYSSR_03_0209 | 25 | 50 | 35 | 2.73 | 0.26 |
| BARCSOYSSR_03_0219 | 25 | 50 | 35 | 2.73 | 0.26 |
| BARCSOYSSR_03_0226 | 25 | 50 | 35 | 2.73 | 0.26 |
| BARCSOYSSR_03_0266 | 30 | 46 | 34 | 3.24 | 0.20 |

[a] a means homozygous for the marker allele from the resistant PI 594592; b means homozygous for the marker allele from the susceptible Williams; h means heterozygous for the marker alleles from both parents TABLE 18-continued Illustration of Genotypic Comparison Between the Resistant and Susceptible Bulks at the SNP Sites Detected Between the Two Parental Lines at the Beginning of Chromosome 3

| SNP ID | Chromosome | Position (bp) | PI340029 | Resistant Bulk | Susceptible Bulk | Williams |
|---|---|---|---|---|---|---|
| SNP191 | Gm03 | 5165511 | AA | AC | CC | CC |
| SNP192 | Gm03 | 5217414 | CC | TC | TT | TT |
| SNP193 | Gm03 | 5796468 | AA | AG | AG | GG |
| SNP194 | Gm03 | 6631189 | GG | AG | AG | AA |
| SNP195 | Gm03 | 6844115 | CC | AC | AC | AA |
| SNP196 | Gm03 | 8003327 | TT | TC | TC | CC |
| SNP197 | Gm03 | 8228940 | AA | AG | AG | GG |
| SNP198 | Gm03 | 9641204 | AA | AC | AC | CC |

Based on the initial mapping results, a series of potential SSR markers located on the region mapped by BSA were screened and 5 markers, Satt631, BARCSOYSSR_03_0209, BARCSOYSSR_03_0219, BARCSOYSSR_03_0226 and BARCSOYSSR_03_0226, which showed clear polymorphisms between the two parental lines were identified (Table 19). These 5 markers were chosen to genotype all 110 $F_{2:3}$ families. As expected, all markers observed a 1:2:1 segregation ratio, and 9, 4, 4, 2 and 6 recombinants between each of these five markers and the Rps14 locus were defined, respectively (Table 20). Among these 5 markers, Rps14 is more closely linked to BARCSOYSSR_03_0226 compared In order to narrow the mapping region of Rps14, two SSR markers, BARCSOYSSR_03_0219 and BARCSOYSSR_03_0266, were selected to genotype $F_3$ plants and 21 recombinants were identified. Subsequently, the $F_{3:4}$ families derived from these recombinants were tested with P. sojae race 1. One additional SSR polymorphism marker and four InDel markers developed from comparison between re-sequencing data of two parental lines to genotype these recombinants by pooling of $F_4$ seedlings from $F_{3:4}$ families was also used. Four recombinants (205-1, 83-3, 161-1, 174-2) defined the Rps14 locus to downstream of marker InDel4033, while 3 recombinants (59-8, 12-2, 152-5) defined the Rps14 locus to upstream of marker InDel4263. For the remaining 16 recombinants, genotypes and phenotypes were all consistent with the seven key recombinants. Therefore, the Rps14 was further mapped to the region flanked by InDel4033 and InDel4263, which defined a ~229 kb region based on the Williams 82 soybean reference genome.

Previously, RpsUN1 was fine mapped to a ~151kb region defined by BARCSOYSSR_03_0233 and BARCSOYSSR_03_0246 (Li et al. 2016). The Rps14 region is ~137kb overlapped with fine mapped RpsUN1 region based on Williams 82 reference genome. There are 7 genes in that region including three predicted R genes with NBS_LRR domains (Table 21).

TABLE 21

Gene Annotation in the Mapped Region
According to the Soybean Reference Genome (Wm82.a2.v1)

| Genes | Annotation |
|---|---|
| Glyma.03g034500 | NB-ARC domain-containing disease resistance protein |
| Glyma.03g034600 | AAA-type ATPase family protein |
| Glyma.03g034700 | zinc ion binding; nucleic acid binding |
| Glyma.03g034800 | NB-ARC domain-containing disease resistance protein |
| Glyma.03g034900 | LRR and NB-ARC domains-containing disease resistance protein |
| Glyma.03g035000 | Nucleic acid-binding, OB-fold-like protein |
| Glyma.03g035100 | PIF1-like helicase |

RNA-seq revealed that only three genes expressed in the P. sojae infection process in the resistance donor line PI 340029, namely Glyma.03g034500, Glyma.03g034800 and Glyma.03g034900 according to reference genome Wms82.v2. a1. All these three genes were annotated to encode NBS_LRR proteins. In the susceptible donor line Williams, these three genes show no or extremely low levels of expression in the process of P. sojae infection. Therefore, these three genes are all candidate genes for Rps14.

Previously, Rps1 (Rps1a, Rps1b, Rps1c, Rps1d, Rps1k), RpsUN1, Rps7 and Rps9 were also mapped to short arm of chromosome 3 and may overlap or be adjacent to the Rps14 region. To determine whether the Rps14 loci is distinct from these Rps loci, 204 accessions showing resistance to P. sojae according to USDA germplasm collection, 9 ancestral lines for Rps genes on chromosome 3 and the Rps14 donor line PI 340029 were selected for haplotype analysis. SNP genotypic data on the 540kb region defined by SSR marker BARCSOYSSR_03_0226 and BARCSOYSSR_03_0266 were extracted. The generation of SNP data was previously described (Li et al., 2016), and a total of 31 SNPs in the defined region were called from these 213 different soybean accessions. Based on the topology of the neighbor-joining tree, the donor line of Rps14, PI 340029, belongs to a distinct branch compared with ancestral lines for other known Rps genes on chromosome 3.

By genotyping with two flanking markers (InDel4033 and InDel4263), eight homozygous resistance families were tested with eight homozygous susceptible families as control. Rps14 was resistant to all 13 P. sojae isolates, with all homozygous susceptible families and Williams showing intolerance to the disease (Table 22).

TABLE 22

Marker Assisted Resistance Spectrum Analysis of Rps14 to Isolates of P. sojae

| P. sojae | $F_{3,4}$ families selected[a] | | Parental lines | | Rps genes on Chr03 | | | | | |
|---|---|---|---|---|---|---|---|---|---|---|
| Isolate | Rps14 | Rps14 | PI 340029 | Williams | 1-a | 1-b | 1-c | 1-d | 1-k | UN1[c] |
| Race1 | R[b] | S | R | S | R | R | R | R | R | R |
| Race3 | R | S | R | S | S | R | R | R | R | I |
| Race4 | R | S | R | S | S | R | S | R | S | S |
| Race7 | R | S | R | S | S | R | R | R | R | R |
| Race13 | R | S | R | S | R | R | R | I | R | R |
| Race17 | R | S | R | S | S | S | R | S | R | R |
| Race25 | R | S | R | S | S | S | S | R | S | S |
| ISA19A-1 | R | S | R | S | S | S | R | S | S | R |
| ISA71D-1 | R | S | R | S | S | I | S | S | S | S |
| MIN12001.01.05 | R | S | R | S | R | R | S | S | R | — |
| MIN12004.01.01 | R | S | R | S | S | S | S | I | S | — |
| MIN12004.03.01 | R | S | R | S | S | S | S | S | S | — |
| MIN12005.07.02 | R | S | R | S | S | S | R | S | S | — |

[a]InDel4033 and InDel14261 are two molecular markers used for selections. The resistance pattern of Rps14 against each P. sojae isolate was scored by the proportion of resistance progenies in 8 selected homozygous resistant $F_{2:3}$ families The reaction of Rps14 was evaluated from 8 homozygous susceptible $F_{2:3}$ families.
[b]A family was recorded as resistant if >75% of seedlings survived after inoculation, susceptible if <25% of seedlings survived, and intermediate resistant if the proportion of resistant seedlings was between 25% and 75%.
[c]Phenotypes is based on Lin et al. 2013.

Rps14 was initially mapped to Rps1 region also harboring Rps1a, Rps1b, Rps1c, Rps1d, Rps1k and RpsUN1. However, none of these Rps1 genes showed similar resistance pattern as Rps14. The resistance pattern combined with the haplotype analysis demonstrate that Rps14 is likely a novel gene rather than a novel Rps1 allele.

Example 8

This example demonstrates expression of the Rps14 in plants to increase resistance to Phytophthora sojae.

The Rps14 genomic interval will be further fine mapped using a large F3 mapping population derived from a cross between PI 340029 and the susceptible Williams cultivar. The mapping population will be genotyped with molecular markers to identify recombinant lines. The recombinants will be phenotyped with Phytophthora sojae isolate Race 1. Based on the fine mapping the Rps14 QTL region will be narrowed down to a smaller genomic interval comprising candidate genes for further confirmation. For identifying candidate genes for Rps14, the whole genome sequence of PI 340029 will be generated using the PacBio sequencing platform. Contig harboring the flanking markers for the Rps14 genomic interval will be used as a reference sequence for comparing to the sequence data from the susceptible lines in order to characterize the genes and identify candidate genes based on the NBS type R-genes. The NBS type R-genes will be further analyzed for their gene structure to determine if it is a complete NB S type gene or truncated. Gene expression analysis will also be done to determine the expression profile of the NBS type R-genes in the recombinants. Together, with these analyses candidate genes will be expected to be identified for Rps14. Constructs comprising the candidate genes will be generated and transformed into soybean lines that do not carry the Rps14 candidate gene to confirm the Rps14 candidate gene and determining if expression of Rps14 candidate gene in plants increases resistance to *Phytophthora sojae*.

Single copy T0 transgenic events will be selected based on the PCR analysis with primers specific to the cloning vector. Final confirmation of the Rps14 gene expression in plants for resistance to *Phytophthora sojae* will be done in the homozygous T2 plants for the Rps14 candidate gene. T2 plants homozygous for the Rps14 candidate gene will be expected to increase resistance to *Phytophthora sojae* isolates as compared to plants not carrying the Rps14 gene. These results would confirm the Rps14 gene.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

Terms used in the claims and specification are defined as set forth below unless otherwise specified. It must be noted that, as used in the specification and the appended claims, the singular forms "a," "an" and "the" include plural referents unless the context clearly dictates otherwise.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

What is claimed is:

1. A method of introgressing a *Phytophthora* Root and Stem Rot (PRSR) resistance gene into a soybean plant, said PRSR resistance gene comprising a polynucleotide encoding a polypeptide having at least 95% sequence identity to SEQ ID NO: 2, said method comprising;

i) crossing a PRSR resistant soybean plant comprising a heterologous polynucleotide encoding a polypeptide having at least 95% sequence identity to SEQ ID NO: 2 with a second soybean plant to produce progeny;

ii) screening said progeny with a nucleic acid marker to detect progeny comprising a polymorphism genetically linked to said PRR resistance gene; and iii) selecting progeny that comprise said polymorphism to obtain soybean plants that contain said PRSR resistance gene.

2. The method of claim 1, wherein a plant produced from said selected progeny have an increased resistance to at least one race of *Phytophthora* relative to a plant lacking said PRSR resistance gene.

3. The method of claim 1, wherein said polymorphism is within 10 centimorgans of said nucleic acid encoding a polypeptide having at least 95% sequence identity to SEQ ID NO: 2.

4. The method of claim 2, wherein the at least one race of *Phytophthora* is at least one of Race1, Race 2, Race3, Race4, Race5, Race6, Race7, Race8, Race9 Race13, Race17, Race25, or Race31.

5. A method for generating a soybean plant having enhanced *Phytophthora* resistance, the method comprising:

(a) introducing a polynucleotide encoding a polypeptide comprising an amino acid sequence having at least 95% sequence identity to SEQ ID NO: 2 into the cells of a soybean plant, and (b) identifying a generated soybean plant that comprises the cells expressing said introduced polynucleotide, wherein the identified plant has increased resistance to a *Phytophthora* infection as compared to a soybean plant not comprising the introduced polynucleotide.

6. The method of claim 5, wherein said polynucleotide is introduced into the cells of a soybean plant i) by transforming isolated cells with a polynucleotide encoding a polypeptide comprising an amino acid sequence having at least 95% sequence identity to SEQ ID NO: 2, and regenerating the transformed cells into a transformed soybean plant; or ii) by crossing a PRSR resistant soybean plant that comprises a heterologous polynucleotide encoding a polypeptide comprising an amino acid sequence having at least 95% sequence identity to SEQ ID NO: 2 with a second soybean plant to produce a soybean plant comprising cells expressing said introduced polynucleotide.

7. The method of claim 5, wherein said introduced polynucleotide comprises a heterologous promoter operably linked to the polynucleotide encoding an amino acid sequence having at least 95% sequence identity to SEQ ID NO: 2.

8. The method of claim 5, wherein said identifying step comprises screening said generated soybean plant with a nucleic acid marker to detect progeny comprising a polymorphism genetically linked to said PRSR resistance gene.

* * * * *

UNITED STATES PATENT AND TRADEMARK OFFICE
CERTIFICATE OF CORRECTION

PATENT NO. : 11,466,287 B2
APPLICATION NO. : 17/575218
DATED : October 11, 2022
INVENTOR(S) : Jianxin Ma et al.

It is certified that error appears in the above-identified patent and that said Letters Patent is hereby corrected as shown below:

In the Claims

In Claim 1, Column 133, Line 21, the word "heterologous" should be deleted.

In Claim 1, Column 133, Line 27, the word "PRR" should read --PRSR--.

In Claim 2, Column 133, Line 33, the phrase "a plant produced from" should be deleted.

In Claim 6, Column 134, Line 31, the word "heterologous" should be deleted.

Signed and Sealed this
Third Day of January, 2023

Katherine Kelly Vidal
*Director of the United States Patent and Trademark Office*